US006420403B1

(12) United States Patent
Iwanowicz et al.

(10) Patent No.: US 6,420,403 B1
(45) Date of Patent: Jul. 16, 2002

(54) INHIBITORS OF IMPDH ENZYME

(76) Inventors: Edwin J. Iwanowicz, 30 Haverford Rd., Cranbury, NJ (US) 08512; T. G. Murali Dhar, 247 Crittenden Dr., Newtown, PA (US) 18940; Katerina Leftheris, 92 Richmond Dr., Skillman, NJ (US) 08558; Chunjian Liu, 208 White Pine Cir., Lawrenceville, NJ (US) 08648; Toomas Mitt, 1312 Aspen Dr., Plainsboro, NJ (US) 08536; Scott H. Watterson, 6 Fern Ct., Hamilton, NJ (US) 08690; Joel C. Barrish, 38 Dorchester La., Richboro, PA (US) 18954

( * ) Notice: Subject to any disclaimer, the term of this patent is extended or adjusted under 35 U.S.C. 154(b) by 0 days.

(21) Appl. No.: 09/428,609

(22) Filed: Oct. 27, 1999

Related U.S. Application Data

(60) Provisional application No. 60/106,184, filed on Oct. 29, 1998.

(51) Int. Cl.$^7$ ....................... C07D 263/34; A61K 31/42
(52) U.S. Cl. ........................................ 514/374; 548/236
(58) Field of Search ............................ 548/236; 514/374

(56) References Cited

U.S. PATENT DOCUMENTS

| | | | |
|---|---|---|---|
| 4,686,234 A | 8/1987 | Nelson et al. | 514/469 |
| 4,725,622 A | 2/1988 | Nelson et al. | 514/469 |
| 4,727,069 A | 2/1988 | Nelson et al. | 514/211 |
| 4,753,935 A | 6/1988 | Nelson et al. | 514/233.5 |
| 4,786,637 A | 11/1988 | Allison et al. | 514/233.5 |
| 4,808,592 A | 2/1989 | Nelson et al. | 514/233.5 |
| 4,861,776 A | 8/1989 | Nelson et al. | 514/233.5 |
| 4,868,153 A | 9/1989 | Allison et al. | 514/470 |
| 4,948,793 A | 8/1990 | Allison et al. | 514/233.5 |
| 4,952,579 A | 8/1990 | Nelson et al. | 514/233.5 |
| 4,959,387 A | 9/1990 | Nelson et al. | 524/469 |
| 4,992,467 A | 2/1991 | Allison et al. | 514/464 |
| 5,247,083 A | 9/1993 | Knox et al. | 544/153 |
| 5,374,643 A | * 12/1994 | Atwal et al. | 514/364 |
| 5,380,879 A | 1/1995 | Sjogren | 549/310 |
| 5,444,072 A | 8/1995 | Patterson et al. | 514/320 |
| 5,665,583 A | 9/1997 | Collart et al. | 435/191 |
| 5,807,876 A | 9/1998 | Armistead et al. | 514/374 |
| 6,054,472 A | 4/2000 | Armistead et al. | 514/374 |

FOREIGN PATENT DOCUMENTS

| | | |
|---|---|---|
| WO | WO94/01105 | 1/1994 |
| WO | WO94/12184 | 6/1994 |
| WO | WO97/40028 | 10/1997 |
| WO | WO98/40381 | 9/1998 |
| WO | WO99/55663 | 11/1999 |
| WO | WO00/56331 | 9/2000 |

OTHER PUBLICATIONS

Nature 256:331–333 (1975) Jackson et al.
J. Biol.Chem. 263:15769–15662 (1988) Collart et al.
J. Biol.Chem. 265:5292–5295 (1990) Natsumeda et al.
J. Biol.Chem. 266:506–509 (1991) Weber.
J. Biol.Chem. 268:27286–27290 (1993) Carr.

* cited by examiner

*Primary Examiner*—Bruck Kifle
(74) *Attorney, Agent, or Firm*—Audrey F. Sher; Anastasia P. Winslow

(57) ABSTRACT

The present invention discloses the identification of the novel inhibitors of IMPDH (inosine-5'-monophosphate dehydrogenase). The compounds and pharmaceutical compositions disclosed herein are useful in treating or preventing IMPDH-associated disorders, such as transplant rejection and autoimmune diseases.

23 Claims, No Drawings

INHIBITORS OF IMPDH ENZYME

This invention claims priority from provisional U.S. application Ser. No. 60/106,184, filed Oct. 29, 1998, which is incorporated herein by reference in its entirety.

FIELD OF THE INVENTION

The present invention relates to novel compounds which inhibit IMPDH. The invention also encompasses pharmaceutical compositions comprising these compounds. The compounds and pharmaceutical compositions of the invention are particularly well suited for inhibiting IMPDH enzyme activity and, consequently, may be advantageously used as therapeutic agents for IMPDH-associated dissorders. This invention also relates to methods for inhibiting the activity of IMPDH using the compounds of this invention and related compounds.

BACKGROUND OF THE INVENTION

Inosine monophosphate dehydrogenase (IMPDH) has been shown to be a key enzyme in the regulation of cell proliferation and differentiation. Nucleotides are required for cells to divide and replicate. In mammals, nucleotides may be synthesized through one of two pathways: the de novo synthesis pathway or the salvage pathway. The extent of utilization of each pathway is dependent on the cell type. This selectivity has ramifications with regard to therapeutic utility as described below.

IMPDH is involved in the de novo synthesis of guanosine nucleotides. IMPDH catalyzes the irreversible NAD-dependent oxidation of inosine-5'-monophosphate ("IMP") to xanthosine-5'-monophosphate ("XMP"), Jackson et al., *Nature* 256:331–333 (1975).

IMPDH is ubiquitous in eukaryotes, bacteria and protozoa. The prokaryotic forms share 30–40% sequence identity with the human enzyme.

Two distinct cDNA's encoding IMPDH have been identified and isolated. These transcripts are labeled type I and type II and are of identical size (514 amino acids). Collart et al., *J. Biol. Chem.* 263:15769–15772 (1988); Natsumeda et al., *J. Biol. Chem.* 265:5292–5295 (1990); and U.S. Pat. NO. 5,665,583 to Collart et al. These isoforms share 84% sequence identity. IMPDH type I and type II form tetramers in solution, the enzymatically active unit.

B and T-lymphocytes depend on the de novo, rather than salvage pathway, to generate sufficient levels of nucleotides necessary to initiate a proliferative response to mitogen or antigen. Due to the B and T cell's unique reliance on the de novo pathway, IMPDH is an attractive target for selectively inhibiting the immune system without also inhibiting the proliferation of other cells.

Immunosuppression has been achieved by inhibiting a variety of enzymes. Examples include: phosphatase calcineurin (inhibited by cyclosporin and FK-506); dihydroorotate dehydrogenase (DHODase), an enzyme involved in the biosynthesis of pyrimidines (inhibited by leflunomide and brequinar); the kinase FRAP (inhibited by rapamycin); and the heat shock protein hsp70 (inhibited by deoxyspergualin).

Inhibitors of IMPDH have also been described in the art. WO 97/40028 and U.S. Pat. No. 5,807,876 describe a class of urea derivatives that possess a common urea backbone. A large number of compounds are described in WO 97/40028 and U.S. Pat. No. 5,807,876, but several of the compounds suffer from drawbacks such as inferior solubility. A recent publication, WO 98/40381, describes a series of heterocyclic substituted anilines as inhibitors of IMPDH.

U.S. Pat. Nos. 5,380,879 and 5,444,072 and PCT publications WO 94/01105 and WO 94/12184 describe mycophenolic acid ("MPA") and some of its derivatives as potent, uncompetitive, reversible inhibitors of human IMPDH type I and type II. MPA has been demonstrated to block the response of B and T-cells to mitogen or antigen. Immunosuppressants, such as MPA and derivatives of MPA, are useful drugs in the treatment of transplant rejection, autoimmune disorders, psoriasis, inflammatory diseases including rheumatoid arthritis, tumors, and allograft rejection. These are described in U.S. Pat. Nos. 4,686234, 4,725622, 4,727,069, 4,753,935, 4,786,637, 4,808,592, 4,861,776, 4,868,153, 4,948,793, 4,952,579, 4,959,387, 4,992,467, 5.247,083; and U.S. patent application Ser. No. 07/927,260, filed Aug. 7, 1992. However, MPA displays undesirable pharmacological properties, such as gastrointestinal toxicity and poor bioavailability.

Tiazofurin, ribavirin and mizoribine also inhibit IMPDH. These nucleoside analogs are competitive inhibitors of IMPDH, however these agents inhibit other NAD dependent enzymes. This low level of selectivity for IMPDH limits the therapeutic application of tiazofurin, ribavirin and mizoribine. Thus, new agents which have improved selectivity for IMPDH would represent a significant improvement over the nucleoside analogs.

Mycophenolate mofetil, sold under the trade name CELLCEPT, is a prodrug which liberates MPA in vivo. It is approved for use in preventing acute renal allograft rejection following kidney transplantation. The side effect profile limits the therapeutic potential of this drug. MPA is rapidly metabolized to the inactive glucuronide in vivo. In humans, the blood levels of glucuronide exceed that of MPA. The glucuronide undergoes enterohepatic recycling causing accumulation of MPA in the bile and subsequently in the gastrointestinal tract. This together with the production of the inactive glucuronide effectively lowers the drug's in vivo potency, while increasing its undesirable gastrointestinal side effects.

Unlike type I, type II mRNA is preferentially upregulated in human leukemic cell lines K562 and HL-60. Weber, *J. Biol. Chem.* 266: 506–509 (1991). In addition, cells from human ovarian tumors and leukemic cells from patients with chronic granulocytic, lymphocytic and acute myeloid leukemias also display an up regulation type II mRNA. This disproportionate increase in IMPDH activity in malignant cells may be addressed through the use of an appropriate IMPDH inhibitor. IMPDH has also been shown to play a role in the proliferation of smooth muscle cells, indicating that inhibitors of IMPDH may be useful in preventing restenosis or other hyperproliferative vascular diseases.

IMPDH has been shown to play a role in viral replication in some viral cell lines. Carr, *J. Biol. Chem.* 268:27286–27290 (1993). The IMPDH inhibitor VX-497, is currently being evaluated for the treatment of hepatitis C virus in humans. Ribavirin has also been used in the treatment of hepatitis C and B viruses and when used in combination with interferon an enhancement in activity was observed. The IMPDH inhibitor ribavirin is limited by its lack of a sustained response in monotherapy and broad cellular toxicity.

There remains a need for potent selective inhibitors of IMPDH with improved pharmacological properties, physical properties and fewer side effects. Such inhibitors would have therapeutic potential as immunosuppressants, anti-cancer agents, anti-vascular hyperproliferative agents, anti-inflammatory agents, antifungal agents, antipsoriatic and anti-viral agents. The compounds of the present invention differ from those taught by the prior art and are effective inhibitors of IMPDH.

SUMMARY OF THE INVENTION

The present invention provides compounds of the following Formula I, and salts thereof, for use as inhibitors of IMPDH enzyme:

(I)

wherein:
- X is selected from the group consisting of —C(O)—, —C(S)—, and —S(O)$_2$—;
- A is a monocyclic or bicyclic ring system optionally comprising up to 4 heteroatoms selected from N, O, or S, and wherein a $CH_2$ adjacent to any of said N, O, or S, heteroatoms is optionally substituted with oxo (=O); and each ring is optionally substituted with up to 3 substituents, wherein:
    - the first of said substituents, if present, is selected from the group consisting of $R^1$, $R^2$, and $R^3$;
    - the second of said substituents, if present, is selected from the group consisting of $R^1$ and $R^2$; and
    - the third of said substituents, if present, is selected from the group consisting of $R^1$ and $R^2$;
- $R^1$ is selected from a monocyclic ring system comprising 4 to 6 members per ring, wherein said ring system optionally comprises up to 4 heteroatoms selected from N, O, or S, and wherein a $CH_2$ adjacent to any of said N, O, or S heteroatoms is optionally substituted with oxo (=O); and each $R^1$ optionally comprises up to 3 substituents selected from $R^2$ or $R^3$;
- $R^2$ is selected from halogen, CN, $NO_2$, $CF_3$, $(C_0–C_4$ alkyl)$OR^3$, $OCF_3$, $OC(O)R^3$, $OC(O)OR^3$, $O(C)NR^3R^4$, $(C_0–C_4$ alkyl)$C(O)R^3$, $(C_0–C_4$ alkyl)$C(O)OR^3$, $(C_0–C_4$ alkyl)$C(O)OR^3$, $(C_0–C_4$ alkyl)$C(O)NR^3R^4$, $(C_0–C_4$ alkyl)$CONR^3S(O)_2R^5$, $(C_0–C_4$ alkyl)$C(O)N(OR^3)R^3$, $(C_0–C_4$ alkyl)$SR^3$, $(C_0–C_4$ alkyl)$SR^3$, $(C_0–C_4$ alkyl)$S(O)R^5$, $(C_0–C_4$ alkyl)$S(O)_2R^5$, $(C_0–C_4$ alkyl)$S(O)R^5$, $(C_0–C_4$ alkyl)$S(O)_2R^5$, $(C_0–C_4$ alkyl)$S(O)_2NR^3R^4$, $(C_0–C_4$ alkyl)$S(O)_2NR^3C(O)R^4$, $(C_0–C_4$ alkyl)$NR^3R^4$, $(C_0–C_4$ alkyl)$NR^3C(O)NR^4$, $(C_0–C_4$ alkyl)$NR^3C(O)R^4$, $(C_0–C_4$ alkyl)$NR^3C(O)OR^5$, $(C_0–C_4$ alkyl)$NR^3S(O)_2R^5$, $(C_0–C_4$ alkyl)$S(O)_2OR^3$, $(C_0–C_4$ alkyl)$P(O)(OH)OR^3$, —J—$(C_0–C_4$ alkyl)$OR^3$, —J—$(C_1–C_4$ alkyl)$C(O)OR^3$, —J—$(C_1–C_4$ alkyl)$CONR^3S(O)_2R^5$, —J—$(C_1–C_4$ alkyl)$S(O)_2NR^3R^4$, —J—$(C_1–C_4$ alkyl)$S(O)_2NR^3C(O)R^4$, $(C_0–C_4$ alkyl)tetrazol-5-yl, and —J—$(C_1–C_4$ alkyl)tetrazol-5-yl, wherein J is chosen from O, S, and $NR^3$;
- $R^3$ is selected from hydrogen, $(C_1–C_4)$ alkyl, $(C_2–C_4)$alkenyl or $(C_2–C_4)$alkynyl, aryl$(C_0–C_4)$ alkyl-, heterocyclic$(C_0–C_4)$ alkyl- and cycloalkyl $(C_0–C_4)$ alkyl-, wherein said groups are substituted with 0-2 substituents independently selected from $R^6$;
- $R^4$ is selected from hydrogen, $(C_1–C_4)$ alkyl, $(C_2–C_4)$-alkenyl, $(C_2–C_4)$alkynyl, aryl$(C_0–C_4)$ alkyl-, heterocyclic$(C_0–C_4)$alkyl-, cycloalkyl $(C_0–C_4)$ alkyl-, $(C_0–C_4)$alkylcarbonyl, aryl $(C_0–C_4)$alkylcarbonyl, heterocyclic$(C_0–C_4)$ alkylcarbonyl, $(C_1–C_4)$alkyloxycarbonyl, aryl $(C_1–C_4)$alkyloxycarbonyl, and heterocyclic $(C_1–C_4)$alkyloxycarbonyl, wherein said groups are substituted with 0-2 substituents independently selected from $R^6$;

alternatively, $R^3$ and $R^4$, when both substituents are on the same nitrogen atom, as in (—$NR^3R^4$), can be taken together with the nitrogen atom to which they are attached to form a heterocycle selected from the group consisting of 1-aziridinyl, 1-azetidinyl, 1-piperidinyl, 1-morpholinyl, 1-pyrrolidinyl, thiamorpholinyl, thiazolidinyl, and 1-piperazinyl, said heterocycle being optionally substituted with 0-3 groups selected from the group consisting of oxo, $R^6$, $C_1–C_6$ alkyl, $C_3–C_7$ cycloalkyl($C_0–C_4$ alkyl)-, $C_1–C_6$ alkylcarbonyl, $C_3–C_7$ cycloalkyl($C_0–C_5$ alkyl)carbonyl, $C_1–C_6$ alkoxycarbonyl, $C_3–C_7$ cycloalkyl($C_0–C_5$ alkoxy) carbonyl, aryl($C_0–C_5$ alkyl), heterocyclic($C_0–C_5$ alkyl), aryl($C_1–C_5$ alkoxy)carbonyl, heterocyclic $(C_1–C_5$ alkoxy)carbonyl, $C_1–C_6$ alkylsulfonyl, arylsulfonyl, and heterocyclicsulfonyl, wherein said aryl or heterocyclic groups are substituted with 0-2 substituents independently selected from the group consisting of $C_1–C_4$ alkyl, $C_1–C_4$ alkoxy, F, Cl, Br, $CF_3$, CN, and $NO_2$;

- $R_5$ is selected from $(C_1–C_4)$ alkyl, $(C_2–C_4)$ alkenyl, $(C_2–C_4)$alkynyl, aryl$(C_0–C_4)$ alkyl-, heterocyclic $(C_0–C_4)$ alkyl-, and cycloalkyl$(C_0–C_4)$ alkyl-, and each $R^3$ optionally comprises up to 2 different or identical substituents selected from $R^6$;
    - $R^6$ is selected from H, halogen, $NO_2$, CN, $C_1–C_4$alkyl, $C_3–C_{10}$ cycloalkyl, $C_2–C_6$ alkenyl, $C_2–C_6$alkynyl, haloalkyl, haloalkoxy, OH, hydroxy $C_1–C_4$ alkyl, $C_1–C_4$ alkoxy, $C_1–C_4$ alkylcarbonyl, $NH_2$, $(C_0–C_4$ alkyl)$_{0-2}$ alkylamino, $C_0–C_4$ alkylthio, $C_1–C_4$ alkylsulfonyl, aryl $C_0–C_4$ alkylsulfonyl, $(C_0–C_4$ alkyl)$_0$, alkylaminosulfonyl-, $(C_0–C_4$ alkylcarbonylaminosulfonyl-, aryl$C_0–C_4$ alkylsulfonylaminocarbonyl, $C_1–C_4$ alkylsulfonylaminocarbonyl carboxylate, $C_1–C_4$ alkyloxycarbonyl, $(C_0–C_4$ alkyl)$_{02}$ aminocarbonyl-, and $(C_0–C_4$ alkyl)tetrazol-5-yl;

B is a monocyclic or bicyclic ring system optionally comprising up to 4 heteroatoms selected from N, O, or S, and wherein a $CH_2$ adjacent to any of said N, O, or S heteroatoms is optionally substituted with oxo (=O); wherein each ring system is substituted with one substituent selected from $R^7$, $R^8$ or $R^9$, and is optionally substituted with a second and/or a third substituent, wherein:
- the second of said substituents, if present, is selected from $R^7$, $R^8$, $R^9$, $R_{10}$, $R^{11}$, $R^{12}$; and
- the third of said substituents, if present is selected from $R^{10}$, $R^{11}$, and $R^{12}$;

$R^7$ is selected from $(C_0–C_6)$ alkyl, $(C_2–C_6)$ alkenyl or $(C_2–C_6)$ alkynyl and $R^7$ is substituted with:

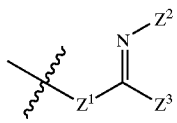

$R^8$ is selected from $(C_0–C_6)$ alkyl, $(C_2–C_6)$ alkenyl or $(C_2–C_6)$alkynyl and $R^8$ is substituted with:

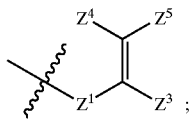

$R^9$ is selected from $(C_0–C_6)$-alkyl or $(C_2–C_6)$-alkenyl or $(C_2–C_6)$alkynyl and $R^9$ is substituted with:

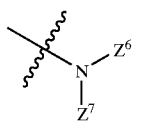

$Z^1$ is selected from the group consisting of O, S, and $NR^3$;

$Z^2$ is selected from the group consisting of H, $C_1$–$C_4$ alkyl, $C_3$–$C_6$ cycloalkyl, CN, $CF_3$, $OR^3$, heterocycle, $NO_2$, $C(O)R^3$, $C(O)_2R^3$, $C(O)NR^3R^4$, $S(O)_2NR^3R^4$, and $S(O)_2R^5$;

$Z^3$ is selected from the group consisting of $OR^3$, $SR^3$, and $NR^3R^4$;

$Z^4$ is selected from the group consisting of H, halo, $C_1$–$C_4$ alkyl, $C_3$–$C_6$ cycloalkyl, CN, $CF_3$, heterocycle, $NO_2$, $C(O)R^3$, $C(O)_2R^3$, $C(O)NR^3R^4$, $S(O)_2NR^3R^4$, and $S(O)_2R^5$;

$Z^5$ is selected from the group consisting of halo, CN, $CF_3$, heterocycle, $NO_2$, $C(O)R^3$, $C(O)_2R^3$, $C(O)NR^3R^4$, $S(O)_2NR^3R^4$, and $S(O)_2R^5$;

$Z^6$ is selected from the group consisting of H, $C(O)H$, $C(O)R^3$, $C(O)OR^5$, $C(O)NR^3R^4$, $S(O)R^5$ and $S(O)_2R^5$;

$Z^7$ is selected from the group consisting of OH, $OR^3$ and $NR^3R^4$, $R^{10}$ is selected from hydrogen, $(C_1$–$C_4)$ alkyl, $(C_2$–$C_4)$alkenyl or alkynyl, aryl, heterocyclic, and cycloalkyl, and each $R^{10}$ optionally comprises up to 3 substituents selected from $R^{11}$ or $R^{12}$;

$R^{11}$ is selected from the group consisting of H, halogen, $NO_2$, CN, $C_1$–$C_4$alkyl, $C_3$–$C_{10}$ cycloalkyl, $C_2$–$C_6$ alkenyl, $C_2$–$C_6$alkynyl, haloalkyl, haloalkoxy, OH, $C_1$–$C_4$ alkoxy, $C_1$–$C_4$ alkylcarbonyl, $NH_2$, $(C_0$–$C_4$ alkyl$)_{0-2}$ alkylamino, $C_0$–$C_4$ alkylthio, $C_1$–$C_4$ alkylsulfonyl, aryl $C_0$–$C_4$ alkylsulfonyl, $(C_0$–$C_4$ alkyl$)_{0-2}$ alkylaminosulfonyl-, $(C_0$–$C_4$ alkylcarbonylaminosulfonyl-, aryl$C_0$–$C_4$ alkylsulfonylaminocarbonyl, $C_1$–$C_4$ alkylsulfonylaminocarbonyl carboxylate, $C_1$–$C_4$ alkyloxycarbonyl, $(C_0$–$C_4$ alkyl$)_{0-2}$ aminocarbonyl-, and $(C_0$–$C_4$ alkyl)tetrazol-5-yl;

$R^{12}$ is selected from H, alkyl, $(C_1$–$C_6)$ alkyloxy, $C_3$–$C_6$ cycloalkyl, heterocycle and aryl.

Also encompassed within the scope of the present invention are compounds of the following Formula II, or salts thereof, for use as inhibitors of IMPDH enzyme:

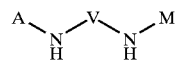

wherein:

V is $—C(NZ^2)—$ or $—C(CZ^9Z^{10})—$;

$Z^2$ is selected from the group consisting of lower alkyl, cycloalkyl, CN, $CF_3$, heterocycle, $NO_2$, $C(O)R^3$, $C(O)_2R^3$, $C(O)NR^3R^4$, $S(O)_2NR^3R^4$, and $S(O)_2R^5$;

$Z^9$ is selected the group consisting of H, lower alkyl, cycloalkyl, CN, $CF_3$, heterocycle, $NO_2$, $C(O)R^3$, $C(O)_2R^4$, $C(O)NR^3R^4$, $S(O)_2NR^3R^4$, and $S(O)_2R^5$;

$Z^{10}$ is selected the group consisting of CN, $CF_3$, heterocycle, $NO_2$, $C(O)R^3$, $C(O)_2R^3$, $C(O)NR^3R^4$, $S(O)_2NR^3R^4$, and $S(O)_2R^5$;

A is 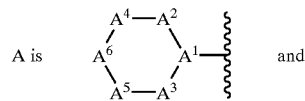 and $A^1$ is C or $CS^1$;

$A^2$ is selected from the group consisting of
1) a heteroatom selected from the group consisting of nitrogen, oxygen and sulfur,
2) $CS^2$,
3) CO,
4) $NS^7$,
5) $S(O)_2$;

$A^3$ is selected from the group consisting of
1) a heteroatom selected from the group consisting of nitrogen, oxygen and sulfur,
2) $CS^3$,
3) CO,
4) $NS^7$,
5) $S(O)_2$;

$A^4$ is selected from the group consisting of
1) a heteroatom selected from the group consisting of nitrogen, oxygen and sulfur,
2) $CS^4$,
3) CO,
4) $NS^7$,
5) $S(O)_2$,
6) a bond;

$A^5$ is selected from the group consisting of
1) a heteroatom selected from the group consisting of nitrogen, oxygen and sulfur,
2) $CS^5$,
3) CO,
4) $NS^7$,
5) $S(O)_2$;

$A^6$ is selected from the group consisting of
1) a heteroatom selected from the group consisting of nitrogen, oxygen and sulfur,
2) $CS^6$,
3) CO,
4) $NS^7$,
5) $S(O)_2$;

$A^4$, $A^6$ and the atoms to which they are attached together may form a bicyclic ring system containing 0–2 additional heteroatoms selected from nitrogen, oxygen and sulphur;

$A^5$, $A^6$ and the atoms to which they are attached together may form a bicyclic ring system containing 0–2 additional heteroatoms selected from nitrogen, oxygen and sulphur;

Wherein $A^2$, $A^3$, $A^4$, $A^5$, and $A^6$, are chosen such that the total number of heteroatoms in the monocyclic or bicyclic ring system does not exceed four, and the attached substituents $S^1$, $S^2$, $S^3$, $S^4$, $S^5$, $S^6$, and $S^7$ are chosen such that the total number of non-hydrogen substituents does not exceed four;

$S^1$ is selected from H, $C_1$–$C_3$ alkyl and halo;
$S^2$ is selected from H, $C_1$–$C_3$ alkyl and halo;
$S^3$ is selected from H, $C_1$–$C_3$ alkyl and halo;
$S^4$ is selected from H, $R^1$, $R^2$ or $R^3$;
$S^5$ is selected from H, $R^1$, $R^2$ or $R^3$;
$S^6$ is selected from $R^1$, $R^2$ or $R^5$;
$S^7$ is selected from $R^3$, or $R^4$;

$R^1$ is a monocyclic ring system comprising 4 to 6 members per ring, wherein said ring system optionally comprises up to 4 heteroatoms selected from N, O, or S, and wherein a $CH_2$ adjacent to any of said N, O, or S heteroatoms is optionally substituted with oxo (=O); and each $R^1$ optionally comprises up to 3 substituents selected from $R^2$ or $R^3$;

$R^2$ is selected from halogen, CN, $NO_2$, $CF_3$, $(C_0$–$C_4$ alkyl)$OR^3$, $OCF_3$, $OC(O)R^3$, $OC(O)OR^3$, $O(C)NR^3R^4$, $(C_0$–$C_4$ alkyl)$C(O)R^3$, $(C_0$–$C_4$ alkyl)$C(O)OR^3$, $C_0$–$C_4$ alkyl)$C(O)OR^3$, $(C_4$–$C_4$ alkyl)$C(O)NR^3R^4$, $(C_0$–$C_4$ alkyl)$CONR^3S(O)_2R^5$, $(C_0$–$C_4$ alkyl)$C(O)N(OR^3)R^3$, $(C_0$–$C_4$ alkyl)$SR^3$, $(C_0$–$C_4$ alkyl)$SR^3$, $(C_0$–$C_4$ alkyl)$S(O)R^5$, $(C_{04}$ alkyl)$S(O)_2R^5$, $(C_0$–$C_4$ alkyl)$S(O)R^5$, $(C_0$–$C_4$ alkyl)$S(O)_2R^5$, $(C_0$–$C_4$ alkyl)$S(O)_2NR^3R^4$, $(C_0$–$C_4$ alkyl)$S(O)_2NR^3C(O)R^4$, $(C_0$–$C_4$ alkyl)$NR^3R^4$, $(C_0$–$C_4$ alkyl)$NR^3C(O)NR^4$, $(C_0$–$C_4$ alkyl)$NR^3C(O)R^4$, $(C_0$–$C_4$ alkyl)$NR^3C(O)OR^5$, $(C_1$–$C_4$ alkyl)$NR^3C(O)NR_3R^{5a}$, $(C_0$–$C_4$ alkyl)$NR^3S(O)_2R^5$, $(C_0$–$C_4$ alkyl)$S(O)_2OR^3$, $(C_0$–$C_4$ alkyl)$P(O)(OH)OR^3$, —J—$(C_0$–$C_4$ alkyl)$OR^3$, —J—$(C_1$–$C_4$ alkyl)$C(O)OR^3$, —J—$(C_1$–$C_4$ alkyl)$CONR^3S(O)_2R^5$, —J—$(C_1$–$C_4$ alkyl)$S(O)_2NR^3R^4$, —J—$(C_1$–$C_4$ alkyl)$S(O)_2NR^3C(O)R^4$, $(C_0$–$C_4$ alkyl)tetrazol-5-yl, and —J—$(C_1$–$C_4$ alkyl)tetrazol-5-yl, wherein J is chosen from O, S, and $NR^3$;

$R^3$ is selected from hydrogen, $(C_1$–$C_4)$ alkyl, $(C_2$–$C_4)$ alkenyl, $(C_2$–$C_4)$alkynyl, aryl$(C_0$–$C_4)$ alkyl-, heterocyclic$(C_0$–$C_4)$ alkyl-, and cycloalkyl$(C_0$–$C_4)$ alkyl-, wherein said groups are substituted with 0–2 substituents independently selected from $R^6$;

$R^4$ is selected from hydrogen, $(C_1$–$C_4)$ alkyl, $(C_2$–$C_4)$-alkenyl, $(C_2$–$C_4)$alkynyl, aryl$(C_0$–$C_4)$alkyl-, heterocyclic$(C_0$–$C_4)$alkyl-, cycloalkyl, $(C_0$–$C_4)$ alkylcarbonyl, aryl$(C_0$–$C_4)$alkylcarbonyl, heterocyclic$(C_0$–$C_4)$alkylcarbonyl, $(C_1$–$C_4)$ alkyloxycarbonyl, aryl$(C_1$–$C_4)$alkyloxycarbonyl, and heterocyclic$(C_1$–$C_4)$alkyloxycarbonyl, wherein said groups are substituted with 0–2 substituents independently selected from $R^6$;

alternatively, $R^3$ and $R^4$, when both substituents are on the same nitrogen atom, as in (—$NR^3R^4$), can be taken together with the nitrogen atom to which they are attached to form a heterocycle selected from the group consisting of 1-aziridinyl, 1-azetidinyl, 1-piperidinyl, 1-morpholinyl, 1-pyrrolidinyl, thiamorpholinyl, thiazolidinyl, and 1-piperazinyl, said heterocycle being optionally substituted with 0–3 groups selected from the group consisting of oxo, $R^6$, $C_1$–$C_6$ alkyl, $C_3$–$C_7$ cycloalkyl$(C_0$–$C_4$ alkyl)-, $C_1$–$C_6$ alkylcarbonyl, $C_3$–$C_7$ cycloalkyl$(C_0$–$C_5$ alkyl)carbonyl, $C_1$–$C_6$ alkoxycarbonyl, $C_3$–$C_7$ cycloalkyl$(C_0$–$C_5$ alkoxy)carbonyl, aryl $(C_0$–$C_5$ alkyl), heterocyclic$(C_0$–$C_5$ alkyl), aryl $(C_1$–$C_5$ alkoxy)carbonyl, heterocyclic$(C_1$–$C_5$ alkoxy)carbonyl, $C_1$–$C_6$ alkylsulfonyl, arylsulfonyl, and heterocyclicsulfonyl, wherein said aryl or heterocyclic groups are substituted with 0–2 substituents independently selected from the group consisting of $C_1$–$C_4$ alkyl, $C_1$–$C_4$ alkoxy, F, Cl, Br, $CF_3$, CN, and $NO_2$;

$R^5$ is selected from $(C_1$–$C_4)$alkyl, $(C_2$–$C_4)$alkenyl, $(C_2$–$C_4)$alkynyl, aryl$(C_0$–$C_4)$ alkyl-, heterocyclic $(C_0$–$C_4)$ alkyl-, or cycloalkyl$(C_0$–$C_4)$ alkyl-, and each $R^3$ optionally comprises up to 2 different or identical substituents selected from $R^6$;

$R^{5a}$ is selected from $(C_1$–$C_4)$alkyl, $(C_2$–$C_4)$alkenyl, $(C_2$–$C_4)$alkynyl, aryl$(C_1$–$C_4)$ alkyl-, heterocyclic $(C_1$–$C_4)$ alkyl-, or cycloalkyl$(C_1$–$C_4)$ alkyl-, and each $R^3$ optionally comprises up to 2 different or identical substituents selected from $R^6$;

$R^6$ is selected from H, halogen, $NO_2$, CN, $C_1$–$C_4$alkyl, $C_3$–$C_{10}$ cycloalkyl, $C_2$–$C_6$ alkenyl, $C_2$–$C_6$alkynyl, haloalkyl, haloalkoxy, OH, hydroxy $C_1$–$C_4$ alkyl, $C_1$–$C_4$ alkoxy, $C_1$–$C_4$ alkylcarbonyl, $NH_2$, $(C_0$–$C_4$ alkyl)$_{0-2}$ alkylamino, $C_{0-4}$ alkylthio, $C_1$–$C_4$ alkylsulfonyl, aryl $C_0$–$C_4$ alkylsulfonyl, $(C_0$–$_4$ alkyl)$_{0-2}$ alkylaminosulfonyl-, $(C_0$–$C_4$ alkylcarbonylaminosulfonyl-, aryl$C_0$–$C_4$ alkylsulfonylaminocarbonyl, $C_1$–$C_4$ alkylsulfonylaminocarbonyl carboxylate, $C_1$–$C_4$ alkyloxycarbonyl, $(C_0$–$C_4$ alkyl)$_{0-2}$ aminocarbonyl-, and $(C_0$–$C_4$ alkyl)tetrazol-5-yl;

M is selected from the group consisting of:
(i) $(C_1$–$C_6)$alkyl, $(C_2$–$C_6)$alkenyl, $(C_2$–$C_6)$alkynyl, and cycloalkyl$(C_1$–$C_4)$alkyl, optionally comprising up to 3 substituents selected from the group consisting of $R^1$, $R^2$, or $R^4$, wherein any $CH_2$ is optionally substituted with oxo (=O); and
(ii)

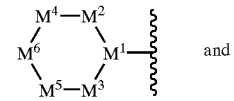 and $M^1$ is C or $CP^1$;
$M^2$ is selected from the group consisting of
  1) a heteroatom selected from the group consisting of nitrogen, oxygen and sulfur,
  2) $C(P^2)_{1-2}$,
  3) CO,
  4) $NP^7$,
  5) $S(O)_2$;
$M^3$ is selected from the group consisting of
  1) a heteroatom selected from the group consisting of nitrogen, oxygen and sulfur,
  2) $C(P^3)_{1-2}$,
  3) CO,
  4) $NP^7$,
  5) $S(O)_2$;
$M^4$ is selected from the group consisting of
  1) a heteroatom selected from the group consisting of nitrogen, oxygen and sulfur,
  2) $CP^4$,
  3) $CP^5$,
  4) $C(P^5)_{1-2}$,
  5) CO,
  6) $NP^7$,

7) S(O)$_2$;

M$^5$ is selected from the group consisting of
1) a heteroatom selected from the group consisting of nitrogen, oxygen and sulfur,
2) C(P$^5$)$_{1-2}$,
3) CO,
4) NP$^7$,
5) S(O)$_2$;

M$^6$ is selected from the group consisting of
1) a heteroatom selected from the group consisting of nitrogen, oxygen and sulfur,
2) C(P$^6$)$_{1-2}$,
3) CO,
4) NP$^7$,
5) S(O)$_2$,
6) a bond;

M$^4$, M$^6$ and the atoms to which they are attached together may form a bicyclic ring system containing 0–2 additional heteroatoms selected from nitrogen, oxygen and sulphur;

M$^5$, M$^6$ and the atoms to which they are attached together may form a bicyclic ring system containing 0–2 additional heteroatoms selected from nitrogen, oxygen and sulphur;

Wherein ,M$^2$, M$^3$, M$^4$, M$^5$, and M$^6$, are chosen such that the total number of heteroatoms in the monocyclic or bicyclic ring system does not exceed four, and the attached substituents P$^1$, P$^2$, P$^3$, P$^4$, P$^5$, P$^6$, and P$^7$ are chosen such that the total number of non-hydrogen substituents does not exceed four;

P$^1$ is selected from H, C$_1$–C$_3$ alkyl or halo;
P$^2$ is selected from H, C$_1$–C$_3$ alkyl or halo;
P$^3$ is selected from H, C$_1$–C$_3$ alkyl or halo;
P$^4$ is selected from R$^2$, R$^5$, R$^7$, R$^8$ or R$^9$;
P$^5$ is selected from H, R$^2$ or R$^3$;
P$^6$ is selected from H, R$^2$, R$^3$, R$^4$, R$^7$, R$^8$ or R$^9$;
P$^7$ is selected from R$^3$ or R$^4$;

R$^7$ is selected from (C$_0$–C$_6$) alkyl, (C$_2$–C$_6$) alkenyl or (C$_2$–C$_6$)alkynyl and R$^7$ is substituted with:

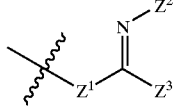

R$^8$ is elected from (C$_0$–C$_6$) alkyl, (C$_2$–C$_6$) alkenyl or (C$_2$–C$_6$)alkynyl and R$^8$ is substituted with:

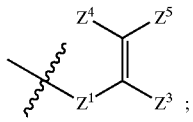

R$^9$ is selected from (C$_0$–C$_6$) alkyl or (C$_2$–C$_6$) alkenyl or alkynyl and R$^9$ is substituted with:

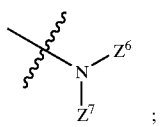

Z$^1$ is selected from the group consisting of O, S, and NR$^3$;

Z$^2$ is selected from the group consisting of H, C$_1$–C$_4$ alkyl, C$_3$–C$_6$ cycloalkyl, CN, CF$_3$, OR$^3$, heterocycle, NO$_2$, C(O)R$^3$, C(O)$_2$R$^3$, C(O)NR$^3$R$^4$, S(O)$_2$NR$^3$R$^4$, and S(O)$_2$R$^5$;

Z$^3$ is selected from the group consisting of OR$^3$, SR$^3$, and NR$^3$R$^4$;

Z$^4$ is selected from the group consisting of H, halo, C$_1$–C$_4$ alkyl, C$_3$–C$_6$ cycloalkyl, CN, CF$_3$, heterocycle, NO$_2$, C(O)R$^3$, C(O)$_2$R$^3$, C(O)NR$^3$R$^4$, S(O)$_2$NR$^3$R$^4$, and S(O)$_2$R$^5$;

Z$^5$ is selected from the group consisting of halo, CN, CF$_3$, heterocycle, NO$_2$, C(O)R$^3$, C(O)$_2$R$^3$, C(O)NR$^3$R$^4$, S(O)$_2$NR$^3$R$^4$, and S(O)$_2$R$^5$;

Z$^6$ is selected from the group consisting of H, C(O)H, C(O)R$^3$, C(O)OR$^4$, C(O)NR$^3$R$^4$, S(O)R$^5$ and S(O)$_2$R$^5$;

Z$^7$ is selected from OH, OR$^3$ and NR$^3$R$^4$,

R$^{10}$ is selected from hydrogen, (C$_1$–C$_4$) alkyl, (C$_2$–C$_4$) alkenyl or alkynyl, aryl, heterocyclic, and cycloalkyl, wherein said groups are substituted with 0–2 substituents independently selected from R$^{11}$ or R$^{12}$;

R$^{11}$ is selected from the group consisting of H, halogen, NO$_2$, CN, C$_1$–C$_4$alkyl, C$_3$–C$_{10}$ cycloalkyl, C$_2$–C$_6$ alkenyl, C$_2$–C$_6$alkynyl, haloalkyl, haloalkoxy, OH, C$_1$–C$_4$ alkoxy, C$_1$–C$_4$ alkylcarbonyl, NH$_2$, (C$_0$–C$_4$ alkyl)$_{0-2}$ alkylamino, C$_0$–C$_4$ alkylthio, C$_1$–C$_4$ alkylsulfonyl, aryl C$_0$–C$_4$ alkylsulfonyl, (C$_0$–C$_4$ alkyl)$_{0-2}$ alkylaminosulfonyl-, (C$_0$–C$_4$ alkylcarbonylaminosulfonyl-, arylC$_0$–C$_4$ alkylsulfonylaminocarbonyl, C$_1$–C$_4$ alkylsulfonylaminocarbonyl carboxylate, C$_1$–C$_4$ alkyloxycarbonyl, (C$_0$–$_4$ alkyl)$_{0-2}$ aminocarbonyl-, and (C$_0$–C$_4$ alkyl)tetrazol-5-yl;

R$^{12}$ is selected from H, alkyl, (C$_1$–C$_6$) alkyloxy, C$_3$–C$_6$ cycloalkyl, heterocyclic and aryl.

Compounds of formulas I and II, their enantiomers, diasteromers, tautomers and pharmaceutically acceptable salts, prodrugs and solvates thereof, are encompassed by the present invention and are novel.

The present invention also provides pharmaceutical compositions comprisingthe compounds of formulas I and II and methods of treating IMPDH-associated disorders using the compounds of formulas I and II.

The compounds of the present invention offer therapeutic advantages over known prior art compounds and are useful in treating IMPDH-associated disorders. These advantages include increased solubility (which in turn increases overall therapeutic benefit) and reduced negative side effects.

DETAILED DESCRIPTION OF THE INVENTION

According to a first embodiment of the present invention, compounds and pharmaceutically acceptable salts thereof are provided, said compounds represented by the following Formula I:

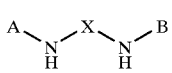

(I)

wherein:
X is selected from the group consisting of —C(O)—, —C(S)—, and —S(O)$_2$—;
A is a monocyclic or bicyclic ring system optionally comprising up to 4 heteroatoms selected from N, O, or S, and wherein a $CH_2$ adjacent to any of said N, O, or S, heteroatoms is optionally substituted with oxo (=O); and each ring is optionally substituted with up to 3 substituents, wherein:
the first of said substituents, if present, is selected from the group consisting of $R^1$, $R^2$, and $R^3$;
the second of said substituents, if present, is selected from the group consisting of $R^1$ and $R^2$; and
the third of said substituents, if present, is selected from the group consisting of $R^1$ and $R^2$;
$R^1$ is selected from a monocyclic ring system comprising 4 to 6 members per ring, wherein said ring system optionally comprises up to 4 heteroatoms selected from N, O, or S, and wherein a $CH_2$ adjacent to any of said N, O, or S heteroatoms is optionally substituted with oxo (=O); and each $R^1$ optionally comprises up to 3 substituents selected from $R^2$ or $R^3$;
$R^2$ is selected from halogen, CN, $NO_2$, $CF_3$, $(C_0-C_4$ alkyl)$OR^3$, $OCF_3$, $OC(O)R^3$, $OC(O)OR^3$, $O(C)NR^3R^4$, $(C_0-C_4$ alkyl)$C(O)R^3$, $(C_0-C_4$ alkyl)$C(O)OR^3$, $(C_0-C_4$ alkyl)$C(O)OR^3$, $(C_0-C_4$ alkyl)$C(O)NR^3R^4$, $(C_0-C_4$ alkyl)$CONR^3S(O)_2R^5$, $(C_0-C_4$ alkyl)$C(O)N(OR^3)R^3$, $(C_0-C_4$ alkyl)$SR^3$, $(C_0-C_4$ alkyl)$SR^3$, $(C_0-C_4$ alkyl)$S(O)R^5$, $(C_0-C_4$ alkyl)$S(O)_2R^5$, $(C_0-C_4$ alkyl)$S(O)R^5$, $(C_0-C_4$ alkyl)$S(O)_2R^5$, $(C_0-C_4$ alkyl)$S(O)_2NR^3R^4$, $(C_0-C_4$ alkyl)$S(O)_2NR^3C(O)R^4$, $(C_0-C_4$ alkyl)$NR^3R^4$, $(C_0-C_4$ alkyl)$NR^3C(O)NR^4$, $(C_0-C_4$ alkyl)$NR^3C(O)R^4$, $(C_0-C_4$ alkyl)$NR^3C(O)OR^5$, $(C_0-C_4$ alkyl)$NR^3S(O)_2R^5$, $(C_0-C_4$ alkyl)$S(O)_2OR^3$, $(C_0-C_4$ alkyl)$P(O)(OH)OR^3$, —J—$(C_0-C_4$ alkyl)$OR^3$, —J—$(C_1-C_4$ alkyl)$C(O)OR^3$, —J—$(C_1-C_4$ alkyl)$CONR^3S(O)_2R^5$, —J—$(C_1-C_4$ alkyl)$S(O)_2NR^3R^4$, —J—$(C_1-C_4$ alkyl)$S(O)_2NR^3C(O)R^4$, $(C_0-C_4$ alkyl)tetrazol-5-yl, and —J—$(C_1-C_4$ alkyl)tetrazol-5-yl, wherein J is chosen from O, S, and $NR^3$;
$R^3$ is selected from hydrogen, $(C_1-C_4)$ alkyl, $(C_2-C_4)$ alkenyl or $(C_2-C_4)$alkynyl, aryl$(C_0-C_4)$ alkyl-, heterocyclic$(C_0-C_4)$ alkyl- and cycloalkyl$(C_0-C_4)$ alkyl-, wherein said groups are substituted with 0–2 substituents independently selected from $R^6$;
$R^4$ is selected from hydrogen, $(C_1-C_4)$ alkyl, $(C_2-C_4)$-alkenyl, $(C_2-C_4)$alkynyl, aryl$(C_0-C_4)$alkyl-, heterocyclic$(C_0-C_4)$alkyl-, cycloalkyl$(C_0-C_4)$ alkyl-, $(C_0-C_4)$alkylcarbonyl, aryl$(C_0-C_4)$ alkylcarbonyl, heterocyclic$(C_0-C_4)$alkylcarbonyl, $(C_1-C_4)$alkyloxycarbonyl, aryl$(C_1-C_4)$ alkyloxycarbonyl, and heterocyclic$(C_1-C_4)$ alkyloxycarbonyl, wherein said groups are substituted with 0–2 substituents independently selected from $R^6$;
alternatively, $R^3$ and $R^4$, when both substituents are on the same nitrogen atom, as in (—$NR^3R^4$), can be taken together with the nitrogen atom to which they are attached to form a heterocycle selected from the group consisting of 1-aziridinyl, 1-azetidinyl, 1-piperidinyl, 1-morpholinyl, 1-pyrrolidinyl, thiamorpholinyl, thiazolidinyl, and 1-piperazinyl, said heterocycle being optionally substituted with 0–3 groups selected from the group consisting of oxo, $R^6$, $C_1-C_6$ alkyl, $C_3-C_7$ cycloalkyl$(C_0-C_4$ alkyl)-, $C_1-C_6$ alkylcarbonyl, $C_3-C_7$ cycloalkyl $(C_0-C_5$ alkyl)carbonyl, $C_1-C_6$ alkoxycarbonyl, $C_3-C_7$ cycloalkyl$(C_0-C_5$ alkoxy)carbonyl, aryl $(C_0-C_5$ alkyl), heterocyclic$(C_0-C_5$ alkyl), aryl $(C_1-C_5$ alkoxy)carbonyl, heterocyclic$(C_1-C_5$ alkoxy)carbonyl, $C_1-C_6$ alkylsulfonyl, arylsulfonyl, and heterocyclicsulfonyl,
wherein said aryl or heterocyclic groups are substituted with 0–2 substituents independently selected from the group consisting of $C_1-C_4$ alkyl, $C_1-C_4$ alkoxy, F, Cl, Br, $CF_3$, CN, and $NO_2$;
$R^5$ is selected from $(C_1-C_4)$ alkyl, $(C_2-C_4)$ alkenyl, $(C_2-C_4)$alkynyl, aryl$(C_0-C_4)$ alkyl-, heterocyclic $(C_0-C_4)$ alkyl-, and cycloalkyl$(C_0-C_4)$ alkyl-, and each $R^5$ optionally comprises up to 2 different or identical substituents selected from $R^6$;
$R^6$ is selected from H, halogen, $NO_2$, CN, $C_1-C_4$alkyl, $C_3-C_{10}$ cycloalkyl, $C_2-C_6$ alkenyl, $C_2-C_6$alkynyl, haloalkyl, haloalkoxy, OH, hydroxy $C_1-C_4$ alkyl, $C_1-C_4$ alkoxy, $C_1-C_4$ alkylcarbonyl, $NH_2$, $(C_0-C_4$ alkyl)$_{0-2}$ alkylamino, $C_0-C_4$ alkylthio, $C_1-C_4$ alkylsulfonyl, aryl $C_0-C_4$ alkylsulfonyl, $(C_0-C_4$ alkyl)$_{0-2}$ alkylaminosulfonyl-, $(C_0-C_4$ alkylcarbonylarninosulfonyl-, aryl$C_0-C_4$ alkylsulfonylaminocarbonyl, $C_1-C_4$ alkylsulfonylaminocarbonyl carboxylate, $C_1-C_4$ alkyloxycarbonyl, $(C_0-C_4$ alkyl)$_{0-2}$ aminocarbonyl-, and $(C_0-C_4$ alkyl)tetrazol-5-yl;
B is a monocyclic or bicyclic ring system optionally comprising up to 4 heteroatoms selected from N, O, or S, and wherein a $CH_2$ adjacent to any of said N, O, or S heteroatoms is optionally substituted with oxo (=O); wherein each ring system is substituted with one substituent selected from $R^7$, $R^8$ or $R^9$, and is optionally substituted with a second and/or a third substituent, wherein:
the second of said substituents, if present, is selected from $R^7$, $R^8$, $R^9$, $R^{10}$, $R^{11}$, $R^{12}$; and
the third of said substituents, if present is selected from $R^{10}$, $R^{11}$, and $R^{12}$; $R^7$ is selected from $(C_0-C_6)$ alkyl, $(C_2-C_6)$ alkenyl or $(C_2-C_6)$ alkynyl and $R^7$ is substituted with:

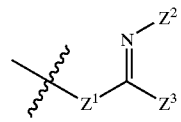

$R^8$ is selected from $(C_0-C_6)$ alkyl, $(C_2-C_6)$ alkenyl or $(C_2-C_6)$alkynyl and $R^8$ is substituted with:

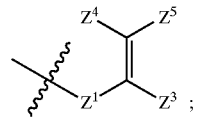

$R^9$ is selected from $(C_0-C_6)$-alkyl or $(C_2-C_6)$-alkenyl or $(C_2-C_6)$alkynyl and $R^9$ is substituted with:

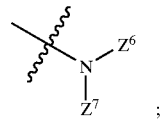

$Z^1$ is selected from the group consisting of O, S, and $NR^3$;
$Z^2$ is selected from the group consisting of H, $C_1-C_4$ alkyl, $C_3-C_6$ cycloalkyl, CN, $CF_3$, $OR^3$, heterocycle, $NO_2$, $C(O)R^3$, $C(O)_2R^3$, $C(O)NR^3R^4$, $S(O)_2NR^3R^4$, and $S(O)_2R^5$;

$Z^3$ is selected from the group consisting of $OR^3$, $SR^3$, and $NR^3R^4$;

$Z^4$ is selected from the group consisting of H, halo, $C_1$–$C_4$ alkyl, $C_3$–$C_6$ cycloalkyl, CN, $CF_3$, heterocycle, $NO_2$, $C(O)R^3$, $C(O)_2R^3$, $C(O)NR^3R^4$, $S(O)_2NR^3R^4$, and $S(O)_2R^5$;

$Z^5$ is selected from the group consisting of halo, CN, $CF_3$, heterocycle, $NO_2$, $C(O)R^3$, $C(O)_2R^3$, $C(O)NR^3R^4$, $S(O)_2NR^3R^4$, and $S(O)_2R^5$;

$Z^6$ is selected from the group consisting of H, $C(O)H$, $C(O)R^3$, $C(O)OR^5$, $C(O)NR^3R^4$, $S(O)R^5$ and $S(O)_2R^5$;

$Z^7$ is selected from the group consisting of OH, $OR^3$ and $NR^3R^4$, $R^{10}$ is selected from hydrogen, ($C_1$–$C_4$) alkyl, ($C_2$–$C_4$) alkenyl or alkynyl, aryl, heterocyclic, and cycloalkyl, and each $R^{10}$ optionally comprises up to 3 substituents selected from $R^{11}$ or $R^{12}$;

$R^{11}$ is selected from the group consisting of H, halogen, $NO_2$, CN, $C_1$–$C_4$alkyl, $C_3$–$C_{10}$ cycloalkyl, $C_2$–$C_6$ alkenyl, $C_2$–$C_6$alkynyl, haloalkyl, haloalkoxy, OH, $C_1$–$C_4$ alkoxy, $C_1$–$C_4$ alkylcarbonyl, $NH_2$, ($C_0$–$C_4$ alkyl)$_{0-2}$ alkylamino, $C_0$–$C_4$ alkylthio, $C_1$–$C_4$ alkylsulfonyl, aryl $C_0$–$C_4$ alkylsulfonyl, ($C_0$–$C_4$ alkyl)$_{0-2}$ alkylaminosulfonyl-, ($C_0$–$C_4$ alkylcarbonylaminosulfonyl-, aryl$C_0$–$C_4$ alkylsulfonylaminocarbonyl, $C_1$–$C_4$ alkylsulfonylaminocarbonyl carboxylate, $C_1$–$C_4$ alkyloxycarbonyl, ($C_0$–$C_4$ alkyl)$_{0-2}$ aminocarbonyl-, and ($C_0$–$C_4$ alkyl)tetrazol-5-yl;

$R^{12}$ is selected from H, alkyl, ($C_1$–$C_6$) alkyloxy, $C_3$–$C_6$ cycloalkyl, heterocycle and aryl.

Preferred are compounds of Formula I, including stereoisomeric forms thereof, tautomeric forms thereof, pharmaceutically acceptable salt forms thereof, or prodrug forms thereof, wherein:

A is a monocyclic ring system optionally comprising up to 3 heteroatoms selected from N, O, or S, and wherein a $CH_2$ adjacent to any of said N, O, or S, heteroatoms is optionally substituted with oxo (=O); and is substituted with 1 to 3 substituents, wherein:
the first of said substituents is selected from the group consisting of $R^1$, $R^2$, and $R^3$;
the second of said substituents, if present, is selected from the group consisting of $R^1$ and $R^2$; and
the third of said substituents, if present, is selected from the group consisting of $R^1$ and $R^2$;

B is a monocyclic or bicyclic ring system optionally comprising up to 4 heteroatoms selected from N, O, or S, and wherein a $CH_2$ adjacent to any of said N, O, or S heteroatoms is optionally substituted with oxo (=O); wherein each ring system is substituted with one substituent selected from $R^7$, $R^8$ or $R^9$, and is optionally substituted with a second and/or a third substituent, wherein:
the second of said substituents, if present, is selected from $R^{10}$, $R^{11}$, $R^{12}$; and
the third of said substituents, if present is selected from $R^{10}$, $R^{11}$, and $R^{12}$;

$Z^2$ is selected from the group consisting of CN, $CF_3$, $OR^3$, heterocycle, $C(O)R^3$, $C(O)_2R^3$, $C(O)NR^3R^4$, $S(O)_2NR^3R^4$, and $S(O)_2R^5$;

$Z^4$ is selected from the group consisting of halo, CN, $CF_3$, heterocycle, $NO_2$, $C(O)R^3$, $C(O)_2R^3$, $C(O)NR^3R^4$, $S(O)_2NR^3R^4$, and $S(O)_2R^5$;

and all other constituents are as previously described for compounds for Formula I.

Particularly preferred are compounds of the Formula I represented by the following Formula IA, including stereoisomeric forms thereof, tautomeric forms thereof, pharmaceutically acceptable salt forms thereof, or prodrug forms thereof:

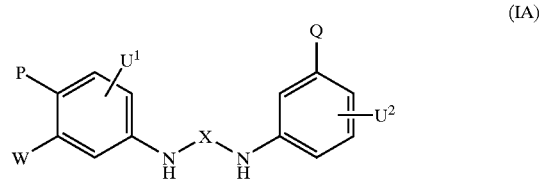

(IA)

wherein Q is selected from the group consisting of $R^7$, $R^8$, and $R^9$ and wherein P is selected from the group consisting of $R^1$ or $R^2$ and wherein W and $U^1$ are selected from the group consisting of $R^2$ or $R^3$ and wherein $U^2$ is selected from $R^{10}$ or $R^{11}$;

$Z^2$ is selected from the group consisting of CN, $CF_3$, $OR^3$, heterocycle, $C(O)R^3$, $C(O)_2R^3$, $C(O)NR^3R^4$, $S(O)_2NR^3R^4$, and $S(O)_2R^5$;

$Z^4$ is selected from the group consisting of halo, CN, $CF_3$, heterocycle, $NO_2$, $C(O)R^3$, $C(O)_2R^3$, $C(O)NR^3R^4$, $S(O)_2NR^3R^4$, and $S(O)_2R^5$.

and all other constituents are as previously described for compounds of Formula I.

A second embodiment of the present invention encompasses compounds and pharmaceutically acceptable salts thereof represented by the following Formula II:

(II)

wherein:
V is —C($NZ^2$)— or —C($CZ^9Z^{10}$)—;
$Z^2$ is selected from the group consisting of lower alkyl, cycloalkyl, CN, $CF_3$, heterocycle, $NO_2$, $C(O)R^3$, $C(O)_2R^3$, $C(O)NR^3R^4$, $S(O)_2NR^3R^4$, and $S(O)_2R^5$;
$Z^9$ is selected the group consisting of H, lower alkyl, cycloalkyl, CN, $CF_3$, heterocycle, $NO_2$, $C(O)R^3$, $C(O)_2R^4$, $C(O)NR^3R^4$, $S(O)_2NR^3R^4$, and $S(O)_2R^5$;
$Z^{10}$ is selected the group consisting of CN, $CF_3$, heterocycle, $NO_2$, $C(O)R^3$, $C(O)_2R^3$, $C(O)NR^3R^4$, $S(O)_2NR^3R^4$, and $S(O)_2R^5$;

A is 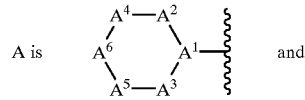 and $A^1$ is C or $CS^1$;
$A^2$ is selected from the group consisting of
1) a heteroatom selected from the group consisting of nitrogen, oxygen and sulfur,
2) $CS^2$,
3) CO,
4) $NS^7$,
5) $S(O)_2$;
$A^3$ is selected from the group consisting of
1) a heteroatom selected from the group consisting of nitrogen, oxygen and sulfur,
2) $CS^3$,
3) CO,

4) $NS^7$,
5) $S(O)_2$;

$A^4$ is selected from the group consisting of
1) a heteroatom selected from the group consisting of nitrogen, oxygen and sulfur,
2) $CS^4$,
3) CO,
4) $NS^7$,
5) $S(O)_2$,
6) a bond;

$A^5$ is selected from the group consisting of
1) a heteroatom selected from the group consisting of nitrogen, oxygen and sulfur,
2) $CS^5$,
3) CO,
4) $NS^7$,
5) $S(O)_2$;

$A^6$ is selected from the group consisting of
1) a heteroatom selected from the group consisting of nitrogen, oxygen and sulfur,
2) $CS^6$,
3) CO,
4) $NS^7$,
5) $S(O)_2$;

$A^4$, $A^6$ and the atoms to which they are attached together may form a bicyclic ring system containing 0–2 additional heteroatoms selected from nitrogen, oxygen and sulphur;

$A^5$, $A^6$ and the atoms to which they are attached together may form a bicyclic ring system containing 0–2 additional heteroatoms selected from nitrogen, oxygen and sulphur;

Wherein, $A^2$, $A^3$, $A^4$, $A^5$, and $A^6$, are chosen such that the total number of heteroatoms in the monocyclic or bicyclic ring system does not exceed four, and the attached substituents $S^1$, $S^2$, $S^3$, $S^4$, $S^5$, $S^6$, and $S^7$ are chosen such that the total number of non-hydrogen substituents does not exceed four;

$S^1$ is selected from H, $C_1$–$C_3$ alkyl and halo;
$S^2$ is selected from H, $C_1$–$C_3$ alkyl and halo;
$S^3$ is selected from H, $C_1$–$C_3$ alkyl and halo;
$S^4$ is selected from H, $R^1$, $R^2$ or $R^3$;
$S^5$ is selected from H, $R^1$, $R^2$ or $R^3$;
$S^6$ is selected from $R^1$, $R^2$ or $R^5$;
$S^7$ is selected from $R^3$, or $R^4$;

$R^1$ is a monocyclic ring system comprising 4 to 6 members per ring, wherein said ring system optionally comprises up to 4 heteroatoms selected from N, O, or S, and wherein a $CH_2$ adjacent to any of said N, O, or S heteroatoms is optionally substituted with oxo (=O); and each $R^1$ optionally comprises up to 3 substituents selected from $R^2$ or $R^3$;

$R^2$ is selected from halogen, CN, $NO_2$, $CF_3$, ($C_0$–$C_4$ alkyl)$OR^3$, $OCF_3$, $OC(O)R^3$, $OC(O)OR^3$, $O(C)NR^3R^4$, ($C_0$–$C_4$ alkyl)C(O)$R^3$, ($C_0$–$C_4$ alkyl)C(O)$OR^3$, ($C_0$–$C_4$ alkyl)C(O)$NR^3R^4$, ($C_0$–$C_4$ alkyl)CONR$^3$S(O)$_2R^5$, ($C_0$–$C_4$ alkyl)C(O)N(OR$^3$)$R^3$, ($C_0$–$C_4$ alkyl)$SR^3$, ($C_0$–$C_4$ alkyl)$SR^3$, ($C_0$–$C_4$ alkyl)S(O)$R^5$, ($C_0$–$C_4$ alkyl)S(O)$_2R^5$, ($C_0$–$C_4$ alkyl)S(O)$_2R^5$, ($C_0$–$C_4$ alkyl)S(O)$_2NR^3R^4$, ($C_0$–$C_4$ alkyl)S(O)$_2NR^3C(O)R^4$, ($C_0$–$C_4$ alkyl)NR$^3R^4$, ($C_0$–$C_4$ alkyl)NR$^3$C(O)$NR^4$, ($C_0$–$C_4$ alkyl)NR$^3$C(O)$R^4$, ($C_0$–$C_4$ alkyl)NR$^3$C(O)$OR^5$, ($C_1$–$C_4$ alkyl)NR$^3$C(O)$NR_3R^{5a}$, ($C_0$–$C_4$ alkyl)NR$^3$S(O)$_2R^5$, ($C_0$–$C_4$ alkyl)S(O)$_2OR^3$, ($C_0$–$C_4$ alkyl)P(O)(OH)$OR^3$, —J—($C_0$–$C_4$ alkyl)$OR^3$, —J—($C_1$–$C_4$ alkyl)C(O)$OR^3$, —J—($C_1$–$C_4$ alkyl)CONR$^3$S(O)$_2R^5$, —J—($C_1$–$C_4$ alkyl)S(O)$_2NR^3R^4$, —J—($C_1$–$C_4$ alkyl)S(O)$_2NR^3C(O)R^4$, ($C_0$–$C_4$ alkyl)tetrazol-5-yl, and —J—($C_1$–$C_4$ alkyl)tetrazol-5-yl, wherein J is chosen from O, S, and $NR^3$;

$R^3$ is selected from hydrogen, ($C_1$–$C_4$) alkyl, ($C_2$–$C_4$) alkenyl, ($C_2$–$C_4$)alkynyl, aryl($C_0$–$C_4$) alkyl-, heterocyclic($C_0$–$C_4$) alkyl-, and cycloalkyl($C_0$–$C_4$) alkyl-, wherein said groups are substituted with 0–2 substituents independently selected from $R^6$;

$R^4$ is selected from hydrogen, ($C_1$–$C_4$) alkyl, ($C_2$–$C_4$)-alkenyl, ($C_2$–$C_4$)alkynyl, aryl($C_0$–$C_4$)alkyl-, heterocyclic($C_0$–$C_4$)alkyl-, cycloalkyl, ($C_0$–$C_4$) alkylcarbonyl, aryl($C_0$–$C_4$)alkylcarbonyl, heterocyclic($C_0$–$C_4$)alkylcarbonyl, ($C_1$–$C_4$) alkyloxycarbonyl, aryl($C_1$–$C_4$)alkyloxycarbonyl, and heterocyclic($C_1$–$C_4$)alkyloxycarbonyl, wherein said groups are substituted with 0–2 substituents independently selected from $R^6$;

alternatively, $R^3$ and $R^4$, when both substituents are on the same nitrogen atom, as in (—$NR^3R^4$), can be taken together with the nitrogen atom to which they are attached to form a heterocycle selected from the group consisting of 1-aziridinyl, 1-azetidinyl, 1-piperidinyl, 1-morpholinyl, 1-pyrrolidinyl, thiamorpholinyl, thiazolidinyl, and 1-piperazinyl, said heterocycle being optionally substituted with 0–3 groups selected from the group consisting of oxo, $R^6$, $C_1$–$C_6$ alkyl, $C_3$–$C_7$ cycloalkyl($C_0$–$C_4$ alkyl)-, $C_1$–$C_6$ alkylcarbonyl, $C_3$–$C_7$ cycloalkyl ($C_0$–$C_5$ alkyl)carbonyl, $C_1$–$C_6$ alkoxycarbonyl, $C_3$–$C_7$ cycloalkyl($C_0$–$C_5$ alkoxy)carbonyl, aryl ($C_0$–$C_5$ alkyl), heterocyclic($C_0$–$C_5$ alkyl), aryl ($C_1$–$C_5$ alkoxy)carbonyl, heterocyclic($C_1$–$C_5$ alkoxy)carbonyl, $C_1$–$C_6$ alkylsulfonyl, arylsulfonyl, and heterocyclicsulfonyl, wherein said aryl or heterocyclic groups are substituted with 0–2 substituents independently selected from the group consisting of $C_1$–$C_4$ alkyl, $C_1$–$C_4$ alkoxy, F, Cl, Br, $CF_3$, CN, and $NO_2$;

$R^5$ is selected from ($C_1$–$C_4$)alkyl, ($C_2$–$C_4$)alkenyl, ($C_2$–$C_4$)alkynyl, aryl($C_0$–$C_4$) alkyl-, heterocyclic ($C_0$–$C_4$) alkyl-, or cycloalkyl($C_0$–$C_4$) alkyl-, and each $R^3$ optionally comprises up to 2 different or identical substituents selected from $R^6$;

$R^{5a}$ is selected from ($C_1$–$C_4$)alkyl, ($C_2$–$C_4$)alkenyl, ($C_2$–$C_4$)alkynyl, aryl($C_1$–$C_4$) alkyl-, heterocyclic ($C_1$–$C_4$) alkyl-, or cycloalkyl($C_1$–$C_4$) alkyl-, and each $R^3$ optionally comprises up to 2 different or identical substituents selected from $R^6$;

$R^6$ is selected from H, halogen, $NO_2$, CN, $C_1$–$C_4$alkyl, $C_3$–$C_{10}$ cycloalkyl, $C_2$–$C_6$ alkenyl, $C_1$–$C_6$alkynyl, haloalkyl, haloalkoxy, OH, hydroxy $C_1$–$C_4$ alkyl, $C_1$–$C_4$ alkoxy, $C_1$–$C_4$ alkylcarbonyl, $NH_2$, ($C_0$–$C_4$ alkyl)$_{0-2}$ alkylamino, $C_1$–$C_4$ alkylthio, $C_1$–$C_4$ alkylsulfonyl, aryl $C_1$–$C_4$ alkylsulfonyl, ($C_1$–$C_4$ alkyl)$_2$ alkylaminosulfonyl-, ($C_1$–$C_4$ alkylcarbonylaminosulfonyl-, aryl$C_0$–$C_4$ alkylsulfonylaminocarbonyl, $C_1$–$C_4$ alkylsulfonylaminocarbonyl carboxylate, $C_1$–$C_4$ alkyloxycarbonyl, ($C_1$–$C_4$ alkyl)$_{0-2}$ aminocarbonyl-, and ($C_0$–$C_4$ alkyl)tetrazol-5-yl;

M is selected from the group consisting of:
(i) ($C_1$–$C_6$)alkyl, ($C_2$–$C_6$)alkenyl, ($C_2$–$C_6$)alkynyl, and cycloalkyl($C_1$–$C_4$)alkyl, optionally comprising up to 3 substituents selected from the group consisting of $R^1$, $R^2$, or $R^4$, wherein any $CH_2$ is optionally substituted with oxo (=O); and (ii)

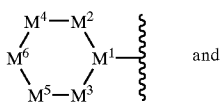 and $M^1$ is C or $CP^1$;
$M^2$ is selected from the group consisting of
1) a heteroatom selected from the group consisting of nitrogen, oxygen and sulfur,
2) $C(P^2)_{1-2}$,
3) CO,
4) $NP^7$,
5) $S(O)_2$;
$M^3$ is selected from the group consisting of
1) a heteroatom selected from the group consisting of nitrogen, oxygen and sulfur,
2) $C(P^3)_{1-2}$,
3) CO,
4) $NP^7$,
5) $S(O)_2$;
$M^4$ is selected from the group consisting of
1) a heteroatom selected from the group consisting of nitrogen, oxygen and sulfur,
2) $CP^4$,
3) $CP^5$,
4) $C(P^5)_{1-2}$,
5) CO,
6) $NP^7$,
7) $S(O)_2$;
$M^5$ is selected from the group consisting of
1) a heteroatom selected from the group consisting of nitrogen, oxygen and sulfur,
2) $C(P^5)_{1-2}$,
3) CO,
4) $NP^7$,
5) $S(O)_2$;
$M^6$ is selected from the group consisting of
1) a heteroatom selected from the group consisting of nitrogen, oxygen and sulfur,
2) $C(P^6)_{1-2}$,
3) CO,
4) $NP^7$,
5) $S(O)_2$,
6) a bond;
$M^4$, $M^6$ and the atoms to which they are attached together may form a bicyclic ring system containing 0–2 additional heteroatoms selected from nitrogen, oxygen and sulphur;
$M^4$, $M^6$ and the atoms to which they are attached together may form a bicyclic ring system containing 0–2 additional heteroatoms selected from nitrogen, oxygen and sulphur;
Wherein, $M^2$, $M^3$, $M^4$, $M^5$, and $M^6$, are chosen such that the total number of heteroatoms in the monocyclic or bicyclic ring system does not exceed four, and the attached substituents $P^1$, $P^2$, $P^3$, $P^4$, $P^5$, $P^6$, and $P^7$ are chosen such that the total number of non-hydrogen substituents does not exceed four;
$P^1$ is selected from H, $C_1$–$C_3$ alkyl or halo;
$P^2$ is selected from H, $C_1$–$C_3$ alkyl or halo;
$P^3$ is selected from H, $C_1$–$C_3$ alkyl or halo;
$P^4$ is selected from $R^2$, $R^5$, $R^7$, $R^8$ or $R^9$;
$P^5$ is selected from H, $R^2$ or $R^3$;
$P^6$ is selected from H, $R^2$, $R^3$, $R^4$, $R^7$, $R^8$ or $R^9$;
$P^7$ is selected from $R^3$ or $R^4$;
$R^7$ is selected from $(C_1-C_)$ alkyl, $(C_2-C_)$ alkenyl or $(C_2-C_6)$alkynyl and $R^7$ is substituted with:

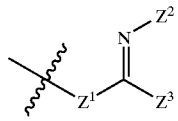

$R^8$ is elected from $(C_0-C_6)$ alkyl, $(C_2-C_6)$ alkenyl or $(C_2-C_6)$alkynyl and $R^8$ is substituted with:

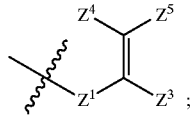

$R^9$ is selected from $(C_1-C_6)$ alkyl or $(C_1-C_6)$ alkenyl or alkynyl and $R^1$ is substituted with:

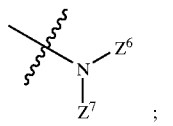

$Z^1$ is selected from the group consisting of O, S, and $NR^3$;
$Z^2$ is selected from the group consisting of H, $C_1$–$C_4$ alkyl, $C_3$–$C_6$ cycloalkyl, CN, $CF_3$, $OR^3$, heterocycle, $NO_2$, $C(O)R^3$, $C(O)_2R^3$, $C(O)NR^3R^4$, $S(O)_2NR^3R^4$, and $S(O)_2R^5$;
$Z^3$ is selected from the group consisting of $OR^3$, $SR^3$, and $NR^3R^4$;
$Z^4$ is selected from the group consisting of H, halo, $C_1$–$C_4$ alkyl, $C_3$–$C_6$ cycloalkyl, CN, $CF_3$, heterocycle, $NO_2$, $C(O)R^3$, $C(O)_2R^3$, $C(O)NR^3R^4$, $S(O)_2NR^3R^4$, and $S(O)_2R^5$;
$Z^5$ is selected from the group consisting of halo, CN, $CF_3$, heterocycle, $NO_2$, $C(O)R^3$, $C(O)_2R^3$, $C(O)NR^3R^4$, $S(O)_2NR^3R^4$, and $S(O)_2R^5$;
$Z^6$ is selected from the group consisting of H, $C(O)H$, $C(O)R^3$, $C(O)OR^4$, $C(O)NR^3R^4$, $S(O)R^5$ and $S(O)_2R^5$;
$Z^7$ is selected from the group consisting of OH, $OR^3$ and $NR^3R^4$,
$R^{10}$ is selected from hydrogen, $(C_1-C_4)$ alkyl, $(C_2-C_4)$ alkenyl or alkynyl, aryl, heterocyclic, and cycloalkyl, wherein said groups are substituted with 0–2 substituents independently selected from $R^{11}$ or $R^{12}$;
$R^{11}$ is selected from the group consisting of H, halogen, $NO_2$, CN, $C_1$–$C_4$alkyl, $C_3$–$C_{10}$ cycloalkyl, $C_2$–$C_6$ alkenyl, $C_2$–$C_6$alkynyl, haloalkyl, haloalkoxy, OH, $C_1$–$C_4$ alkoxy, $C_1$–$C_4$ alkylcarbonyl, $NH_2$, $(C_0$–$C_4$ alkyl$)_{0-2}$ alkylamino, $C_1$–$C_4$ alkylthio, $C_1$–$C_4$ alkylsulfonyl, aryl $C_0$–$C_4$ alkylsulfonyl, $(C_0$–$C_4$ alkyl$)_{0-2}$ alkylaminosulfonyl-, $(C_0$–$C_4$ alkyl$)$carbonylaminosulfonyl-, aryl$C_0$–$C_4$ alkylsulfonylaminocarbonyl, $C_1$–$C_4$ alkylsulfonylaminocarbonyl carboxylate, $C_1$–$C_4$ alkyloxycarbonyl, $(C_0$–$C_4$ alkyl$)_{0-2}$ aminocarbonyl-, and $(C_1$–$C_4$ alkyl$)$tetrazol-5-yl;
$R^{12}$ is selected from H, alkyl, $(C_1-C_6)$ alkyloxy, $C_3$–$C_6$ cycloalkyl, heterocyclic and aryl.

Preferred are compounds of Formula II, including stereoisomeric forms thereof, tautomeric forms thereof, pharmaceutically acceptable salt forms thereof, or prodrug forms thereof, wherein:

$Z^2$ is selected from the group consisting of CN, $CF_3$, heterocycle, $C(O)R^3$, $C(O)_2R^3$, $C(O)NR^3R^4$, $S(O)_2NR^3R^4$, and $S(O)_2R^5$;

$Z^9$ is selected the group consisting of H, lower alkyl, cycloalkyl, CN, $CF_3$, heterocycle, $C(O)R^3$, $C(O)_2R^3$, $C(O)NR^3R^4$, $S(O)_2NR^3R^4$, and $S(O)_2R^5$;

$Z^{10}$ is selected the group consisting of CN, $CF_3$, heterocycle, $C(O)R^3$, $C(O)_2R^3$, $C(O)NR^3R^4$ $S(O)_2NR^3R^4$, and $S(O)_2R^5$;

$A^1$ is C;

$M^4$ is selected from the group consisting of
1) a heteroatom selected from the group consisting of nitrogen, oxygen and sulfur,
2) $CP^4$,
3) $C(P^5)_{1-2}$,
4) CO,
5) $NP^7$,
6) $S(O)_2$;

and all other constituents are as previously described for compounds of Formula II.

Particularly preferred are compounds of Formula II represented by the following Formula IIA, including stereoisomeric forms thereof, tautomeric forms thereof, pharmaceutically acceptable salt forms thereof, or prodrug forms thereof,

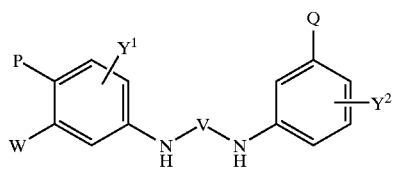

(IIA)

wherein Q is selected from the group consisting of $R^2$, $R^7$, $R^8$, and $R^9$;

P is selected from the group consisting of $R^1$ and $R^2$;

W and $Y^1$ are independently selected from the group consisting of $R^2$ and $R^3$;

$Y^2$ is selected from $R^{10}$ and $R^{11}$;

$Z^2$ is selected from the group consisting of CN, $CF_3$, heterocycle, $C(O)R^3$, $C(O)_2R^3$, $C(O)NR^3R^4$, $S(O)_2NR^3R^4$, and $S(O)_2R^5$;

$Z^9$ is selected the group consisting of H, lower alkyl, cycloalkyl, CN, $CF_3$, heterocycle, $C(O)R^3$, $C(O)_2R^3$, $C(O)NR^3R^4$, $S(O)_2NR^3R^4$, and $S(O)_2$ $Z^{10}$ is selected the group consisting of CN, $CF_3$, heterocycle, $C(O)R^3$, $C(O)_2R^3$, $C(O)NR^3R^4$, $S(O)_2NR^3R^4$, and $S(O)_2R^5$;

and all other constituents are as previously described for compounds of Formula II.

According to another embodiment, the invention provides pharmaceutical compositions comprising a compound of formula I, IA, II, or IIA, as described above.

According to another embodiment, the invention provides methods of inhibiting IMPDH activity in mammals by administering a compound of formula I, IA, II, or IIA, as described above.

According to another embodiment, the invention provides methods of treating IMPDH-associated disorders in a mammal comprising administering at least one compound of formula I, IA, II, or IIA as described above.

All references cited herein are incorporated by reference in their entirety.

In the description above and elsewhere in the specification, including the claims, each occurrence of a particular constituent is independent of each other occurrence of that same constituent.

Listed below are definitions of various terms used in the specification and claims to describe the present invention.

The term "alkyl" refers to straight or branched chain alkyl.

The term "$C_{integer}$-$C_{integer}$" refers to a variable number of carbon atoms in a group depending on the integer values, as in $C_0$–$C_4$alkyl, which is meant to indicate a straight or branched alkyl group containing 0–4 carbon atoms. A group with 0 (zero) carbon atoms indicates that the carbon atom is absent i.e. there is a direct bond connecting adjacent terms. For example the term "$C_0$–$C_4$ alkylhydroxy" in the case "$C_0$" is meant to indicate the group hydroxy.

The term "halogen" or "halo" refers to fluorine, chlorine, bromine or iodine.

The term "aryl" refers to monocyclic or bicyclic aromatic hydrocarbons having 6 to 12 carbon atoms in the ring portion, such as phenyl, naphthyl, biphenyl and diphenyl groups which may be optionally substituted.

The term "alkenyl" refers to straight or branched chain alkenyl groups.

The term "alkynyl" refers to straight or branched chain alkynyl.

The term "cycloalkyl" refers to an optionally substituted, saturated cyclic hydrocarbon ring system.

The terms "monocyclic" and "bicyclic" may be used with reference to either a "carbocyclic" or a "heterocyclic" ring system and mean, respectively, a single ring and two rings that are fused, bridged, or attached in a spiro fashion.

The term "carbocyclic" refers to an optionally substituted, fully saturated or unsaturated, aromatic or nonaromatic cyclic group, which is a 3 to 7 membered monocyclic, or a 7 to 11 membered bicyclic group, and all the atoms in the ring(s) are carbon atoms. Exemplary groups include phenyl, naphthyl, anthracenyl, cyclohexyl, cyclohexenyl, indanyl, bicyclo[2,21]heptane, and the like.

The terms "heterocycle" and "heterocyclic" refer to an optionally substituted, fully saturated or unsaturated, aromatic or nonaromatic cyclic group, which is a 3 to 7 membered monocyclic, or a 7 to 11 membered bicyclic, which have at least one heteroatom and at least one carbon atom in the ring. Each heterocyclic ring may contain 1, 2, 3, or 4 heteroatoms selected from nitrogen, oxygen and sulfur, where the nitrogen and sulfur heteroatoms may also optionally be oxidized and the nitrogen heteroatoms may also optionally be quaternized. The heterocyclic group may be attached via a nitrogen or carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furanyl, tetrahydrofuranyl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydrothiopyranyl, tetrahydropyranyl, morpholinyl, thiamorpholinyl, thiamorpholinyl sulfoxide, tetrahydrothiopyranylsulfone, thiamorpholinyl sulfone, 1,3-dioxolane, tetrahydro-1,1-dioxothienyl, dioxanyl, isothiazolidinyl, thietanyl, thiiranyl, triazinyl, triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuranyl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), pyrrolo[1,2-a]pyridinyl, 1,3-dioxindanyl, dihydroisoindolyl, dihydroquinazolinyl (such as 3,4-dihydro-4-oxo-quinazolinyl), benzisothiazolyl, benzisoxazolyl, benzodiazinyl, benzothiopyranyl, benzotriazolyl, benzpyrazolyl, dihydrobenzofuranyl, dihydrobenzothienyl, dihydrobenzothiopyranyl, dihydrobenzothiopyranyl sulfone, dihydrobenzopyranyl, indolinyl, indolyl, isochromanyl, isoindolinyl, naphthyridinyl, phthalazinyl, piperonyl, purinyl, pyridopyridyl, quinazolinyl, tetrahydroquinolinyl, thienofuiryl, thienopyridyl, thienothienyl, and the like.

"IMPDH-associated disorders" refers to any disorder or disease state in which inhibition of the enzyme IMPDH (inosine monophosphate dehydrogenase, EC1.1.1.205, of which there are presently two known isozymes referred to as IMPDH type 1 and IMPDH type 2) would modulate the activity of cells (such as lymphocytes or other cells) and thereby ameliorate or reduce the symptoms or modify the underlying cause(s) of that disorder or disease. There may or may not be present in the disorder or disease an abnormality associated directly with the IMPDH enzyme.

Examples of IMPDH-associated disorders include transplant rejection and autoimmune disorders, such as rheumatoid arthritis, multiple sclerosis, juvenile diabetes, asthma, and inflammatory bowel disease, as well as inflammatory disorders, cancer and tumor disorders, T-cell mediated hypersensitivity diseases, ischemic or reperfusion injury, viral replication diseases, proliferative disorders and vascular diseases.

As used herein the term "treating" includes prophylactic and therapeutic uses, and refers to the alleviation of symptoms of a particular disorder in a patient, the improvement of an ascertainable measurement associated with a particular disorder, or the prevention of a particular immune response (such as transplant rejection). The term "patient" refers to a mammal, preferably a human.

The compounds of this invention may contain one or more asymmetric carbon atoms and thus may occur as racemates and racemic mixtures, single enantiomers, diastereomeric mixtures and individual diastereomers. All such isomers of the compounds disclosed herein are expressly included within the scope of the present invention. Each stereogenic carbon may be of the R or S configuration.

Some of the compounds described herein contain olefinic double bonds, and unless specified otherwise, are meant to include both E and Z geometric isomers. For example, fragment AA also implies fragment AB as shown below.

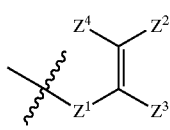

AA

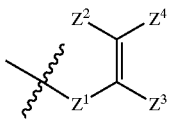

AB

Selection of an atom such as carbon or "C" for a variable such as $A^1$ requires there to be four bonds to this carbon atom. When $A^1$ is C, that would require a double bond to an adjacent atom, in this case, to either $A^2$ or $A^3$ with the appropriate selection of $A^2$ or $A^3$ to accommodate said double bond. When $A^1$ is $CS^1$, then $A^2$ and $A^3$ are selected to accommodate the single bond attachment to $A^1$. $A^1$ through $A^6$ may be interpreted in a similar fashion. Selection of an atom such as nitrogen for a variable such as $A^2$ requires there to be three bonds to this nitrogen atom. This can be accomplished by providing a double bond to the adjacent atoms, in this case, either $A^1$ or $A^3$ with the appropriate selection of $A^1$ or $A^3$ to accommodate said double bond. $A^2$ through $A^6$ may be interpreted in a similar fashion. In addition, $M^1$ through $M^6$ may be interpreted in this fashion, i.e., as described for $A^1$ through $A^6$. Substituents may be attached to the ring such as when the variable $M^2$ is taken to be $C(P^2)_{1-2}$. $C(P^2)_{1-2}$ is intended to indicate that the carbon to which the substituents $P^2$ are attached i) may be saturated, in which case the carbon atom may accommodate two substituents independently chosen from $P^2$, or ii) may be unsaturated, in which case the carbon atom may only accommodate one substituent.

Combinations of substituents and variables thereof that result in stable compounds are also contemplated within the present invention. The term "stable" as used herein refers to compounds which possess stability sufficient to allow for their manufacture and which maintain their integrity for a sufficient period of time to be useful as therapeutic or diagnostic agents.

As used herein, the compounds of this invention are defined to include pharmaceutically acceptable derivatives and prodrugs thereof. A "pharmaceutically acceptable derivative or prodrug" includes any pharmaceutically acceptable salt, ester, salt of an ester, or other derivative of a compound of the present invention which, upon administration to a subject, is capable of providing (directly or indirectly) a compound of the invention. Particularly favored derivatives and prodrugs are those that increase the bioavailability of the compounds of the present invention when such compound is administered to a subject (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group that enhances aqueous solubility or active transport through the gut membrane is appended to a compound of the present invention. Pharmaceutically acceptable salts of the compounds disclosed herein include those derived from pharmaceutically acceptable inorganic and organic acids and bases known to those skilled in the art. Examples of suitable acid salts include, but are not limited to, the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, trifluoroacetic, tosylate and undecanoate. Other acids, for example oxalic, while not in themselves pharmaceutically acceptable, may be employed in the preparation of salts useful as intermediates in obtaining the compounds of the present invention and their pharmaceutically acceptable acid additional salts.

Salts derived from appropriate bases include, but are not limited to, the following: alkali metal (e.g., sodium), alkaline earth metal (e.g., magnesium), ammonium and N-($C_{1-4}$ alkyl)$_4^+$salts. The present invention also envisions the quaternization of any basic nitrogen-containing groups of the compounds disclosed herein. Water- or oil-soluble or dispersible products may be obtained by such quaternization.

Methods of Production

The compounds of the present invention may be synthesized using conventional techniques known in the art. Advantageously, these compounds are conveniently synthesized from readily available starting materials. Following are general synthetic schemes for manufacturing compounds of the present invention. These schemes are illustrative and are not meant to limit the possible techniques one skilled in the art may use to manufacture compounds disclosed herein. Different methods will be evident to those skilled in the art. Additionally, the various steps in the synthesis may be performed in an alternate sequence or order to give the desired compound(s).

The preparation of cyanoguanidines useful to this invention are described in Scheme 1 a. An aniline or heterocyclic amine can react with a variety of isocyanates which are either commercially available or readily prepared by several methods such as reaction of an amine with phosgene and a base such as triethylamine, or reaction with triphosgene, to form a urea such as 1a.1. Amines may be prepared by many methods such as displacement of a halide by potassium pthalimide, and liberation of the amine by the action of hydrazine, or reduction of a nitro group or a nitrile. Nitriles may be reduced to amines (such as 1a.2) by many methods including those detailed in Hudlicky, M., "Reductions in Organic Chemistry", 2nd Ed., ACS Monograph 188, 1996, pp 239–245 American Chemical Society, Washington, D.C. Cyanoguanidines are conveniently prepared by reaction with the commercially available reagent diphenyl cyanocarbonimidate to initially provide an intermidiate imidate such as 1a.3, which is then reacted with an amine either neat or in a solvent at elevated temperatures in a sealed reaction vessel to provide a cyanoguanidine such as 1a.4

Scheme 1a:

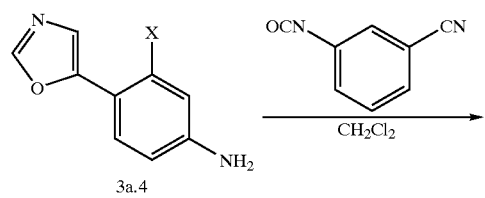

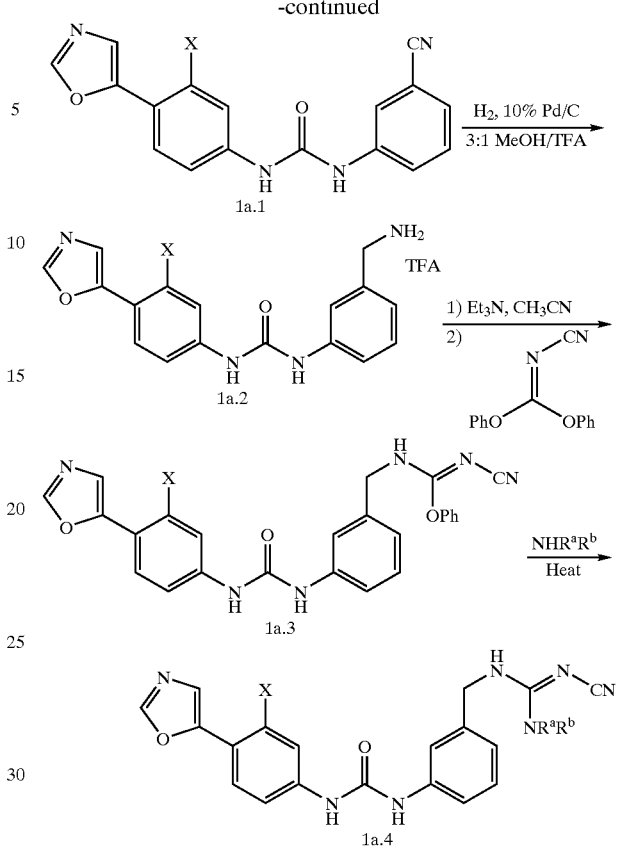

NHR$^a$R$^b$ = a mono, disubsubstituted or cyclic amine

Cyanoimidates useful to this invention are also conviently prepared from the intermediate cyanoimidate 1 a.3 by reaction with an alcohol in the presence of either sodium metal, or a hydride base such as sodium hydride to provide 1b.1.

Scheme 1b:

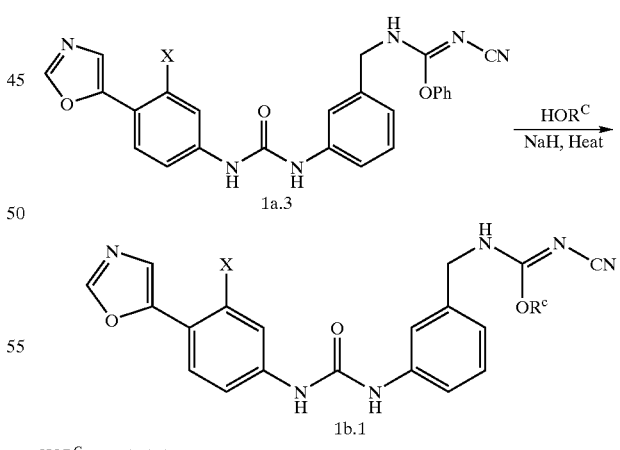

HOR$^c$ = an alcohol

Alkenes useful to this invention may be prepared by several methods including that depicted in scheme 1c. The preparation of nitroalkenes from amines has been describe in many references including Schulze, F. R, et. Al., Arch Pharm (1994) 327 (7) 455–462, and from sulfonamides by Masereel, B., et. Al., Eur J Med. Chem (1997) 32(5)

453–456. In this case the reaction of an amine such as 1a.2, with the commercially available reagent 1,1-bis (methylthio)-2-nitroethylene provides the thioalkene 1c.1. This may also be a useful intermediate, since it can further react with an amine to provide the bis-aminoalkene 1c.2. Alternatively thioalkene 1c.1 can react with a sulfonamide in the presence of base to provide bis-aminoalkene 1c.3.

Scheme 1c:

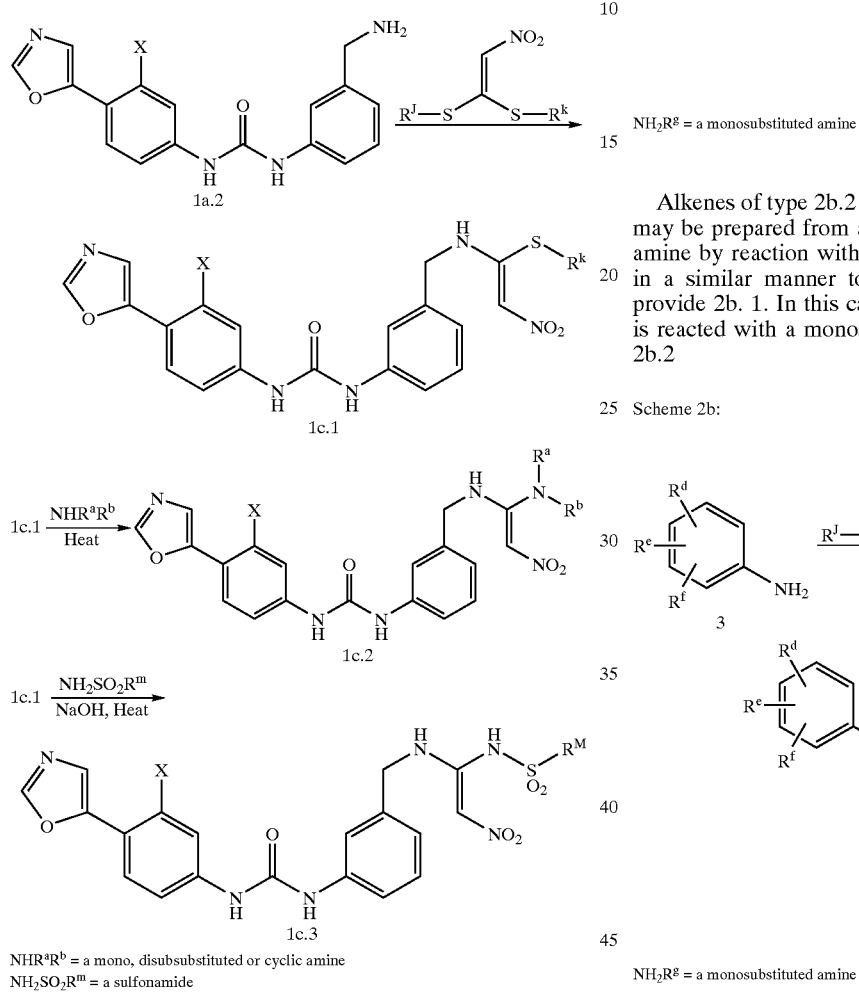

NHR$^a$R$^b$ = a mono, disubsubstituted or cyclic amine
NH$_2$SO$_2$R$^m$ = a sulfonamide Cyanoguanidines of type 2a.2 are also useful to this invention and may be prepared from an aniline such as 3, or heterocyclic amine by reaction with diphenyl cyanocarbonimidate in a manner similar to that described for scheme 1a, to provide 2a.1. In this case the intermediate imidate 2a.1 is reacted with an monosubstituted amine to provide compound 2a.2.

Scheme 2a:

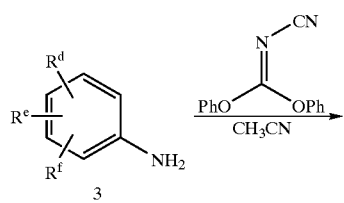

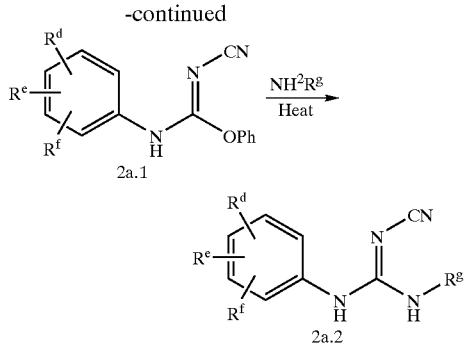

NH$_2$R$^g$ = a monosubstituted amine

Alkenes of type 2b.2 are also useful to this invention, and may be prepared from an aniline such as 3, or heterocyclic amine by reaction with 1,1-bis(methylthio)-2-nitroethylene in a similar manner to that described for scheme 1b to provide 2b. 1. In this case the intermediate thioalkene 2b.1 is reacted with a monosubstituted amine to provide alkene 2b.2

Scheme 2b:

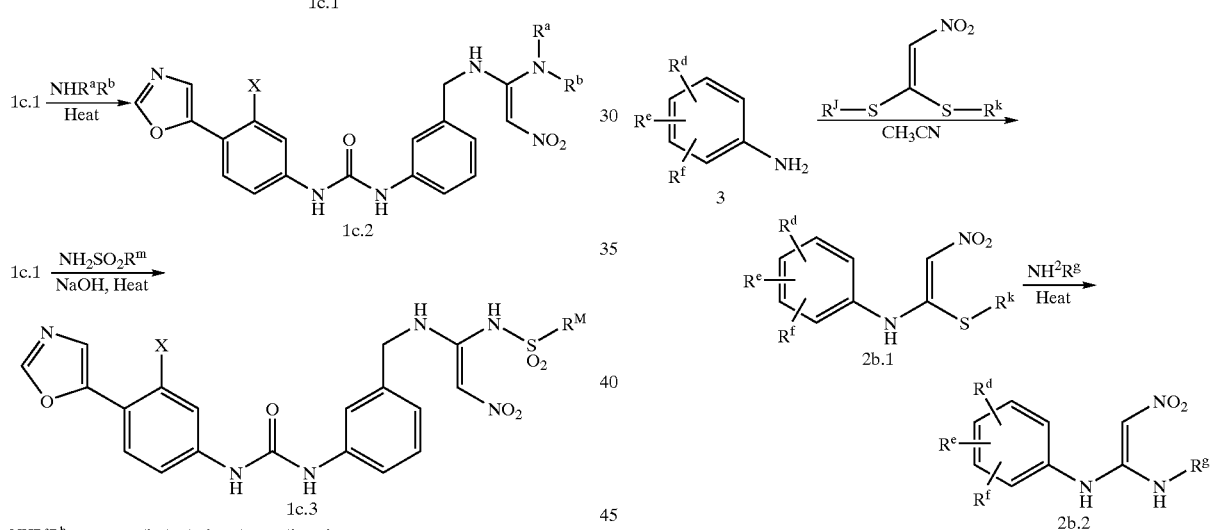

NH$_2$R$^g$ = a monosubstituted amine

The preparation of alkenes useful to this invention are also described in scheme 2c, by the reaction of a carbon nucleophile with a carbodiimide. Carbodiimides may be prepared by several methods including desulfurization of a thiourea with reagents such as methanesulfonyl chloride int the presence a base and catalytic N,N-dimethylaminopyridine (DMAP) or by the use of 1,1'thiocarbonyldi-2,2'-pyridone and catalytic DMAP as described by Kim S., and Yi, K. Y., in *J. Org. Chem.* 1986, 51, 2613–2615. Thioureas are readily prepared by several methods including reaction of a urea with Lawesson's reagent, or by reaction of an amine with an isothiocyanate. Isothiocyanates are either commercially available or readily prepared by reaction of an amine with 1,1'thiocarbonyldi-2,2'-pyridone. In this case an aniline or heterocyclic amine such as 3, may be reacted with the commercially available reagent 1,1'thiocarbonyldi-2,2'pyridone (2c.1) to provide isothiocyante 2c.2. Reaction of the isothiocyante with a monosubstituted amine provides thiourea 2c.3. The thiourea is converted to the carbodiimide by reaction with 1,1'thiocarbonyldi-2,2'pyridone (2c.1) in the presence of a catalytic amount of DMAP to provide 2c.4. The intermediate carbodiimide may react with a variety of activated carbon nucleophiles in the presence of a suitable base capable of preparing the corresponding anion of the carbon nucleophile of interest. For example a variety of substitued alkenes of type 2c.6 where the electron withdrawing group (EWG) is a nitro group may be prepared by reaction of a nitroalkane (2c.5, EWG=NO$_2$) which is either commercially available, or readily prepared by one skilled in the art of organic synthesis, with carbodiimide 2c.4, in the presence of a base (for example see: Moimas, F.; Angeli, C.; Comisso, G.; Zanori, P.; et al.; Synthesis 1985, 509). Sulfones (2c.5, EWG=SO$_2$R) or nitriles (2c.5, EWG=CN) may also be used as activated carbon nucleophiles of type 2c.5 in the presence of a suitable base to provide alkenes of type 2c.6. Alternatively activated carbon nucleophiles with two electron withdrawing groups of type 2c.7 are also useful to this invention and are either commercially available or readily prepared by one skilled in the art of organic chemistry. Reaction of carbodiimide 2c.4 with active methylene compounds of type 2c.7 in the presence of a base provide alkenes of type 2c.7 (for example see: Stephen, A., *Montsh Chem* (1966) p 97.).

Scheme 2c:

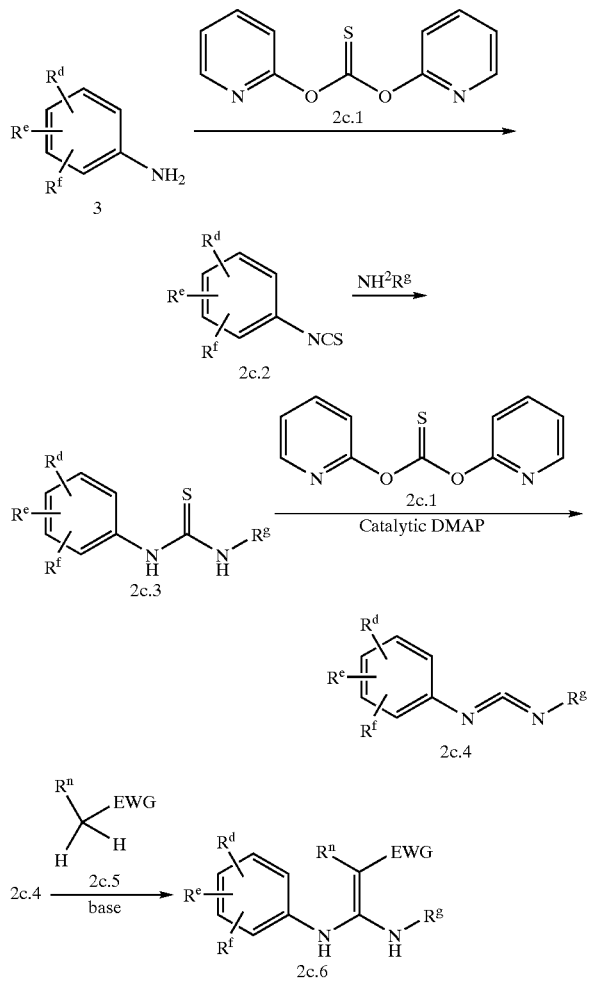

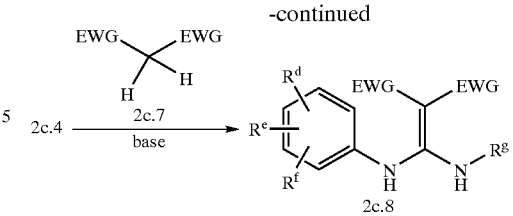

NH$_2$R$^g$ = a monosubstituted amine
EWG = electron withdrawing group such as CO$_2$R, NO$_2$, SO$_2$R, CN, etc.

Cyanoguanidines may also be prepared from thiouronium salts as illustrated in scheme 2d. An isothiocyanate (such as 2c.2) is reacted with sodium cyanamide, which is prepared by reaction of sodium metal with cyanamide in a solvent such as methanol or ethanol, to produce thiouronium salt 2d.1. Addition of an amine in the presence of a coupling agent such as 1-(3-dimethylaminopropyl)-3-ethylcarbodiimide hydrochloride (EDC) provides the desired cyanoguanidine 2a.2

Scheme 2d:

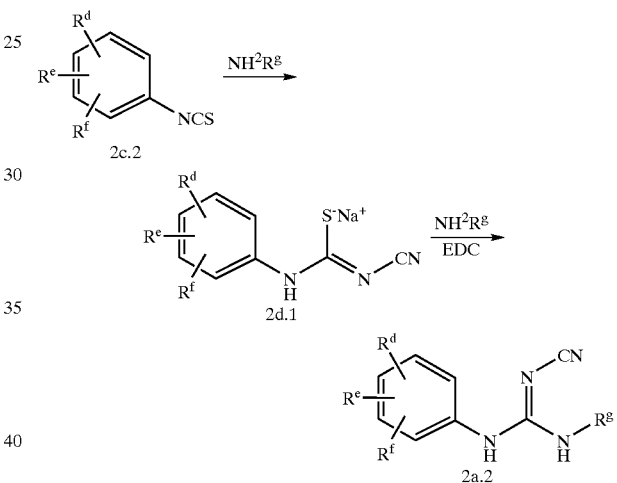

Amines of type 3a.4 are useful for the preparation of compounds useful to this invention may be commercially available or readily prepared by many methods known to one skilled in the art of organic chemistry, and are described in "Comprehensive Organic Transformations. A Guide to Functional Group Preparation." pp-385–439. Richard C. Larock 1989 VCH Publishers, Inc. Examples include but are not limited to, reduction of a nitro group, reduction of an azide and reduction of a nitrile and are detailed in schemes 3a to 3d.

A general method for the synthesis of an amine useful in this invention can be performed by metal catalyzed cross coupling methods known in the literature. The simplest case is a Suzuki type cross coupling (Miyaura, N., Yanagi, T. Suzuki, A., *Synth. Comm.* 11(7):513–519 (1981); A. Suzuki et. al., *J. Am. Chem. Soc.* 111:513 (1989); and V. N. Kalinin, *Russ. Chem. Rev.* 60:173 (1991)) of an aryl boronic acid or ester (3a.1) (as shown below) with an appropriate bromo-heterocycle in the presence of a suitable catalyst such as tetrakis(triphenylphosphine) palladium. After the cross coupling has been performed the product may be deprotected. The choice of protecting group and its method of removal will be readily apparent to one skilled in the art of organic chemistry. Such considerations and methods are, for example, described by Greene, Theodora W. and Wuts, Peter G. M. in "Protective Groups in Organic Synthesis." 2nd Ed. (1991) Publisher: (John Wiley and Sons, Inc., New York, N.Y. For example, if the protecting group is acetyl the product may be deprotected by treatment with aqueous potassium hydroxide at a concentration of 0.5N to 5 N at room temperature to 100° C. for a period between 0.5 h and 24 h.

For example aryl boronic acid (3a.5) may react with the known 5-bromothiazole (3a.6) in the presence of tetrakis (triphenylphosphine) palladium (0), to provide (3a.7) which may be deprotected by an appropriate method.

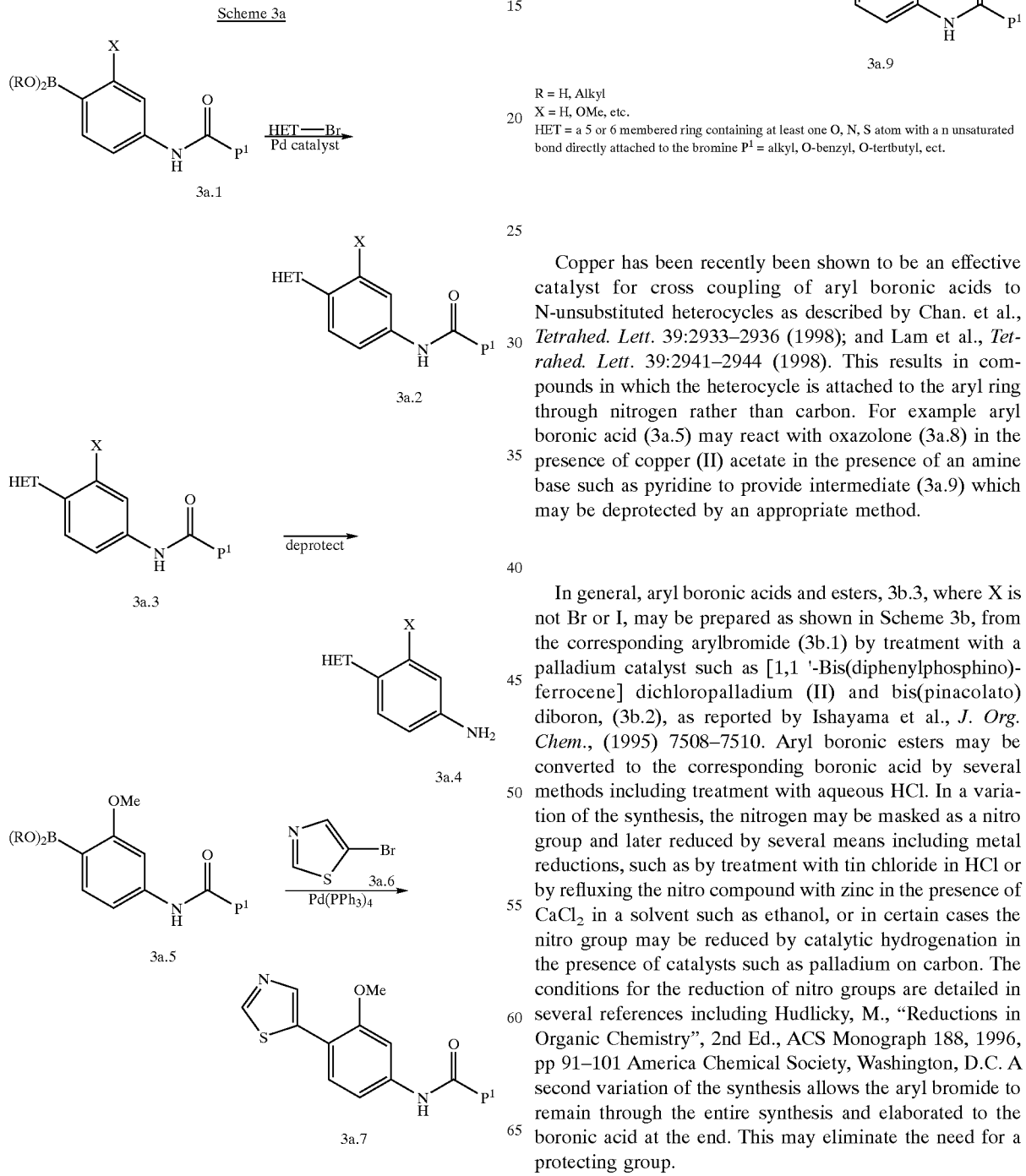

R = H, Alkyl
X = H, OMe, etc.
HET = a 5 or 6 membered ring containing at least one O, N, S atom with a n unsaturated bond directly attached to the bromine P$^1$ = alkyl, O-benzyl, O-tertbutyl, ect.

Copper has been recently been shown to be an effective catalyst for cross coupling of aryl boronic acids to N-unsubstituted heterocycles as described by Chan. et al., Tetrahed. Lett. 39:2933–2936 (1998); and Lam et al., Tetrahed. Lett. 39:2941–2944 (1998). This results in compounds in which the heterocycle is attached to the aryl ring through nitrogen rather than carbon. For example aryl boronic acid (3a.5) may react with oxazolone (3a.8) in the presence of copper (II) acetate in the presence of an amine base such as pyridine to provide intermediate (3a.9) which may be deprotected by an appropriate method.

In general, aryl boronic acids and esters, 3b.3, where X is not Br or I, may be prepared as shown in Scheme 3b, from the corresponding arylbromide (3b.1) by treatment with a palladium catalyst such as [1,1 '-Bis(diphenylphosphino)-ferrocene] dichloropalladium (II) and bis(pinacolato) diboron, (3b.2), as reported by Ishayama et al., J. Org. Chem., (1995) 7508–7510. Aryl boronic esters may be converted to the corresponding boronic acid by several methods including treatment with aqueous HCl. In a variation of the synthesis, the nitrogen may be masked as a nitro group and later reduced by several means including metal reductions, such as by treatment with tin chloride in HCl or by refluxing the nitro compound with zinc in the presence of CaCl$_2$ in a solvent such as ethanol, or in certain cases the nitro group may be reduced by catalytic hydrogenation in the presence of catalysts such as palladium on carbon. The conditions for the reduction of nitro groups are detailed in several references including Hudlicky, M., "Reductions in Organic Chemistry", 2nd Ed., ACS Monograph 188, 1996, pp 91–101 America Chemical Society, Washington, D.C. A second variation of the synthesis allows the aryl bromide to remain through the entire synthesis and elaborated to the boronic acid at the end. This may eliminate the need for a protecting group.

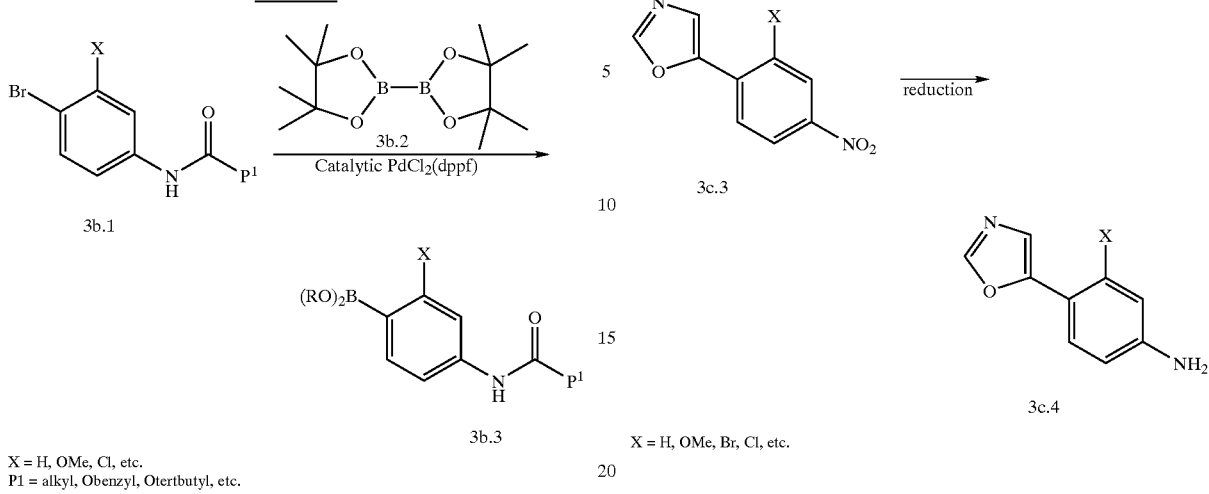

In certain cases, it may be more expedient to construct the heterocyclic ring by other methods. A general method for the synthesis of 5-membered heterocycles includes the 1,3-dipolar cycloaddition reaction, which is well known to one skilled in the art of organic chemistry and is described by Padwa, Albert (Editor) in "1,3-Dipolar Cycloaddition Chemistry, Vol. 2" (John Wiley and Sons, New York, N.Y. [1984]); and Padwa, Albert (Editor) in "1,3-Dipolar Cycloaddition Chemistry, Vol. 1" (John Wiley and Sons, New York, N.Y. [1984]). For example, oxazoles may be prepared by 1,3 dipolar cycloaddition of the corresponding aldehyde (3c.1) and (p-tolylsulfonyl)methyl isocyanate (TOSMIC) (3c.2) as shown in scheme 3c. The aldehyde may be commercially available or prepared from the corresponding methyl group by oxidation with reagents such as $CrO_3$, $MnO_2$, and ammonium cerium (IV) nitrate by methods well known to one skilled in the art of organic chemistry and described in Hudlicky, M., "Oxidations in Organic Chemistry", ACS Monograph 186 (1990), American Chemical Society, Washington, D.C. The nitro group in intermediate (3c.3), is reduced to an amine (3c.4), as discussed above.

An alternative method of producing amines useful to this invention is by nucleophilic attack of an electron deficient ring system as outlined in scheme 3d. Halonitrobenzenes (3d.1), are either commercially available or readily prepared by methods known to one skilled in the art of organic synthesis. Displacement with a variety of nucleophiles produces compounds of structure (3d.2). In one example, heating (3d.3) with a nucleophilic heterocycle such as triazole with or without the addition of a base provides the intermediate nitro compound which may be reduced as previously describe to provide amines (3d.4). Alternatively, simple organic nucleophiles such as cyanide can be reacted with halonitrobenzene (3d.5) to provide an intermediate nitro-compound which can be reduced by many methods to amine (3d.6).

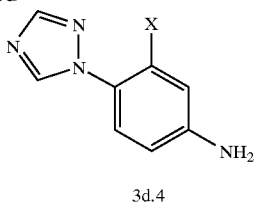

3d.4

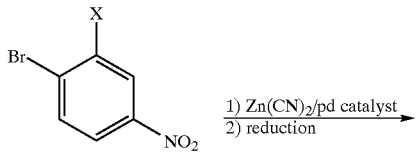

3d.5

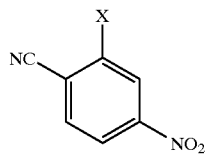

3d.6

The compounds of the present invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Utility

The compounds of the present invention inhibit IMPDH enzyme, and are thus useful in the treatment, including prevention and therapy, of disorders which are mediated or effected by cells which are sensitive to IMPDH inhibition, as described previously. The present invention thus provides methods for the treatment of IMPDH-associated disorders, comprising the step of administering to a subject in need thereof at least one compound of the Formula I, IA, II or IIA in an amount effective therefor. Other therapeutic agents, such as those described below, may be employed with the inventive compounds in the present methods. In the methods of the present invention, such other therapeutic agent(s) may be administered prior to, simultaneously with or following the administration of the compound(s) of the present invention.

Use of the compounds of the present invention in treating IMPDH-associated conditions is exemplified by, but is not limited to, treating a range of disorders such as: treatment of transplant rejection, such as kidney, liver, heart, lung, pancreas (e.g., islet cells), bone marrow, cornea, small bowel, skin allografts, skin homografts (such as employed in burn treatment), heart valve xenografts, serum sickness, and graft vs. host disease; in the treatment of autoimmune diseases, such as rheumatoid arthritis, psoriatic arthritis, multiple sclerosis, juvenile diabetes, asthma, inflammatory bowel disease (such as Crohn's disease and ulcerative colitus), pyoderma gangrenum, lupus (systemic lupus erythematosis), myasthenia gravis, psoriasis, dermatitis, dermatomyositis, eczema, seborrhoea, pulmonary inflammation, eye uveitis, hepatitis, Grave's disease, Hashimoto's thyroiditis, autoimmune thyroiditis, Behcet's or Sjorgen's syndrome (dry eyes/mouth), pernicious or immunohaemolytic anaemia, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, viteligo (depigmentation of the skin), alopecia areata, autoimmune alopecia, autoimmune hypopituatarism, Guillain-Barre syndrome, and alveolitis; in the treatment of T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); in the treatment of inflammatory diseases such as osteoarthritis, acute pancreatitis, chronic pancreatitis, asthma, acute respiratory distress syndrome, Sezary's syndrome and vascular diseases which have an inflammatory and or a proliferatory component such as restenosis, stenosis and artherosclerosis; in the treatment of cancer and tumor disorders, such as solid tumors, lymphomas and leukemia; in the treatment of fungal infections such as mycosis fingoides; in protection from ischemic or reperfusion injury such as ischemic or reperfusion injury that may have been incurred during organ transplantation, myocardial infarction, stroke or other causes; in the treatment of DNA or RNA viral replication diseases, such herpes simplex type 1 (HSV-1), herpes simplex type 2 (HSV-2), hepatitis (including hepatitis B and hepatitis C) cytomegalovirus, Epstein-Barr, and human immunodeficiency virus (HIV).

Additionally, IMPDH is also known to be present in bacteria and thus may regulate bacterial growth. As such, the IMPDH-inhibitor compounds of the present invention may be useful in treatment or prevention of bacterial infection, alone or in combination with other antibiotic agents.

In a particular embodiment, the compounds of the present invention are useful for the treatment of the aforementioned exemplary disorders irrespective of their etiology, for example, for the treatment of transplant rejection, rheumatoid arthritis, inflammatory bowel disease, and viral infections.

The present invention also provides pharmaceutical compositions comprising at least one of the compounds of Formula I, IA, II or IIA or a salt thereof, capable of treating an IMPDH-associated disorder in an amount effective therefor, alone or in combination with at least one additional therapeutic agent, and any pharmaceutically acceptable carrier, adjuvant or vehicle. "Additional therapeutic agents" encompasses, but is not limited to, an agent or agents selected from the group consisting of an immunosuppressant, an anti-cancer agent, an anti-viral agent, an anti-inflammatory agent, an anti-fungal agent, an antibiotic, or an anti-vascular hyperproliferation compound.

The term "pharmaceutically acceptable carrier, adjuvant or vehicle" refers to a carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the compounds of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the Formula I, IA, II or IIA may be administered by any suitable means, for example, orally, such as in the form of tablets, capsules, granules or powders; sublingually; buccally; parenterally, such as by subcutaneous, intravenous, intramuscular, or intrastemal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrastemal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to IMPDH-associated disorders.

The compounds of the present invention may be employed alone or in combination with each other and/or other suitable therapeutic agents useful in the treatment of IMPDH-associated disorders, such as IMPDH inhibitors other than those of the present invention, immunosuppressants, anti-cancer agents, anti-viral agents, anti-inflammatory agents, anti-fungal agents, antibiotics, or anti-vascular hyperproliferation agents.

Exemplary such other therapeutic agents include the following: cyclosporins (e.g., cyclosporin A), CTLA4-Ig, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins constructed from CD40 and/or CD154/gp39 (e.g., CD40Ig and CD8gp39), inhibitors, such as nuclear translocation inhibitors, of NF-kappa B function, such as deoxyspergualin (DSG), non-steroidal antiinflammatory drugs (NSAIDs) such as ibuprofen, celecoxib and rofecoxib, steroids such as prednisone or dexamethasone, gold compounds, antiviral agents such as abacavir, antiproliferative agents such as methotrexate, leflunomide, FK506 (tacrolimus, Prograf), cytotoxic drugs such as azathiaprine and cyclophosphamide, TNF-α inhibitors such as tenidap, anti-TNF antibodies or soluble TNF receptor, and rapamycin (sirolimus or Rapamune) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art.

Compounds disclosed herein are capable of targeting and inhibiting IMPDH enzyme. Inhibition can be measured by various methods, including, for example, IMP dehydrogenase HPLC assays (measuring enzymatic production of XMP and NADH from IMP and NAD) and IMP dehydrogenase spectrophotometric assays (measuring enzymatic production of NADH from NAD). See, e.g., Montero et al., *Clinica Chimica Acta* 238:169–178 (1995). Additional assays known in the art can be used in ascertaining the degree of activity of a compound ("test compound") as an IMPDH inhibitor. The inventors used the following assay to determine the degree of activity of the compounds disclosed herein as IMPDH inhibitors:

Activity of IMPDH I and IMPDH II was measured following an adaptation of the method described in WO 97/40028. The reaction mixture was prepared containing 0.1M Tris pH 8.0, 0.1 M KCl, 3 mM EDTA, 2 mM DTT, 0.4 mM IMP and 40 nM enzyme (IMPDH I or IMPDH II). The reaction was started by the addition of NAD to a final concentration of 0.4 mM. The enzymatic reaction was followed by measuring the increase in absorbance at 340 nM that results from the formation of NADH. For the analysis of potential inhibitors of the enzyme, compounds were dissolved in DMSO to a final concentration of 10 mM and added to the assay mixture such that the final concentration of DMSO was 2.5%. The assay was carried out in a 96-well plate format, with a final reaction volume of 200 □1.

Compounds disclosed herein are capable of inhibiting the enzyme IMPDH at a measurable level, under the above-described assay or an assay which can determine an effect of inhibition of the enzyme IMPDH.

The following examples illustrate preferred embodiments of the present invention and do not limit the scope of the present invention which is defined in the claims. Abbreviations employed in the Examples are defined below. Compounds of the Examples are identified by the example and step in which they are prepared (e.g., "1A" denotes the title compound of step A of Example 1), or by the example only where the compound is the title compound of the example (for example, "2" denotes the title compound of Example 2).

| | Abbreviations |
|---|---|
| Ac | Acetyl |
| AcOH | Acetic acid |
| aq. | Aqueous |
| CDI | Carbonyldiimidazole |
| Bn | Benzyl |
| Boc | tert-butoxycarbonyl |
| DMAP | Dimethylaminopyridine |
| DMF | dimethylformamide |

| | -continued |
|---|---|
| | Abbreviations |
| DMSO | Dimethylsulfoxide |
| EDC | 1-(3-Dimethylaminopropyl)-3-ethylcarbodiimide hydrochloride |
| EtOAc | Ethyl acetate |
| Et | Ethyl |
| EtOH | Ethanol |
| h | Hours |
| i | iso |
| HPLC | High pressure liquid chromatography |
| HOAc | Acetic acid |
| THF | Tetrahydrofuran |
| Lawesson's Reagent | [2,4-bis(4-methoxyphenyl)-1,3-dithia-2,4-diphosphetane-2-4-disufide |
| LC | liquid chromatography |
| Me | Methyl |
| MeOH | Methanol |
| min. | Minutes |
| $M^+$ | $(M + H)^+$ |
| $M^{+1}$ | $(M + H)^+$ |
| MS | Mass spectrometry |
| n | normal |
| Pd/C | Palladium on carbon |
| Ph | Phenyl |
| Pr | Propyl |
| Ret Time | Retention time |
| rt or RT | Room temperature |
| sat. | Saturated |
| TFA | Trifluoroacetic acid |
| THF | Tetrahydrofuran |
| TOSMIC | Tosylmethyl isocyanide |
| YMC | YMC Inc, Wilmington, NC 28403 |

EXAMPLE 1

Preparation of N-[3-[[[(Cyanoamino)phenoxymethylene]amino]methyl]phenyl]-N'-[3-methoxy-4-(5-oxazolyl)phenyl]urea

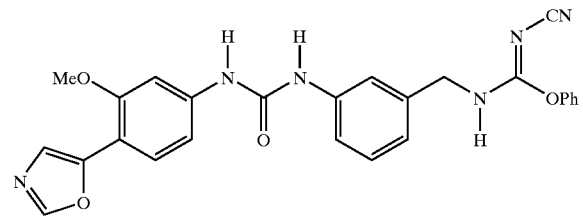

1A. Preparation of 4-Nitro-2-methoxy-(a,a-bisacetoxy)toluene

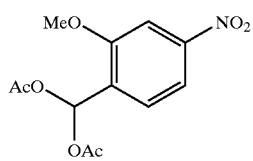

To a 5 L three necked round bottom flask equipped with a mechanical stirrer was added 4-nitro-2-methoxytoluene (150.0 g, 0.8973 mol), HOAc (900 mL) and Ac₂O (900 mL). The mixture was stirred and cooled to 8° C. with an acetone/ice bath. Concentrated H₂SO₄ (136 mL) was carefully added while keeping the pot temperature<19° C. After cooling to 0° C., CrO₃ (252.6 g, 2.526 mol, 2.815 equiv.) was added portion-wise over 1 hour while maintaining the reaction temperature between 0–10° C. After the addition, the mixture was stirred at 0° C. for 30 minutes at which time the reaction was complete. The reaction mixture was then carefully poured into ice (1.5 kg) with stirring to give a slurry. The remaining black gummy residue was rinsed with HOAc (3×100 mL), and the washes were added to the slurry. After stirring for 10 minutes, the slurry was filtered. The cake was washed with water (3×400 mL) and suction dried for 17 hours to give 4-nitro-2-methoxy-(a,a-bisacetoxy) toluene (1A, 129.0 g, 51%). $^1$H NMR (CDCl$_3$) d 8.02 (s, 1H), 7.89 (d, J=8.4 Hz, 1H), 7.77 (s, 1H), (d, 8.4 Hz, 1H), 3.98 (s, 3H), 2.16 (s, 6H).

1B. Preparation of 4-Nitro-2-methoxybenzaldehyde

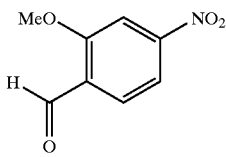

To a 2 L rounded bottom flask equipped with a condenser and a mechanical stirrer was placed 1A (250.7 g, 0.8851 mol), dioxane (300 mL) and concentrated HCl (60 mL). The reaction mixture was heated to reflux and stirred under N$_2$ for 20 hours. Water (250 mL) was added dropwise while maintaining the reaction mixture at reflux. After cooling to 0° C. with an ice/water bath, the resulting slurry was stirred for 30 minutes and then filtered. The cake was washed with water (4×200 mL) and suction dried for 17 hours to give 4-nitro-2-methoxybenzaldehyde (1B, 146.3 g, 91%) as yellow solid. $^1$H NMR (CDCl$_3$) d 10.54 (s, 1H), 8.00 (d, J=8.3 Hz, 1H), 7.91 (s, 1H), 7.89 (d, J=8.3 Hz, 1H), 4.08 (s, 3H).

1C. Preparation of 5-(4-Nitro-2-methoxyphenyl)oxazole

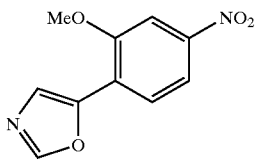

To a 5 L three necked round bottom flask equipped with a condenser and a mechanical stirrer was placed 1B (146.3 g, 0.8076 mol), TOSMIC (157.7 g, 0.8077 mol), K$_2$CO$_3$ (116.6 g, 0.8075 mol) and MeOH (2.5 L). The mixture was heated to reflux under N$_2$ and stirred for 3 hours. Water (1.25 L) was added drop-wise while maintaining the pot temperature between 59–69° C. The resulting slurry was cooled to room temperature, and then to 5° C. with an ice-water bath. After stirring for 30 minutes at 5° C., the slurry was filtered. The resulting cake was washed with water (3×400 mL) and dried in a vacuum oven at 45° C. for 20 hours to give 5-(4-nitro-2-methoxyphenyl)oxazole (1C, 148.5 g, 84%) as a yellow-reddish solid. $^1$H NMR (CDCl$_3$) d 8.02 (s, 1H), 7.97 (d, J=2 Hz, 1H), 7.95 (d, J=2 Hz, 1H), 7.86 (s, 1H), 7.78 (s, 1H), 4.11 (s, 3H).

1D. Preparation of 5-(4-Amino-2-methoxyphenyl)oxazole

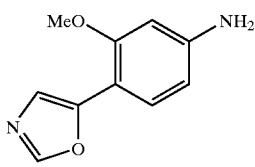

In a 2 L hydrogenation flask was placed 1C (130.0 g, 0.6131 mol), Pd/C (10%, 26.2 g) and absolute EtOH (1280 mL). The mixture was hydrogenated at 35–45 psi H$_2$ until the reaction was complete. The mixture was filtered over a pad of celite (20 g) and the cake was washed with EtOH (3×100 mL). The filtrate was concentrated to a volume of 350 mnL. Heptane (500 mL) was added to the resulting slurry. After stirring for 2 hours at room temperature, the slurry was filtered. The cake was washed with heptane (3×100 mL) and air-dried to give 80.0 g of 5-(4-amino-2-methoxyphenyl)oxazole (1D). Another 30.2 g of product was recovered from the mother liquor affording a total yield of 95%. $^1$H NMR (CDCl$_3$) d 7.88 (s, 1H), 7.60 (d, J=8.4 Hz, 1H), 7.41 (s, 1H), 6.41 (dd, J=8.4, 2.1 Hz, 1H), 3.34 (d, J=2.1 Hz, 1H), 3.98 (bs, 2H), 3.94 (s, 3H).

1E. Preparation of N-(3-Cyanophenyl)-N'-[3-methoxy-4-(5-oxazolyl)phenyl]urea

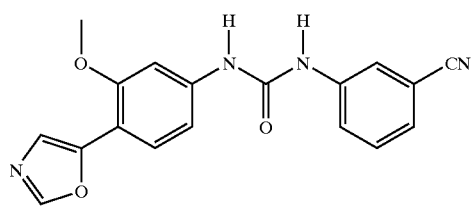

3-Methoxy-4-(5-oxazolyl)aniline, 1D (1.00 g, 5.26 mmol) and 3-cyanophenyl isocyanate (1.17 g, 7.89 mmol) in dichloromethane (40 mL) were stirred at rt for 20 h. The precipitate formed was collected by filtration, followed by washing with dichlorometnane to provide 1E (1.57 g, 89% yield) as a yellow solid. (LC/MS retention time=3.67 min.; M$^+$=335. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

1F. Preparation of the TFA salt of N-[3-(Aminomethyl)phenyl]-N'-[3-methoxy-4-(5-oxazolyl)phenyl]urea

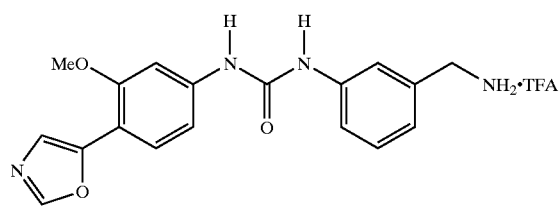

A suspension of 1E (421 mg, 1.26 mmol) and 10% Pd/C (80 mg) in 3:1 MeOH/TFA (100 mL) was stirred under a hydrogen environment provided by a balloon for 16 h. After the Pd/C and solvent were removed by filtration and evaporation, respectively, the residue was dissolved in water (50 mL) which resulted in a cloudy solution. To the solution was added methanol until the cloudiness disappeared. The solution was washed with dichloromethane (3×30 mL) and then concentrated to approximately 40 mL. The remaining solution was then lyophilized to provide 1F (477 mg, 84% yield) as a white powder. (LC/MS retention time=2.86 min.; M$^+$=339. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

Preparation of N-[3-[[[(Cyanoamino)phenoxymethylene]amino]methyl]phenyl]-N'-[3-methoxy-4-(5-oxazolyl)phenyl]urea

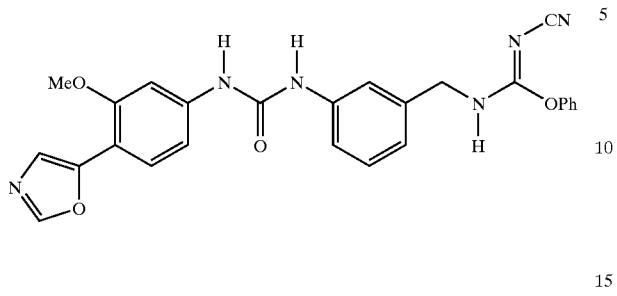

To a suspension of 1F (0.150 g, 0.220 mmol) in 50 ml of acetonitrile was added triethylamine (0.092 g, 0.660 mmol). The mixture was stirred until the solution became homogeneous. Diphenyl cyanocarbonimitate (0.109 g, 0.440 mmol) was added, and the reaction mixture was stirred at reflux for 14 h. The reaction was cooled, and the solvent was removed under reduced pressure to give a yellowish oil which was subjected to silica gel chromatography to give 0.079 g (75%) of 1 as a white solid. The product was determined to be 86% pure by HPLC (Retention time=3.94 min. Column: YMC S5 ODS 4.6×5.0 mm Ballistic. Solvent A=10% MeOH, 90% $H_2O$, 0.2% $H_3PO_4$; Solvent B=90% MeOH, 10% $H_2O$, 0.2% $H_3PO_4$).

EXAMPLE 2

Preparation N-[3-[[[Amino(cyanoamino)methylene]amino]methyl]phenyl]-N'-[3-methoxy-4-(5-oxazolyl)phenyl]urea

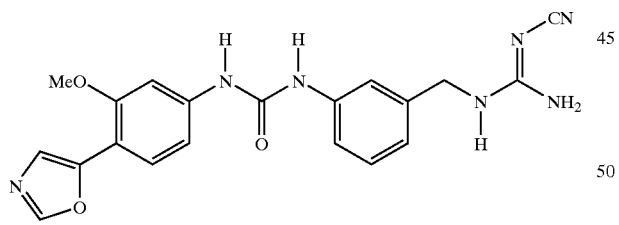

A solution of 1 (35 mg, 0.072 mmol) and ammonia (2.0 M EtOH solution, 4.0 mL, 8.0 mmol) in ethanol (4 mL) was heated in a sealed tube at 80° C. for 15 h. After the solvent was evaporated under reduced pressure, the residue was subjected to column chromatography (10% MeOH/CHCl$_3$) to afford compound 2 (19 mg, 66% yield) as a white solid. (LC/MS retention time=3.30 min.; M$^+$=406. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

EXAMPLE 3

Preparation of N-[3-[[[(Cyanoamino)(4-morpholinyl)methylene]amino]methyl]phenyl]-N'-[3-methoxy-4-(5-oxazolyl)phenyl]urea

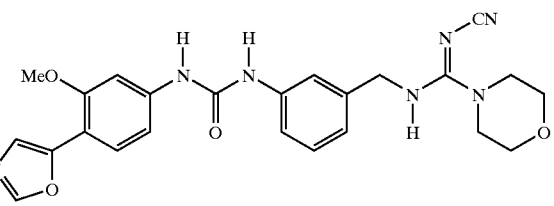

To 1 (0.029 g, 0.060 mmol) in 7 mL of acetonitrile was added excess morpholine (15.7 µL, 0.180 mmol). The mixture was heated at reflux for 48 h, cooled to room temperature, and the solvent was removed under reduced pressure. The residue was subjected to silica gel chromatography to give 14 mg of a residue which by HPLC contained 51% of 3. The residue was subjected to preparative HPLC to give 2.1 mg of 3 as a white solid which was 98% pure by LC/MS (retention time=3.32 min.; M$^+$=476.27. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

EXAMPLE 4

Preparation of N-[3-[[[(Cyanoamino)[[2-(1H-imidazol-4-yl)ethyl]amino]methylene]-amino]methyl]phenyl]-N'-[3-methoxy-4-(5-oxazolyl)phenyl]urea

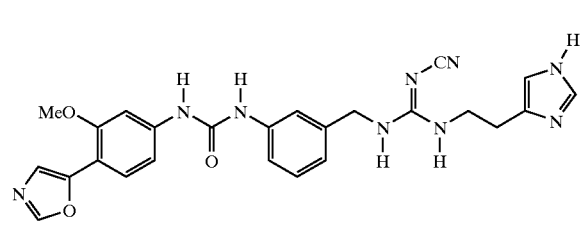

To 1 (0.012 g, 0.025 mmol) in 4 mL of acetonitrile was added histamine (3.0 mg, 0.025 mmol). The mixture was heated at reflux for 16 h, cooled to room temperature, and the solvent was removed under reduced pressure. The resulting residue was washed with ether and methylene chloride to give a white solid. The mixture was subjected to preparative HPLC to give 2.8 mg of 4 as a yellow solid which was 100% pure by HPLC (retention time=3.01 min.; M$^+$=500.30. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

EXAMPLE 5

Preparation of N-[3-[[[(Cyanoamino)(4-hydroxy-1-piperidinyl)methylene]amnino]-methyl]phenyl]-N-'[3-methoxy-4-(5-oxazoly)phenyl]area

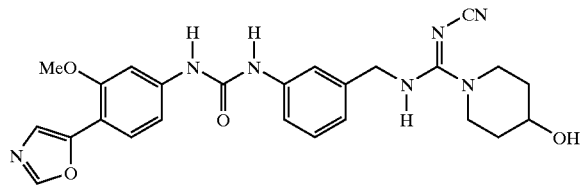

A mixture of 1 (0.010 g, 0.021 mmol) and 4-hydroxypiperidine in 3 mL of acetonitrile in a sealed tube was heated at approximately 100° C. for 48 h. After the reaction had cooled, the solvent was removed under reduced pressure. The resulting residue was washed with ether and dichloromethane to give 10 mg of a yellow solid residue which was 71% pure by HPLC. The mixture was subjected to preparative HPLC to give 4.0 mg of 5 as a yellow oil, which was 96% pure by LC/MS (retention time=3.16) (M+H)$^+$ 490.3+. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

EXAMPLE 6

Preparation of N-[3-[[[(Cyanoamino)(3-hydroxy-1-piperidinyl)methylene]amino]-methyl]phenyl]-N'-[3-methoxy-4-(5-oxazolyl)phenyl]urea

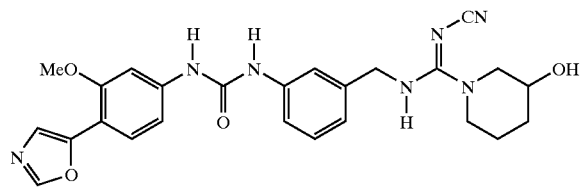

A mixture of 1 (0.010 g, 0.021 mmol) and 3-hydroxypiperidine in 3 mL of acetonitrile in a sealed tube was heated at approximately 100° C. for 48 h. After the reaction had cooled, the solvent was removed under reduced pressure. The resulting residue was washed with ether and dichloromethane to give a yellow solid. The mixture was subjected to preparative HPLC to give 3.4 mg of 6 as a yellow solid which was 100% pure by LC/MS (retention time=3.17 min; (M+H)$^+$490.3$^+$. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

EXAMPLE 7

Preparation of N-[3-[[[(Cyanoamino)(cyclohexylamino)methylene]amino]methyl]-phenyl]-N'-[3-methoxy-4-(5-oxazolyl)phenyl]urea

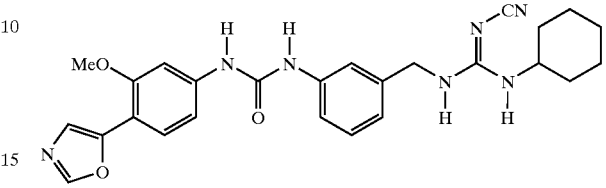

A mixture of 1 (0.015 g, 0.031 mmol) and cyclohexylamine (4.30 μL, 0.037 mmol) in 4 mL of acetonitrile in a sealed tube was heated at 110° C. for 48 h. After the reaction had cooled, the solvent was removed under reduced pressure. The resulting residue was washed with ether and dichloromethane to give a residue which contained 72% of 7 by HPLC. The mixture was subjected to preparative HPLC to give 5.30 mg (35%) of the product as a pale yellow solid which was 100% pure by LC/MS (retention time=4.18 min.; M$^+$=488.25. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

EXAMPLE 8

Preparation of N-[3-[[[(Cyanoamino)[(4-pyridinylmethyl)amino]methylene]amino]-methyl]phenyl]-N'-[3-methoxy-4-(5-oxazolyl)phenyl]urea

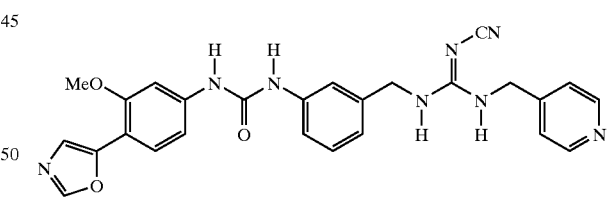

A mixture of 1 (0.015 g, 0.031 mmol) and 4-(aminomethyl)pyridine (3.80 μL, 0.037 mmol) in 4 mL of acetonitrile in a sealed tube was heated at 110° C. for 48 h. After the reaction had cooled, the solvent was removed under reduced pressure. The resulting residue was washed with ether and subjected to preparative HPLC to give 5.00 mg (33%) of 8 as an orange solid which was 100% pure by LC/MS (retention time=3.05 min.; M$^+$=497.26. Column: YMC 5ODS 4.6×5.0 mm Ballistic. Solvent A=10% MeOH, 90% H$_2$O, 0.1% TFA; Solvent B=90% MeOH, 10% H$_2$O, 0.1% TFA).

EXAMPLE 9

Preparation of N-[3-[[[(Cyanoamino)[[(tetrahydro-2-fuaranyl)methyl]amino]methylene]-amino]methyl]phenyl]-N'-[3-methoxy-4-(5-oxazolyl)phenyl]urea

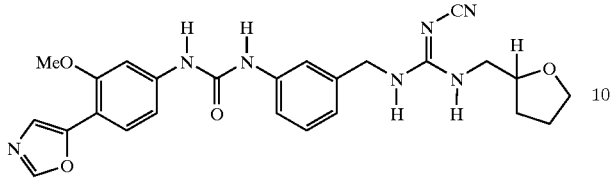

A mixture of 1 (0.015 g, 0.031 mmol) and tetrahydrofurfurylamine (3.90 μL, 0.037 mmol) in 4 mL of acetonitrile in a sealed tube was heated at 110° C. for 48 h. After the reaction had cooled, the solvent was removed under reduced pressure. The resulting residue was washed with ether, washed with dichloromethane, and subjected to preparative HPLC to give 4.3 mg (29%) of 9 as a yellow solid which was 98% pure by LC/MS (retention time=3.65 min.; $M^+$=490.23. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

EXAMPLE 10

Preparation of N-[3-[[[(Cyanoamino)[4-(2-hydroxyethyl)-1-piperazinyl]methylene]-amino]methyl]phenyl]-N'-[3-methoxy-4-(5-oxazolyl)phenyl]urea

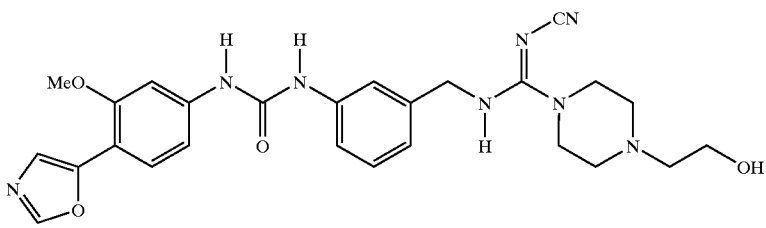

A mixture of 1 (0.031 g, 0.021 mmol) and 1-(2-hydroxyethyl)piperazine (4.60 μL, 0.037 mmol) in 4 mL of acetonitrile in a sealed tube was heated at 110° C. for 18 h. After the reaction had cooled, the solvent was removed under reduced pressure. The resulting residue was washed with ether and dichloromethane to give a residue which contained 78% of 10 by HPLC. The mixture was subjected to preparative HPLC to give 3.80 mg (24%) of the product as a pale yellow solid which was 96% pure by LC/MS (retention time=3.10 min.; $M^+$=519.30. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

EXAMPLE 11

Preparation of N-[3-[[[(Cyanoamino)(methylamino)methylene]amino]methyl]phenyl]-N'-[3-methoxy-4-(5-oxazolyl)phenyl]urea

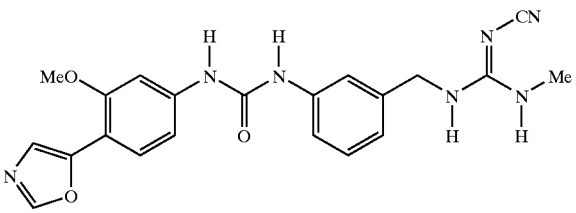

A mixture of 1 (0.020 g, 0.042 mmol) and methylamine (0.10 mL of a 2.0 M solution in THF, 0.21 mmol) in 4 mL of acetonitrile in a sealed tube was heated at 102° C. for 48 h. After the reaction had cooled, the solvent was removed under reduced pressure. The resulting residue was washed with ether, washed with dichloromethane, and subjected to preparative HPLC to give 4.8 mg (28%) of 11 as a white solid which was 99% pure by LC/MS (retention time=3.42 min.; $M^+$=420.19. Column: Shimadzu S5 C18 4.6×50 mm Ballistic. Solvent A=10% MeOH, 90% $H_2O$, 0.1% TFA; Solvent B=90% MeOH, 10% $H_2O$, 0.1% TFA).

EXAMPLE 12

Preparation of (S)-N-[3-[[[(Cyanoamino)[(tetrahydro-2-furanylmethyl)amino]-methylene]amino]methyl]phenyl]-N'-[3-methoxy-4-(5-oxazolyl)phenyl]urea

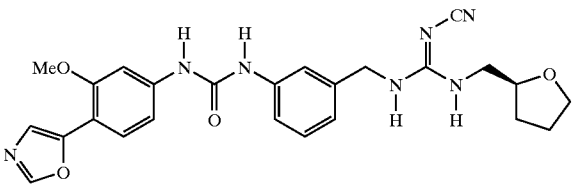

A mixture of 1 (0.020 g, 0.042 mmol) and (S)-(+)-tetrahydrofurfurylamine (5.1 μL, 0.050 mmol) in 4 mL of acetonitrile in a sealed tube was heated at 102° C. for 65 h. After the reaction had cooled, the solvent was removed under reduced pressure. The resulting residue was washed with ether, washed with dichloromethane, and subjected to preparative HPLC to give 1.44 mg of 12 as a white solid which was 98% pure by LC/MS (retention time=3.69 min.; M+=490.26. Column: Shimadzu S5 C18 4.6×50 mm Ballistic. Solvent A=10% MeOH, 90% H₂O, 0.1% TFA; Solvent B=90% MeOH, 10% H₂O, 0.1% TFA).

EXAMPLE 13

Preparation of (R)-N-[3-[[[(Cyanoamino)[(tetrahydro-2-furanylmethyl)amino]-methylene]amino]methyl]phenyl]-N'-[3-methoxy-4-(5-oxazolyl)phenyl]urea

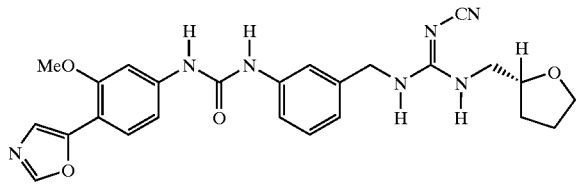

A mixture of 1 (0.020 g, 0.042 mmol) and (R)-(-)-tetrahydrofurfurylamine (5.1 μL, 0.050 mmol) in 4 mL of acetonitrile in a sealed tube was heated at 102° C. for 65 h. After the reaction had cooled, the solvent was removed under reduced pressure. The resulting residue was washed with ether, washed with dichloromethane, and subjected to preparative HPLC to give 4.7 mg (24%) of 13 as a white solid which was 98% pure by LC/MS (retention time=3.69 min.; M+=490.26. Column: Shimadzu S5 C18 4.6×50 mm Ballistic. Solvent A=10% MeOH, 90% H₂O, 0.1% TFA; Solvent B=90% MeOH, 10% H₂O, 0.1% TFA).

EXAMPLE 14

Preparation of N-[3-[[[(Cyanoamino)[(tetrahydro-2-furanyl)methoxy]methylene]amino]-methyl]phenyl]-N'-[3-methoxy-4-(5-oxazolyl)phenyl]urea

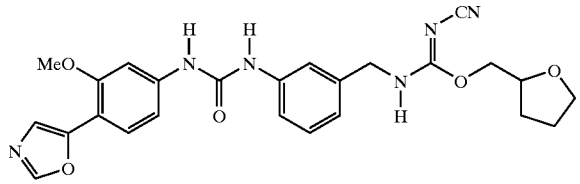

To a mixture of 1 (0.040 g, 0.042 mmol) and tetrahydrofurfuryl alcohol (16.1 μL, 0.166 mmol) in 7 mL of anhydrous tetrahydrofuran at room temperature was added 60% NaH (13.0 mg, 0.332 mmol). The mixture was heated overnight at reflux, and then quenched with a small amount of water. The organic layer was carefully collected, and the aqueous residue was extracted several times with ethyl acetate. The organic layer was dried over anhydrous sodium sulfate and concentrated under reduced pressure. Preparative HPLC of the residue provided 12.1 mg (30%) of 14 as a white solid which was 99% pure by LC/MS (retention time=3.84 min.; M+=491.19. Column: Shimadzu S5 C18 4.6×50 mm Ballistic. Solvent A=10% MeOH, 90% H₂O, 0.1% TFA; Solvent B=90% MeOH, 10% H₂O, 0.1% TFA).

EXAMPLE 15

Preparation of N-Cyano-N'-cyclohexyl-N"-[3-methoxy-4-(5-oxazolyl)phenyl]guanidine

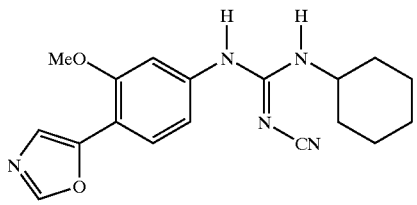

15A. Preparation of N-Cyano-N'-[3-methoxy-4-(5-oxazolyl)phenyl]carbamimidic acid phenyl ester

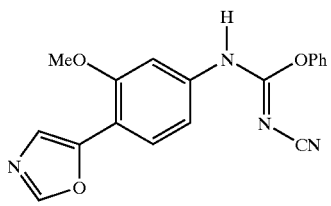

A mixture of 1D (0.200 g, 1.05 mmol) and diphenyl cyanocarbonimidate (0.258 g, 1.05 mmol) in 10 mL of acetonitrile was stirred at reflux for 40 h. As the reaction mixture cooled to room temperature, a yellow solid precipitated out of solution. The volume of solvent was reduced by half, and ether was added. Vacuum filtration afforded 0.330 g (94%) of 15A as a pale yellow solid which was 97% pure by LC/MS (retention time=3.48 min.; M+=335.15. Column: YMC S5 ODS 4.6×5.0 mm Ballistic. Solvent A=10% MeOH, 90% H₂O, 0.1% TFA; Solvent B=90% MeOH, 10% H₂O, 0.1% TFA).

15B. N-Cyano-N'-cyclohexyl-N"-[3-methoxy-4-(5-oxazolyl)phenyl]guanidine

A mixture of 15A (0.020 g; 0.060 mmol) and cyclohexylamine (7.00 μL, 0.060 mmol) in 4 mL of acetonitrile was heated in a sealed tube at approximately 100° C. for 16 h. The reaction mixture was cooled, and the solvent was removed under reduced pressure to give a yellow solid. Purification by silica gel chromatography afforded 18.4 mg (92%) of 15 as a pale yellow solid. The product was 95% pure by LC/MS (retention time=3.50 min.; M+=340.27. Column: YMC S5 ODS 4.6×5.0 mm Ballistic. Solvent A=10% MeOH, 90% H₂O, 0.1% TFA; Solvent B=90% MeOH, 10% H₂O, 0.1% TFA).

EXAMPLE 16

Preparation of (R)-N-Cyano-N'-(1-cyclohexylethyl)-N"-[3-methoxy-4-(5-oxazolyl)-phenyl]guanidine

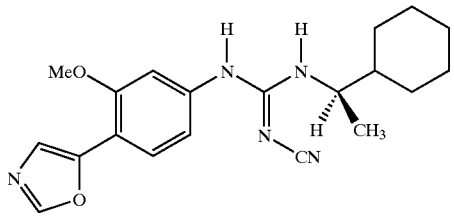

A mixture of 15A (0.015 g, 0.045 mmol) and R-(+)-1-cyclohexylethylamine (6.70 μL, 0.045 mmol) in 4 mL of acetonitrile was subjected to the same procedure used in the preparation of 15 to give 12.0 mg (73%) of 16 as a pale yellow solid. The product was 92% pure by LC/MS (retention time=3.83 min.; M+=368.35. Column: YMC S5 ODS 4.6×5.0 mm Ballistic. Solvent A=10% MeOH, 90% H₂O, 0.1% TFA; Solvent B=90% MeOH, 10% H₂O, 0.1% TFA).

EXAMPLE 17

Preparation of N-Cyano-N'-[3-methoxy-4-(5-oxazolyl)phenyl]-N"-propylguanidine

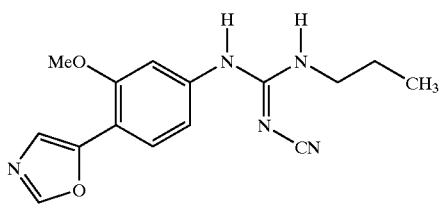

A mixture of 15A (0.015 g, 0.045 mmol) and propylamine (18.5 μL, 0.225 mmol) in 4 mL of acetonitrile was subjected to the same procedure used in the preparation of 15 to give 12.1 mg (93%) of 17 as a yellow solid. The product was 94% pure by LC/MS (retention time=2.97 min.; M+=300.22. Column: YMC S5 ODS 4.6×5.0 mm Ballistic. Solvent A=10% MeOH, 90% H₂O, 0.1% TFA; Solvent B=90% MeOH, 10% H₂O, 0.1% TFA).

EXAMPLE 18

Preparation of N-Cyano-N'-(2,3-dihydro-1H-inden-2-yl)-N"-[3-methoxy-4-(5-oxazolyl)-phenyl]guanidine

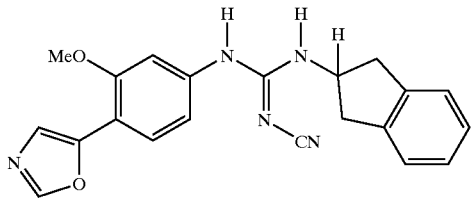

A mixture of 15A (0.015 g, 0.045 mmol) and 2-amino-indane (6.00 mg, 0.045 mmol) in 4 mL of acetonitrile was subjected to the same procedure used in the preparation of 15 to give 17.0 mg (100%) of 18 as a tan solid. The product was 95% pure by LC/MS (retention time=3.57 min.; M+=374.30. Column: YMC S5 ODS 4.6×5.0 mm Ballistic. Solvent A=10% MeOH, 90% H₂O, 0.1% TFA; Solvent B=90% MeOH, 10% H₂O, 0.1% TFA).

EXAMPLE 19

Preparation of N-Cyano-N'-cyclopentyl-N"-[3-methoxy-4-(5-oxazolyl)phenyl]guanidine

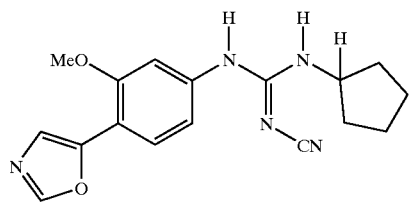

A mixture of 15A (0.015 g, 0.045 mmol) and cyclopentylamine (4.40 μL, 0.045 mmol) in 4 mL of acetonitrile was subjected to the same procedure used in the preparation of 15 to give 14.1 mg (97%) of 19 as a pale yellow solid. The product was 91.3% pure by LC/MS (retention time=3.28 min.; M+=326.26. Column: YMC S5 ODS 4.6×5.0 mm Ballistic. Solvent A=10% MeOH, 90% H2O, 0.1% TFA; Solvent B=90% MeOH, 10% H₂O, 0.1% TFA).

Example 20

Preparation of N-Cyano-N'-[3-methoxy-4-(5-oxazolyl)phenyl]-N"-[(5-methyl-2-furanyl)methyl]guanidine

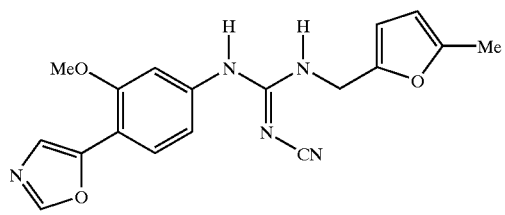

A mixture of 15A (0.015 g, 0.045 mmol) and 5-methyl-2-furanmethanamine (5.00 mg, 0.045 mmol) in 4 mL of acetonitrile was subjected to the same procedure used in the preparation of 15 to give a mixture that contained 77% of 20 and 13% of 18 by HPLC. The mixture was subjected to preparative HPLC to give 8.3 mg (53%) of the product as a pale yellow solid which was 100% pure by LC/MS (retention time=3.24 min.; M+=352.18. Column: YMC S5 ODS 4.6×5.0 mm Ballistic. Solvent A=10% MeOH, 90% H₂O, 0.1% TFA; Solvent B=90% MeOH, 10% H₂O, 0.1% TFA).

Example 21

Preparation of N-Cyano-N'-[3-methoxy-4-(5-oxazolyl)phenyl]-N"-(2-thienylmethyl)guanidine

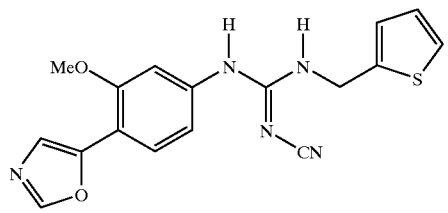

A mixture of 15A (0.015 g, 0.045 mmol) and 2-aminomethylthiophene (5.10 mg, 0.045 mmol) in 4 mL of acetonitrile was subjected to the same procedure used in the preparation of 15 to give 13.5 mg (85%) of 21 as a pale yellow solid. The product was 88% pure by LC/MS (retention time=3.16 min.; M+=354.24. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

Example 22

Preparation of N-Cyano-N'-[3-methoxy-4-(5-oxazolyl)phenyl]-N''-[(2-methylphenyl)methyl] guanidine

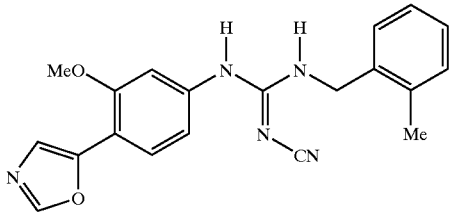

A mixture of 15A (0.015 g, 0.045 mmol) and 2-methylbenzylamine (5.60 µL, 0.045 mmol) in 4 mL of acetonitrile was subjected to the same procedure used in the preparation of 15 to give 13.9 mg (86%) of 22 as a pale yellow solid. The product was 86% pure by LC/MS (retention time=3.48 min.; M+=362.28. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

Example 23

Preparation of N-Cyano-N'-[3-methoxy-4-(5-oxazolyl)phenyl]-N'-[(3-methylphenyl)methyl] guanidine

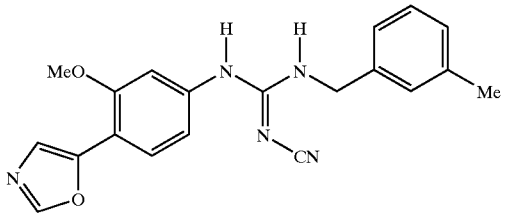

A mixture of 15A (0.015 g, 0.045 mmol) and 3-methylbenzylamine (5.60 µL, 0.045 mmol) in 4 mL of acetonitrile was subjected to the same procedure used in the preparation of 15 to give 14.6 mg (90%) of 23 as a pale yellow solid. The product was 84% pure by LC/MS (retention time=3.51 min.; M+=362.28. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

Example 24

Preparation of N-[(2-Bromophenyl)methyl]-N'-cyano-N''-[3-methoxy-4-(5-oxazolyl)phenyl] guanidine

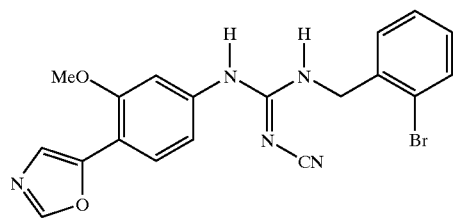

A mixture of 15A (0.015 g, 0.045 mmol) and 2-bromobenzylamine (8.40 mg, 0.045 mmol) in 4 mL of acetonitrile was subjected to the same procedure used in the preparation of 15 to give 17.8 mg (93%) of 24 as a pale yellow solid. The product was 94% pure by LC/MS (retention time=3.54 min.; M+=426.10 and 428.10. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

Example 25

Preparation of N-[(4-Chlorophenyl)methyl]-N'-cyano-N''-[3-methoxy-4-(5-oxazolyl)phenyl] guanidine

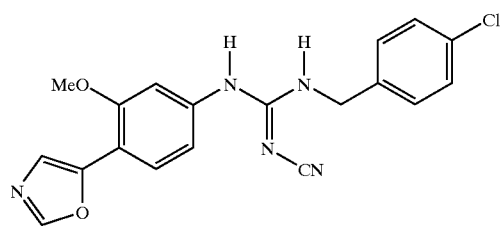

A mixture of 15A (0.015 g, 0.045 mmol) and 4-chlorobenzylamine (5.50 µL, 0.045 mmol) in 4 mL of acetonitrile was subjected to the same procedure used in the preparation of 15 to give 15.1 mg (88%) of 25 as a pale yellow solid. The product was 95% pure by LC/MS (retention time=3.54 min.; M+=382.12. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

Example 26

Preparation of N-(Bicyclo[2.2.1]heptan-2-yl)-N'-cyano-N"-[3-methoxy-4-(5-oxazolyl)-phenyl]guanidine

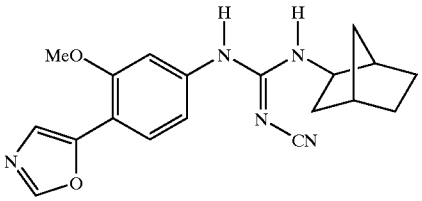

A mixture of 15A (0.015 g, 0.045 mmol) and (+/−)-exo-2-aminoborane (5.00 mg, 0.045 mmol) in 4 mL of acetonitrile was subjected to the same procedure used in the preparation of 15 to give 14.7 mg (93%) of 26 as a pale yellow solid. The product was 91% pure by LC/MS (retention time=3.59 min.; $M^+$=352.21. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

Example 27

Preparation of N-Cyano-N'-[3-methoxy-4-(5-oxazolyl)phenyl]-N"-(4-methylcyclohexyl)-guanidine

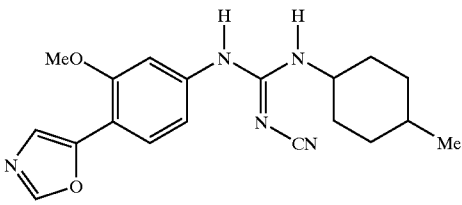

A mixture of 15A (0.015 g, 0.045 mmol) and 4-methylcyclohexylamine (5.90 μL, 0.045 mmol) in 4 mL of acetonitrile was subjected to the same procedure used in the preparation of 15 to give 15.3 mg (96%) of 27 as a pale yellow solid. The product was 96% pure by LC/MS (retention time=3.73 min.; $M^+$=354.25. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

Example 28

Preparation of N-Cyano-N'-[3-methoxy-4-(5-oxazolyl)phenyl]-N"-(3-methylbutyl)guanidine

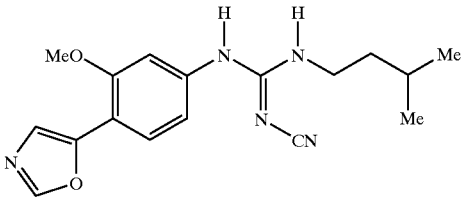

A miture of 15A (0.015 g, 0.045 mmol) and isoamylamine (5.20 μL, 0.045 mmol) in 4 mL of acetonitrile was subjected to the same procedure used in the preparation of 15 to give 12.0 mg (82%) of 28 as a pale yellow solid. The product was 94% pure by LC/MS (retention time=3.49 min.; $M^{30}$=328.19. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

Example 29

Preparation of N-[(4-Aminophenyl)methyl]-N'-cyano-N'-[3-methoxy-4-(5-oxazolyl)phenyl]guanidine

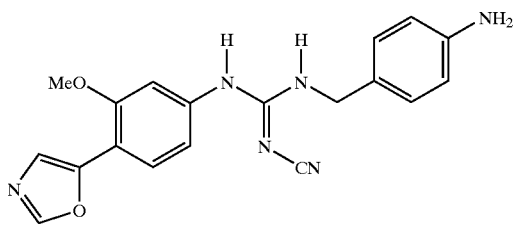

A mixture of 15A (0.015 g, 0.045 mmol) and 4-aminobenzylamine (5.10 μL, 0.045 mmol) in 4 mL of acetonitrile was subjected to the same procedure used in the preparation of 15 to give 16.3 mg (100%) of 29 as a yellow solid. The product was 92% pure by LC/MS (retention time=2.27 min.; $M^+$=363.21. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

Example 30

Preparation of N-Cyano-N'-(cyclopropylmethyl)-N"-[3-methoxy-4-(5-oxazolyl)phenyl]-guanidine

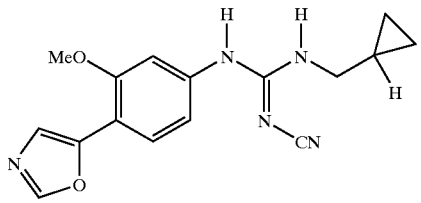

A mixture of 15A (0.015 g, 0.045 mmol) and aminomethylcyclopropane (4.00 μL, 0.045 mmol) in 4 mL of acetonitrile was subjected to the same procedure used in the preparation of 15 to give 13.2 mg (94%) of 30 as a pale yellow solid. The product was 99% pure by LC/MS (retention time=3.06 min.; $M^+$=312.17. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

Example 31

Preparation of N-Butyl-N'-cyano-N''-[3-methoxy-4-(5-oxazolyl)phenyl]guanidine

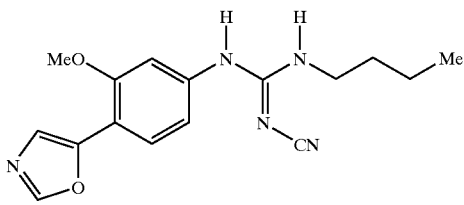

A mixture of 15A (0.015 g, 0.045 mmol) and n-butylamine (4.40 μL, 0.045 mmol) in 4 mL of acetonitrile was subjected to the same procedure used in the preparation of 15 to give 14.1 mg (100%) of 31 as a pale yellow solid. The product was 96% pure by LC/MS (retention time=3.25 min.; M$^+$=314.18. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

Example 32

Preparation of N-[(3-Chlorophenyl)methyl]-N'-cyano-N''-[3-methoxy-4-(5-oxazolyl)phenyl]guanidine

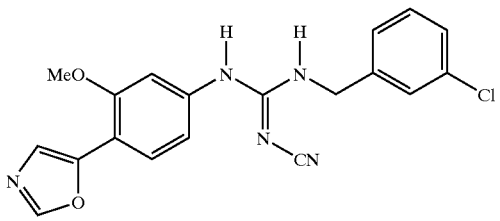

A mixture of 15A (0.015 g, 0.045 mmol) and 3-chlorobenzylamine (5.50 μL, 0.045 mmol) in 4 mL of acetonitrile was subjected to the same procedure used in the preparation of 15 to give 16.1 mg (94%) of 32 as a pale yellow solid. The product was 91% pure by LC/MS (retention time=3.55 min.; M$^+$=382.14. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

Example 33

Preparation of N-Cyano-N'-[4-(1,1-dimethylethyl)cyclohexyl]-N''-[3-methoxy-4-(5-oxazolyl)phenyl]guanidine

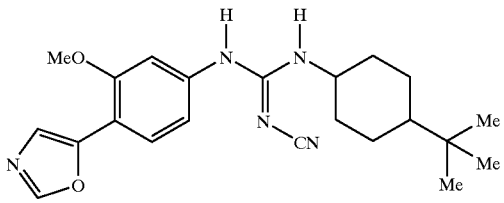

A mixture of 15A (0.015 g, 0.045 mmol) and 4-tert-butylcyclohexylamine (8.40 μL, 0.045 mmol) in 4 mL of acetonitrile was subjected to the same procedure used in the preparation of 15 to give 15.0 mg (84%) of 33 as a pale yellow solid. The product was 96% pure by LC/MS (retention time=4.20 min.; M$^+$=396.28. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

Example 34

Preparation of N-Cyano-N'-(3-methoxy-4-(5-oxazolyl)phenyl)-N''-phenylguanidine

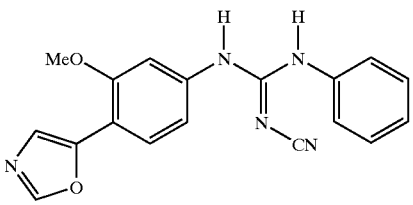

34A. Preparation of 3-Methoxy-4-(5-oxazolyl)phenyl Isothiocyanate

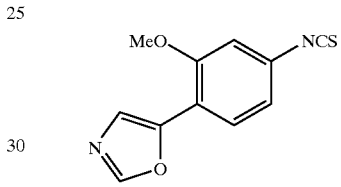

3-Methoxy-4-(5-oxazolyl)aniline, 1D, (3.50 g, 18.4 mmol) and 1,1'-thiocarbonyldi-2(2H)-pyridone (4.41 g, 18.4 mmol) in dichloromethane (100 mL) were stirred at rt for 3 h. The solvent was evaporated under vacuum, and the residue was subjected to a short column (30% AcOEt/hexane) to afford 34A (4.02 g, 94% yield) as white flakes.

34B. Preparation of Sodium Cyanamide

To a solution of cyanamide (3.00 g, 71.4 mmol) in methanol (30 mL) was introduced sodium methoxide (0.5 M methanol solution, 142.8 mL, 71.4 mmol) at rt over 25 min, and the resulting solution was stirred at rt for 2 h. Evaporation of the solvent gave 34B (4.57 g, 100% yield) as a white solid.

34C. Preparation of the Sodium salt of N-cyano-N'-(3-Methoxy-4-(5-oxazolyl)phenyl)-thiourea

To a solution of isothiocyanate 34A (2.50 g, 10.8 mmol) in absolute ethanol (150 mL) was added sodium cyanamide 34B (691 mg, 10.8 mmol) in absolute ethanol (100 mL) at rt over 30 min. The resulting solution was stirred at rt for 4 h. Most of the solvent was evaporated under vacuum, and to the remaining residue was added dichloromethane (60 mL). The precipitate was collected by filtration, followed by washing with dichloromethane (3 times) to provide 34C (2.15 g, 67% yield) as a white solid.

34D. Preparation of N-Cyano-N'-(3-methoxy-4-(5-oxazolyl)phenyl)-N"-phenylguanidine A mixture of thiouronium salt 34C (80 mg, 0.270 mmol), 1-ethyl-3-(3-dimethylaminopropyl)carbodiimide hydrochloride (104 mg, 0.540 mmol), and aniline (49.2 μL, 0.540 mmol) in DMF (5 mL) was stirred at 50° C. for 15 h before it was cooled to rt, neutralized with 5% HCl (5 mL), and diluted with AcOEt (60 mL). The solution was then washed with water and brine and dried over anhydrous $MgSO_4$. Purification by silica gel chromatography (4% MeOH/$CHCl_3$) gave 34 (51 mg, 57% yield) as a slightly yellow solid (LC/MS retention time=3.14 min.; $M^+$=334. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

Example 35

Preparation of N-Cyano-N'-(3-methoxy-4-(5-oxazolyl)phenyl)-N"-(2-methylphenyl)guanidine

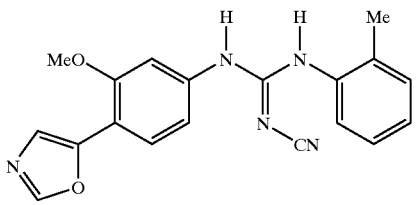

A mixture of thiouronium salt 34C (60 mg, 0.202 mmol), 1-ethyl-3-(3-dimethylaminopropyl)carbodiimide hydrochloride (77.4 mg, 0.404 mmol), and o-toluidine (43.1 μL, 0.404 mmol) in DMF (4 mL) was subjected to the same procedure described in step 34D to afford 35 (35 mg, 50% yield) as a pale yellow solid (LC/MS retention time=3.17 min.; $M^+$=348. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

Example 36

Preparation of N-Cyano-N'-(3-methoxy-4-(5-oxazolyl)phenyl)-N"-(4-methylphenyl)guanidine

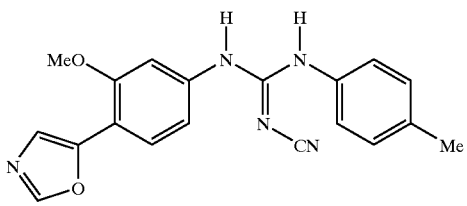

A mixture of thiouronium salt 34C (60 mg, 0.202 mmol), 1-ethyl-3-(3-dimethylaminopropyl)carbodiimide hydrochloride (77.4 mg, 0.404 mmol), and p-toluidine (43.3 μL, 0.404 mmol) in DMF (4 mL) was subjected to the same procedure described in step 34D to afford 36 (45 mg, 64% yield) as a white (LC/MS retention time=3.60 min.; $M^+$=348. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

Example 37

Preparation of N-Cyano-N'-[3-methoxy-4-(5-oxazolyl)phenyl]-N"-[3-(1-methylethyl)phenyl] guanidine

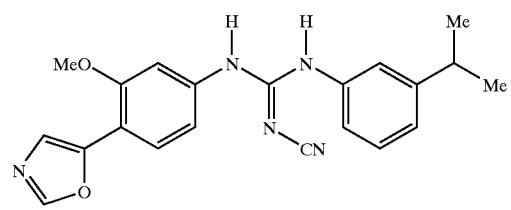

A mixture of thiouronium salt 34C (60 mg, 0.202 mmol), 1-ethyl-3-(3-dimethylaminopropyl)carbodiimide hydrochloride (77.4 mg, 0.404 mmol), and 3-isopropylaniline (55.0 μL) in DMF (4 mL) was subjected to the same procedure described in step 34D to afford 37 (38 mg, 50% yield) as a white solid (LC/MS retention time=3.72 min.; $M^+$=376. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

Example 38

Preparation of N-Cyano-N'-[3-methoxy-4-(5-oxazolyl)phenyl]-N"-[3-(trifluoromethoxy)-phenyl] guanidine

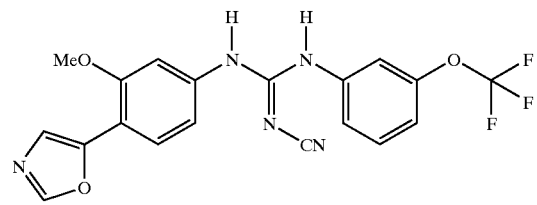

A mixture of thiouronium salt 34C (60 mg, 0.202 mmol), 1-ethyl-3-(3-dimethylaminopropyl)carbodiimide hydrochloride (77.4 mg, 0.404 mmol), and 3-trifluoromethoxyaniline (55.1 μL, 0.404 mmol) in DMF (4 mL) was subjected to the same procedure described in step 34D to afford 38 (16 mg, 19% yield) as a white solid. MS: 418 ($M^+$+1), RT: 3.72 min. (LC/MS retention time=3.72 min.; $M^+$=418. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

Example 39

Preparation of N-Cyano-N'-[3-(1,1-dimethylethyl)phenyl]-N"-[3-methoxy-4-(5-oxazolyl)phenyl]guanidine

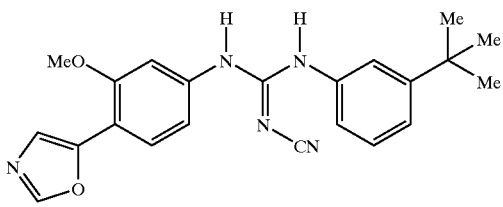

A mixture of thiouronium salt 34C (30 mg, 0.101 mmol), 1-ethyl-3-(3-dimethylaminopropyl)carbodiimide hydrochloride (37.2 mg, 0.202 mmol), and 3-tert-butylaniline (30.1 mg, 0.208 mmol) in DMF (3 mL) was subjected to the same procedure described in step 34D. The resulting mixture was subjected to preparative HPLC to afford 39 (19 mg, 89% purity, 49% yield) as a white solid (LC/MS retention time=3.86 min.; $M^+$=390. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

Example 40

Preparation of N-Cyano-N'-[3-methoxy-4-(5-oxazolyl)phenyl]-N"-[3-(2-phenoxyethoxy)phenyl]guanidine

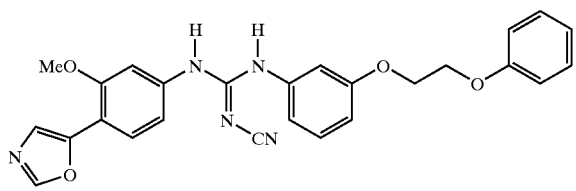

A mixture of thiouronium salt 34C (30 mg, 0.101 mmol), 1-ethyl-3-(3-dimethylaminopropyl)carbodiimide hydrochloride (37.2 mg, 0.202 mmol), and 3-(2-phenoxyethoxy)aniline (46.3 mg, 0.202 mmol) in DMF (3 mL) was subjected to the same procedure described in step 34D to afford 40 (6.0 mg, 82% purity, 10% yield) as a white solid (LC/MS retention time 3.77 min.; $M^+$=470. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

Example 41

Preparation of N-Cyano-N'-[3-(hydroxymethyl)phenyl]-N"-[3-methoxy-4-(5-oxazolyl)phenyl]guanidine

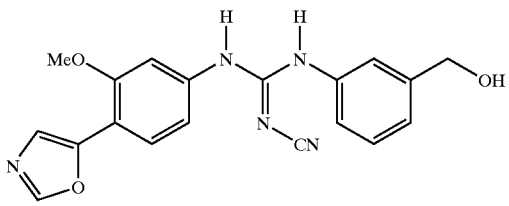

A mixture of thiouronium salt 34C (30 mg, 0.101 mmol), 1-ethyl-3-(3-dimethylaminopropyl)carbodiimide hydrochloride (37.2 mg, 0.202 mmol), and m-aminobenzyl alcohol (25.0 mg, 0.203 mmol) in DMF (3 mL) was subjected to the same procedure described in step 34D to afford 41 (16.0 mg, 44 10% yield) as a white solid (LC/MS retention time=2.98 min.; $M^+$=364. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

Example 42

Preparation of Trans-N-Cyano-N'-[3-methoxy-4-(5-oxazolyl)phenyl]-N"-(2-phenylcyclopropyl)guanidine

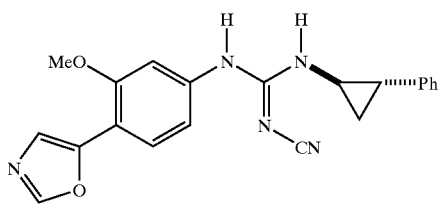

To a solution of trans-2-phenylcyclopropylamine hydrochloride (34.2 mg, 0.202 mmol) in DMF (3 mL) was added triethylamine (33.8 μL). The solution was stirred at rt for 10 min and then added to a mixture of thiouronium salt 34C (30 mg, 0.101 mmol) and 1-ethyl-3-(3-dimethylaminopropyl)carbodiimide hydrochloride (37.2 mg, 0.202 mmol). The resulting solution was heated at 50° C. for 15 h, cooled to rt, neutralized with 5% HCl, diluted with AcOEt, washed with brine, and dried over anhydrous $MgSO_4$. After the solvent was evaporated, the residue was washed with methanol to give 42 (11.0 mg, 29% yield) as a white solid (LC/MS retention time=3.77 min.; $M^+$=374. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

Example 43

Preparation of N-Cyano-N'-[3-methoxy-4-(5-oxazolyl)phenyl]-N"-3-pyridinylguanidine

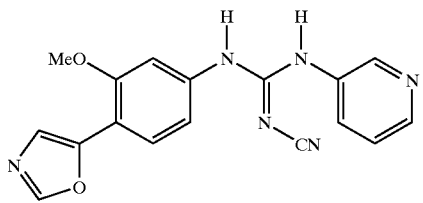

A mixture of thiouronium salt 34C (30 mg, 0.101 mmol), 1-ethyl-3-(3-dimethylaminopropyl)carbodiimide hydrochloride (37.2 mg, 0.202 mmol), and 3-aminopyridine (20.0 mg, 0.212 mmol) in DMF (3 mL) was stirred at 50° C. for 15 h and then at 80° C. for another 15 h. The solution was then diluted with AcOEt, washed with water and brine, and dried over anhydrous $MgSO_4$. Purification by preparative HPLC gave 43 in the form of a TFA salt (4.0 mg, 13% yield) as a white solid (LC/MS retention time=2.15 min.; $M^+$=335. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

Example 44

Preparation of (S)-[[3-[[(Cyanoamino)[[3-methoxy-4-(5-oxazolyl)phenyl]amino]methylene]amino]phenyl]methyl]carbamic Acid Tetrahydro-3-furanyl Ester

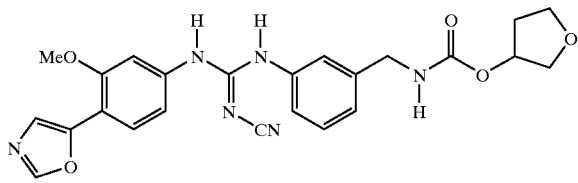

44A. Preparation of 3-Aminobenzylamine

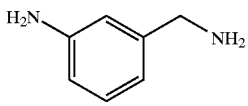

3-Cyanoaniline (0.50 g, 4.23 mmol) in 100 mL of MeOH was stirred overnight at room temperature under a $H_2$ environment in the presence of 10% Pd/C (100 mg). The Pd/C was removed by filtration through a pad of Celilte, and the resulting filtrate was concentrated under reduced pressure to give 0.516 g (~100%) of 44A as a thick oil. The product was used without any further purification.

44B. Preparation of (S)-(+)-tetrahydrofuranylchloroformate

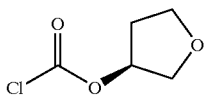

To a solution of phosgene (8 mL of a ~20% in toluene, 17.0 mmol) in 20 mL of dichloromethane at 0° C. was added a solution of (S)-(+)-hydroxytetrahydrofuran (0.50 g, 5.67 mmol) and triethylamine (1.58 mL, 11.3 mmol) in 15 mL of dichloromethane dropwise over 20 min. The reaction mixture was stirred for 15 h at room temperature. The solvent was removed under reduced pressure, and the resulting residue was dissolved in ether. The triethylamine hydrochloride salt was removed by filtration. Concentration followed by purification of the residue by silica gel chromatography afforded 0.509 g (60%) of 44B as a clear oil.

44C. Preparation of N-Methyl-(3-aminophenyl)-(+)-tetrahydrofuranylcarbamate

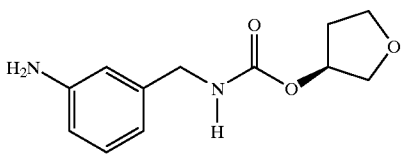

To 44B (0.509 g, 3.38 mmol) in 15 mL of dichloromethane at 0° C. was added a solution of 44A (0.517 g, 4.23 mmol) and triethylamine (0.94 mL, 6.76 mmol) in 15 mL of dichloromethane dropwise over 10 min. The reaction mixture was stirred overnight at room temperature. The solvent was removed under reduced pressure, and the residue was dissolved in ether. The solid triethylamine hydrochloride salt was removed by filtration. Concentration followed by purification of the residue by silica gel chromatography afforded 0.508g (64%) of 44C as a clear oil (LC/MS retention time=1.07 min.; $M^+$=237.19. Column: Shimadzu S5 C18 4.6×50 mm Ballistic. Solvent A=10% MeOH, 90% $H_2O$, 0.1% TFA; Solvent B=90% MeOH, 10% $H_2O$, 0.1% TFA).

44D. Preparation of (S)-[[3-[[(Cyanoamino)[[3-methoxy-4-(5-oxazolyl)phenyl]amino]-methylene]amino]phenyl]methyl]carbamic Acid Tetrahydro-3-furanyl Ester A mixture of thiouronium salt 34C (30.0 mg, 0.101 mmol), 1-ethyl-3-(3-dimethylaminopropyl)carbodiimide hydrochloride (39.0 mg, 0.202 mmol), and 44C (53.0 mg, 0.202 mmol) in DMF (1.5 mL) was stirred at 50° C. for 15 h. The reaction mixture was quenched with 5% aqueous HCl (1.5 mL) and extracted with ethyl acetate. The organic layer was collected, washed with water, washed with brine, and dried over anhydrous sodium sulfate. Concentration followed by purification by preparative HPLC afforded 17.0 mg (35%) of 44D as a white solid (LC/MS retention time=3.16 min.; $M^+$=477.23. Column: Shimadzu S5 C18 4.6×50 mm Ballistic. Solvent A=10% MeOH, 90% $H_2O$, 0.1% TFA; Solvent B=90% MeOH, 10% $H_2O$, 0.1% TFA).

Example 45

Preparation of [[3-[[(Cyanoamino)[[3-methoxy-4-(5-oxazolyl)phenyl]amino]methylene]-amino]phenyl]methyl]carbamic Acid Tetrahydro-3-furanylmethyl Ester

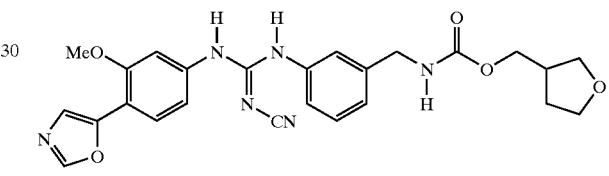

45A. Preparation of tertahydro-3-furanmethylchloroformate

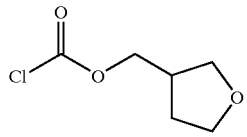

To a solution of phosgene (8 mL of a ~20% in toluene, 17.0 mmol) in 20 mL of dichloromethane at 0° C. was added a solution of tetrahydro-3-furanmethanol (0.55 mL, 5.67 mmol) and triethylamine (1.58 mL, 11.3 mmol) in 15 mL of dichloromethane dropwise over 20 min. The reaction mixture was stirred for 15 h at room temperature. The solvent was removed under reduced pressure, and the resulting residue was dissolved in ether. The triethylamine hydrochloride salt was removed by filtration. Concentration followed by purification of the residue by silica gel chromatography afforded 0.656 g (70%) of 45A as a clear oil.

45B. Preparation of N-Methyl-(3-aminophenyl)-tetrahydro-3-furanmethoxycarbamate

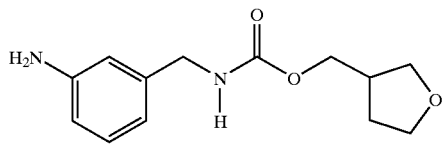

To 45A (0.328 g, 1.99 mmol) in 8 mL of dichloromethane at 0° C. was added a solution of 44A (0.258 g, 2.12 mmol)

and triethylamine (0.55 mL, 3.98 mmol) in 8 mL of dichloromethane dropwise over 10 min. The reaction mixture was stirred overnight at room temperature. The solvent was removed under reduced pressure, and the residue was dissolved in ether. The solid triethylamine hydrochloride salt was removed by filtration. Concentration followed by purification of the residue by silica gel chromatography afforded 0.314 g (63%) of 45B as a pale yellow oil (LC/MS retention time=1.06 min.; $M^+$=251.20. Column: Shimadzu S5 C18 4.6×50 mm Ballistic. Solvent A=10% MeOH, 90% $H_2O$, 0.1% TFA; Solvent B=90% MeOH, 10% $H_2O$, 0.1% TFA).

45C. Preparation of [[3-[[(Cyanoamino)[[3-methoxy-4-(5-oxazolyl)phenyl]amino]methylene]amino]phenyl]methyl] carbamic Acid Tetrahydro-3-furanyl Ester A mixture of thiouronium salt 34C (40.0 mg, 0.135 mmol), 1-ethyl-3-(3-dimethylaminopropyl)carbodiimide hydrochloride (52.0 mg, 0.270 mmol), and 45B (68.0 mg, 0.270 mmol) in DMF (2 mL) was stirred at 50° C. for 16 h. The reaction mixture was quenched with 5% aqueous HCl (2 mL) and extracted with ethyl acetate. The organic layer was collected, washed with water, washed with brine, and dried over anhydrous sodium sulfate. Concentration followed by purification by preparative HPLC afforded 14.0 mg of 45 as a white solid (LC/MS retention time=3.35 min.; $M^+$=491.28 Column: Shimadzu S5 C18 4.6×50 mm Ballistic. Solvent A=10% MeOH, 90% $H_2O$, 0.1% TFA; Solvent B=90% MeOH, 10% $H_2O$, 0.1% TFA).

Example 46

Preparation of N-[[3-[[(Cyanoamino)[[3-methoxy-4-(5-oxazolyl)phenyl]amino]methylene]amino]phenyl]methyl]-N'-[(tetrahydro-3-furanyl)methyl]urea

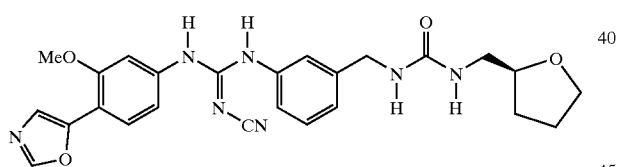

46A. Preparation of (S)-tetrahydrofurfurylisocyanate

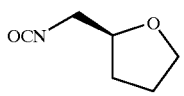

To a solution of phosgene (2 mL of a ~20% in toluene, 4.44 mmol) in 5 mL of dichloromethane at 0° C. was added a solution of (S)-tetrahydrofurfurylamine (0.15 mL, 1.48 mmol) and triethylamine (0.45 mL, 3.26 mmol) in 4 mL of dichloromethane dropwise over 20 min. The reaction mixture was stirred for 2.5 h at room temperature. The solvent was removed under reduced pressure, and the resulting residue was dissolved in ether. The triethylamine hydrochloride salt was removed by filtration. Concentration afforded 46A as a clear oil in quantitative yield.

46B. Preparation of N-[[3-aminophenyl]methyl]-N'-[(tetrahydro-3-furanyl)methyl]urea

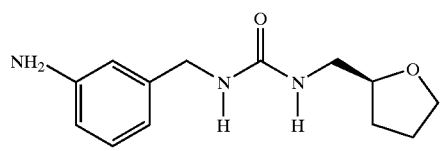

To 46A (0.188 g, 1.48 mmol) in 5 mL of dichloromethane at 0° C. was added a solution of 44A (0.258 g, 2.12 mmol) and triethylamine (0.41 mL, 2.96 mmol) in 4 mL of dichloromethane dropwise over 10 min. The reaction mixture was stirred overnight at room temperature. The solvent was removed under reduced pressure, and the residue was purified by silica gel chromatography to give 46B as a pale yellow solid (LC/MS retention time=1.20 min.; $M^+$=250.26. Column: Shimadzu S5 C18 4.6×50 mm Ballistic. Solvent A=10% MeOH, 90% $H_2O$, 0.1% TFA; Solvent B=90% MeOH, 10% $H_2O$, 0.1% TFA).

46C. Preparation of N-[[3-[[(Cyanoamino)[[3-methoxy-4-(5-oxazolyl)phenyl]amino]-methylene]amino]phenyl]methyl]-N'-[(tetrahydro-3-faranyl)methyl]urea A mixture of thiouronium salt 35C (40.0 mg, 0.135 mmol), 1-ethyl-3-(3-dimethylaminopropyl)carbodiimide hydrochloride (52.0 mg, 0.270 mmol), and 46B (67.0 mg, 0.270 mmol) in DMF (2 mL) was stirred at 50° C. for 16 h. The reaction mixture was quenched with 5% aqueous HCl (2 mL) and extracted with ethyl acetate. The organic layer was collected, washed with water, washed with brine, and dried over anhydrous sodium sulfate. Concentration followed by purification by preparative HPLC afforded 8.0 mg of 46 as a white solid (LC/MS retention time=3.23 min.; $M^+$=490.30 Column: Shimadzu S5 C18 4.6×50 mm Ballistic. Solvent A=10% MeOH, 90% $H_2O$, 0.1% TFA; Solvent B=90% MeOH, 10% $H_2O$, 0.1% TFA).

Example 47

Preparation of N-[3-[[[(Cyanoamino)methoxymethylene]amino]methyl]phenyl]-N'-[3-methoxy-4-(5-oxazolyl)phenyl]urea

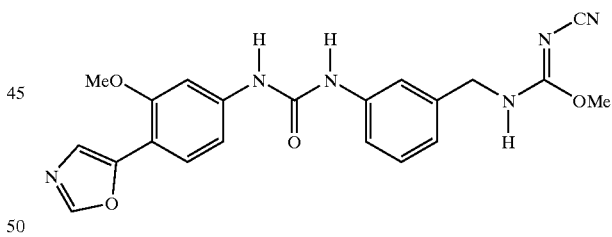

To a mixture of 1 (0.045 g, 0.093 mmol) and methanol (30 μL, 0.746 mmol) in 5 mL of anhydrous tetrahydrofuran at room temperature was added 60% NaH (14.0 mg, 0.373 mmol). The mixture was heated overnight at ~50° C. and then quenched with a small amount of saturated aqueous ammonium chloride. The organic layer was removed under reduced pressure. The resulting solid was washed with ether several times and then diluted with methanol. The sodium chloride salt was removed by filtration, and the filtrate was concentrated to give a tan solid which was washed several times with dichloromethane to give 35.8 mg (92%) of 47 as an off-white solid. The product was 100% pure by analytical HPLC with a retention time of 3.66 min (Column: YMC S5 ODS 4.6×50 mm Ballistic; Solvent A=10% MeOH, 90% $H_2O$, 0.2% $H_3PO_4$; Solvent B=90% MeOH, 10% $H_2O$, 0.2% $H_3PO_4$) and a LC/MS $M^{+1}$=421.21 (retention time=3.69 min.; Column: Shimadzu S5 C18 4.6×50 mm Ballistic. Solvent A=10% MeOH, 90% H$_2$O, 0.1% TFA; Solvent B=90% MeOH, 10% H$_2$O, 0.1% TFA).

Example 48

Preparation of N-[3-[[[(Cyanoamino)[(tetrahydro-3-furanyl)methoxy]methylene]amino]-methyl]phenyl]-N'-[3-methoxy-4-(5-oxazolyl)phenyl]urea

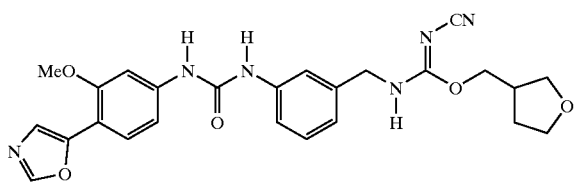

To a mixture of 1 (0.050 g, 0.104 mmol) and tetrahydro-3-furanmethanol (80 μL, 0.829 mmol) in 6.5 mL of anhydrous tetrahydrofuran at room temperature was added 60% NaH (16.6 mg, 0.415 mmol). The mixture was heated overnight at ~50° C. and then quenched with a small amount of saturated aqueous ammonium chloride. The organic layer was removed under reduced pressure. The resulting solid was washed with ether several times and then diluted with methanol. The sodium chloride salt was removed by filtration. Concentration followed by purification of the resulting residue by preparative HPLC afforded 2.9 mg of 48 as white solid. The product was 100% pure by analytical HPLC with a retention time of 3.70 min (Column: YMC S5 ODS 4.6×50 mm Ballistic; Solvent A=10% MeOH, 90% H$_2$O, 0.2% H$_3$PO$_4$; Solvent B=90% MeOH, 10% H$_2$O, 0.2% H$_3$PO$_4$) and a LC/MS M$^{+1}$=491.24 (retention time=3.72 min.; Column: Shimadzu S5 C18 4.6×50 mm Ballistic. Solvent A=10% MeOH, 90% H$_2$O, 0.1% TFA; Solvent B=90% MeOH, 10% H$_2$O, 0.1% TFA).

Example 49

Preparation of N-[3-[[Amino(cyanoamino)methylene]amino]phenyl]-N'-[3-methoxy-4-(5-oxazoly)phenyl]urea

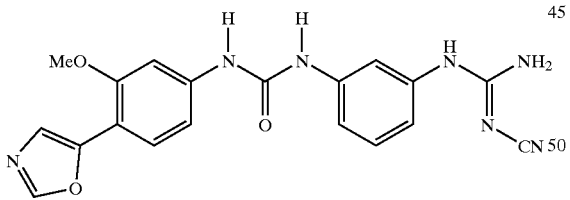

49A. Preparation of N-(3-nitrophenyl)-N'-[3-methoxy-4-(5-oxazolyl)phenyl]urea

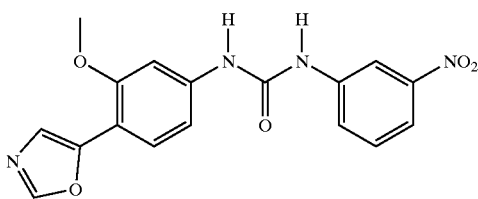

To a solution of 600 mg (3.2 mmol) of 1D in 20 ml of methylene chloride was added, as a solid, 525 mg (3.2 mmol) of m-nitrophenylisocyanate. A voluminous precipitate was obtained. Stirring was continued overnight. The precipitate was filtered and washed with methylene chloride to afford 1.1 g (3.1 mmol, 97%) of 49A as a yellow solid.

49B. Preparation of N-(3-aminophenyl)-N'-[3-methoxy-4-(5-oxazolyl)phenyl]urea

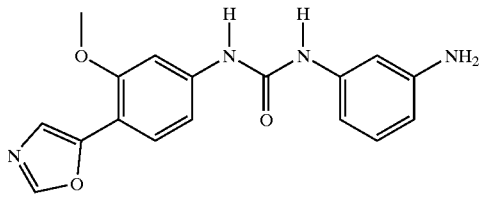

A solution of 0.7 g (2 mmol) of 49A in 60 ml of dioxane and 30 ml of methanol was hydrogenated at rt and one atmosphere pressure over 0.14 g of 10% Pd/C catalyst. The catalyst was removed by filtration through Celite. The filtrate was evaporated to dryness to yield 0.3 g of 49B as a tan solid. The filter cake was suspended in dioxane—methanol and stirred at 50° C. for 1 hr. The hot solution was again filtered, and the filtrate evaporated to dryness to yield an additional 0.6 g of material. The combined batches were triturated with methylene chloride and the insolubles filtered to give 645 mg (2 mmoles, 100%) of 49B as a light tan powder.

49C N-[3-[[Amino(cyanoamino)methylene]amino]phenyl]-N'-[3-methoxy-4-(5-oxazolyl)phenyl]urea To a solution of 50 mg (0.15 mmol) of 49B in 1 ml of DMF was added excess HCl—ether. A precipitate was obtained. Stirring was continued for 0.5 hr and the slurry was then evaporated to dryness. The residue was diluted with 2 ml of DMF and 40 mg (0.45 mmol) of sodium dicyanamide added. The reaction was heated at 50° C. for 3 hr during which time a lightly cloudy, pale yellow solution was obtained. After removal of the solvent, the residue was diluted with 3 ml of water and stirred for 1 hr. The insolubles were removed by filtration to give 76 mg of the crude product. This material was dissolved into methanol and absorbed onto approx. 1 g of silica gel and subjected to flash chromatography on a 30 cc column of silica gel. Elution with 5% MeOH-EtOAc afforded 9 mg (0.023 mmol, 15%) of 49C as a pale yellow solid. (M+H)$^+$ 392$^+$.

Although the present invention has been described in some detail by way of illustration and example for purposes of clarity and understanding, it will be apparent that certain changes and modifications may be practiced within the scope of the appended claims.

We claim:

1. A compound represented by the following formula, or a salt thereof:

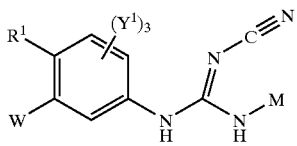

wherein:

Y$^1$ is selected from H, C$_1$–C$_3$alkyl, and halo;
W is selected from R$^1$ and R$^3$;
R$^1$ is oxazolyl having 0 to 3 substituents selected from R$^2$ and R$^3$;
R$^2$ is selected from halogen, CN, NO$_2$, CF$_3$, (C$_0$–C$_4$alkyl)OR$^3$, OCF$_3$, OC(O)R$^3$, OC(O)OR$^3$, O(C)NR³R⁴, (C₀–C₄alkyl)C(O)R³, (C₀–C₄alkyl)C(O)OR³, (C₀–C₄alkyl)C(O)NR³R⁴, (C₀–C₄ alkyl)CONR³S(O)₂R⁵, (C₀–C₄alkyl)C(O)N(OR³)R³, (C₀–C₄alkyl)SR³, C₀–C₄ alkyl)S(O)R⁵, (C₀–C₄ alkyl)S(O)₂R⁵, (C₀–C₄alkyl)S(O)₂NR³R⁴, (C₀–C₄alkyl)S(O)₂NR³C(O)R⁴, (C₀–C₄alkyl)NR³R⁴, (C₀–C₄alkyl)NR³C(O)NR³R⁴, (C₀–C₄alkyl)NR³C(O)R⁴, (C₀–C₄alkyl)NR³C(O)OR⁵, (C₁–C₄ alkyl)NR³C(O)NR₃⁵ᵃ, (C₀–C₄alkyl)NR³S(O)₂R⁵, (C₀–C₄alkyl)S(O)₂OR³, (C₀–C₄alkyl)P(O)(OH)OR³, —J—(C₀–C₄alkyl)OR³, —J—(C₁–C₄alkyl)C(O)OR³, —J—(C₁–C₄alkyl)CONR³S(O)₂R⁵, —J—(C₁–C₄alkyl)S(O)₂NR³R⁴, —J—(C₁–C₄alkyl)S(O)₂ₙᵣ³C(O)R⁴, (C₀–C₄alkyl)tetrazol-5-yl, and —J—(C₁–C₄alkyl)tetrazol-5-yl, wherein J is chosen from O, S, and NR³;

R³ is selected from hydrogen, (C₁–C₄)alkyl, (C₂–C₄)alkenyl, (C₂–C₄)alkynyl, aryl(C₀–C₄)alkyl-, heterocyclic(C₀–C₄)alkyl-, and cycloalkyl(C₀–C₄)alkyl-, wherein said groups are substituted with 0–2 substituents independently selected from R⁶;

R⁴ is selected from hydrogen, (C₁–C₄)alkyl, (C₂–C₄)-alkenyl, (C₂–C₄)alkynyl, aryl(C₀–C₄)alkyl-, heterocyclic(C₀–C₄)alkyl-, cycloalkyl, (C₀–C₄) alkylcarbonyl, aryl(C₀–C₄)alkylcarbonyl, heterocyclic(C₀–C₄)alkylcarbonyl, (C₁–C₄) alkyloxycarbonyl, aryl(C₁–C₄)alkyloxycarbonyl, and heterocyclic(C₁–C₄)alkyloxycarbonyl, wherein said groups are substituted with 0–2 substituents independently selected from R⁶;

alternatively, R³ and R⁴, when both substituents are on the same nitrogen atom, as in (—NR³R⁴), can be taken together with the nitrogen atom to which they are attached to form a heterocycle selected from the group consisting of 1-aziridinyl, 1-azetidinyl, 1-piperidinyl, 1-morpholinyl, 1-pyrrolidinyl, thiamorpholinyl, thiazolidinyl, and 1-piperazinyl, said heterocycle being optionally substituted with 0–3 groups selected from the group consisting of oxo, R⁶, C₁–C₆ alkyl, C₃–C₇ cycloalkyl (C₀–C₄alkyl)-, C₁–C₆alkylcarbonyl, C₃–C₇ cycloalkyl(C₀₋₅alkyl)carbonyl, C₁–C₆alkoxycarbonyl, C₃–C₇ cycloalkyl (C₀–C₅alkoxy)carbonyl, aryl(C₀–C₅alkyl), heterocyclic(C₀–C₅alkyl), aryl(C₁–C₅alkoxy) carbonyl, heterocyclic(C₁–C₅alkoxy)carbonyl, C₁–C₆alkylsulfonyl, arylsulfonyl, and heterocyclicsulfonyl, R⁵ is selected from (C₁–C₄)alkyl, (C₂–C₄)alkenyl, (C₂–C₄)alkynyl, aryl(C₀–C₄)alkyl-, heterocyclic (C₀–C₄)alkyl-, or cycloalkyl(C₀–C₄)alkyl-, and each R⁵ optionally comprises up to 2 different or identical substituents selected from R⁶;

R⁵ᵃ is selected from (C₁–C₄)alkyl, (C₂–C₄)alkynyl, (C₂–C₄)alkynyl, aryl(C₁–C₄)alkyl-, heterocyclic (C₁–C₄)alkyl-, or cycloalkyl(C₁–C₄) alkyl-, and each R⁵ᵃ optionally comprises up to 2 different or identical substituents selected from R⁶;

R⁶ is selected from H, halogen, NO₂, CN, C₁–C₄alkyl, C₃–C₁₀ cycloalkyl, C₂–C₆alkenyl, C₂–C₆alkynyl, haloalkyl, haloalkoxy, OH, hydroxy C₁–C₄alkyl, C₁–C₄alkoxy, C₁–C₄alkylcarbonyl, NH₂, (C₀–C₄alkyl)₀₋₂alkylamino, C₀–C₄alkylthio, C₁–C₄alkylsulfonyl, aryl C₀–C₄alkylsulfonyl, (C₀–C₄alkyl)₀₋₂alkylaminosulfonyl-, (C₀–C₄alkylcarbonylaminosulfonyl-, arylC₀–C₄alkylsulfonylaminocarbonyl, C₁–C₄alkylsulfonylaminocarbonyl carboxylate, C₁–C₄alkyloxycarbonyl, (C₀–C₄alkyl)₀₋₂aminocarbonyl-, and (C₀–C₄alkyl)tetrazol-5-yl;

M is selected from the group consisting of:
(i) (C₁–C₆)alkyl, (C₂–C₆)alkenyl, (C₂–C₆)alkynyl, and cycloalkyl(C₁–C₄)alkyl, optionally comprising up to 3 substituents selected from the group consisting of R¹, R², and R⁴, wherein any CH₂ is optionally substituted with oxo (=O); and (ii)

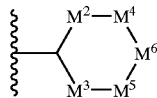

wherein

M² is a heteroatom selected from the group consisting of nitrogen, oxygen and sulfur, or is CP²;

M³ is a heteroatom selected from the group consisting of nitrogen, oxygen and sulfur, or is CP³;

M⁴ is a heteroatom selected from the group consisting of nitrogen, oxygen and sulfur, or is CP⁴, M⁵ is a heteroatom selected from the group consisting of nitrogen, oxygen and sulfur, or is CP⁵;

M⁶ is heteroatom selected from the group consisting of nitrogen, oxygen and sulfur, or is CP⁶ or a bond;

wherein M², M³, M⁴, M⁵, and M⁶, are chosen such that the total number of heteroatoms in the monocyclic ring does not exceed four, and wherein M², M³, M⁴, M⁵, and M⁶ are selected such that the group M defines a five or six membered monocyclic carbocyclic or heterocyclic ring;

P² is selected from H, C₁–C₃alkyl and halo;

P³ is selected from H, C₁–C₃alkyl and halo;

P⁴ is selected from R², R⁵, R⁷, R⁸ and R⁹;

P⁵ is selected from R² and R³;

P⁶ is selected from R², R³, R⁴, R⁷, R⁸ and R⁹;

R⁷ is selected from (C₀–C₆)alkyl, (C₂–C₆)alkenyl and (C₂–C₆)alkynyl and R⁷ is substituted with:

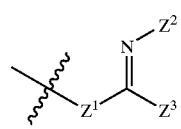

R⁸ is elected from (C₀–C₆)alkyl, (C₂–C₆)alkenyl and (C₂–C₆)alkynyl and R⁸ is substituted with:

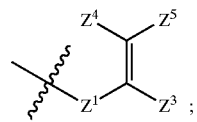

R⁹ is selected from (C₀–C₆)alkyl or (C₂–C₆) alkenyl and alkynyl and R⁹ is substituted with:

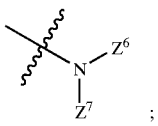

$Z^1$ is selected from the group consisting of O, S, and $NR^3$;

$Z^2$ is selected from the group consisting of H, $C_1$–$C_4$alkyl, $C_3$–$C_6$cycloalkyl, CN, $CF_3$, $OR^3$, heterocycle, $NO_2$, $C(O)R^3$, $C(O)_2R^3$, $C(O)NR^3R^4$, $S(O)_2NR^3R^4$, and $S(O)_2R^5$;

$Z^3$ is selected from the group consisting of $OR^3$, $SR^3$, and $NR^3R^4$;

$Z^4$ is selected from the group consisting of H, halo, $C_1$–$C_4$alkyl, $C_3$–$C_6$cycloalkyl, CN, $CF_3$, heterocycle, $NO_2$, $C(O)R^3$, $C(O)_2R^3$, $C(O)NR^3R^4$, $S(O)_2NR^3R^4$, and $S(O)_2R^5$;

$Z^5$ is selected from the group consisting of halo, CN, $CF_3$, heterocycle, $NO_2$, $C(O)R^3$, $C(O)_2R^3$, $C(O)NR^3R^4$, $S(O))_2NR^3R^4$, and $S(O)_2R^5$;

$Z^6$ is selected from the group consisting of H, $C(O)H$, $C(O)OR^3$, $C(O)OR^4$, $C(O)NR^3R^4$, $S(O)R^5$ and $S(O)_2R^5$;

$Z^7$ is selected from the group consisting of OH, $OR^3$ and $NR^3R^4$, $R^{10}$ is selected from hydrogen, $(C_1$–$C_4)$alkyl, $(C_2$–$C_4)$ alkenyl or alkynyl, aryl, heterocyclic, and cycloalkyl, wherein said groups are substituted with 0–2 substitutents independently selected from $R^{11}$ or $R^{12}$;

$R^{11}$ is selected from the group consisting of H, halogen, $NO_2$, CN, $C_1$–$C_4$alkyl, $C_3$–$C_{10}$ cycloalkyl, $C_2$–$C_6$alkenyl, $C_2$–$C_6$alkynyl, haloalkyl, haloalkoxy, OH, $C_1$–$C_4$alkoxy, $C_1$–$C_4$alkylcarbonyl, $NH_2$, $(C_0$–$C_4$alkyl$)_{0-2}$alkylamino, $C_0$–$C_4$alkylthio, $C_1$–$C_4$alkylsulfonyl, aryl $C_0$–$C_4$alkylsulfonyl, $(C_0$–$C_4$alkyl$)_{0-2}$alkylaminosulfonyl-, $(C_0$–$C_4$alkylcarbonylaminosulfonyl-, aryl$C_0$–$C_4$alkylsulfonylaminocarbonyl, $C_1$–$C_4$alkylsulfonylaminocarbonyl carboxylate, $C_1$–$C_4$alkyloxycarbonyl, $(C_0$–$C_4$alkyl$)_{0-2}$aminocarbonyl-, and $(C_0$–$C_4$alkyl)tetrazol-5-yl;

$R^{12}$ is selected from H, alkyl, $(C_1$–$C_6)$alkyloxy, $C_3$–$C_6$cycloalkyl, heterocyclic and aryl.

2. A compound selected from the group consisting of (i):

N-Cyano-N'-cyclohexyl-N"-[3-methoxy-4-(5-oxazolyl) phenyl]guanidine;

N-Cyano-N'-(1-cyclohexylethyl)-N"-[3-methoxy-4-(5-oxazolyl)-phenyl]guanidine;

N-Cyano-N'-[3-methoxy-4-(5-oxazolyl)phenyl]-N"-propylguanidine;

N-Cyano-N'-(2,3-dihydro-1H-inden-2-yl)-N"-[3-methoxy-4-(5-oxazolyl)-phenyl]guanidine;

N-Cyano-N'-cyclopentyl-N"-[3-methoxy-4-(5-oxazolyl) phenyl]guanidine;

N-Cyano-N'-[3-methoxy-4-(5-oxazolyl)phenyl]-N"-[(5-methyl-2-furanyl)methyl]guanidine;

N-Cyano-N'-[3-methoxy-4-(5-oxazolyl)phenyl]-N"-(2-thienylmethyl)-guanidine;

N-Cyano-N'-[3-methoxy-4-(5-oxazolyl)phenyl]-N"-[(2-methylphenyl)-methyl]guanidine;

N-Cyano-N'-[3-methoxy-4-(5-oxazolyl)phenyl]-N"-[(3-methylphenyl)-methyl]guanidine;

N-[(2-Bromophenyl)methyl]-N'-cyano-N"-[3-methoxy-4-(5-oxazolyl)-phenyl]guanidine ;

N-[(4-Chlorophenyl)methyl]-N'-cyano-N"-[3-methoxy-4-(5-oxazolyl)phenyl]guanidine;

N-(Bicyclo[2.2.1]heptan-2-yl)-N'-cyano-N"-[3-methoxy4-(5-oxazolyl)-phenyl]guanidine;

N-Cyano-N'-[3-methoxy-4-(5-oxazolyl)phenyl]-N"-(4-methylcyclohexyl)-guanidine ;

N-Cyano-N'-[3-methoxy-4-(5-oxazolyl)phenyl]-N"-(3-methylbutyl)-guanidine;

N-[(4-Aminophenyl)methyl]-N'-cyano-N'-[3-methoxy-4-(5-oxazolyl)-phenyl]guanidine;

N-Cyano-N'-(cyclopropylmethyl)-N"-[3-methoxy-4-(5-oxazolyl)phenyl]-guanidine;

N-Butyl-N'-cyano-N"-[3-methoxy-4-(5-oxazolyl)phenyl] guanidine;

N-[(3-Chlorophenyl)methyl]-N'-cyano-N"-[3-methoxy-4-(5-oxazolyl)-phenyl]guanidine;

N-Cyano-N'-[4-(1,1-dimethylethyl)cyclohexyl]-N'-[3-methoxy-4-(5-oxazolyl)phenyl]guanidine;

N-Cyano-N'-(3-methoxy4-(5-oxazolyl)phenyl)-N"-phenylguanidine;

N-Cyano-N'-(3-methoxy-4-(5-oxazolyl)phenyl)-N"-(2-methylphenyl)-guanidine;

N-Cyano-N'-(3-methoxy4-(5-oxazolyl)phenyl)-N"-(4-methylphenyl)-guanidine;

N-Cyano-N'-[3-methoxy-4-(5-oxazolyl)phenyl]-N"-[3-(1-methylethyl)phenyl]guanidine;

N-Cyano-N'-[3-methoxy-4-(5-oxazolyl)phenyl]-N"-[3-(trifluoromethoxy)-phenyl]guanidine;

N-Cyano-N'-[3-(1,1-dimethylethyl)phenyl]-N"-[3-methoxy-4-(5-oxazolyl)phenyl]guanidine;

N-Cyano-N'-[3-methoxy-4-(5-oxazolyl)phenyl]-N"-[3-(2-phenoxy-ethoxy)phenyl]guanidine;

N-Cyano-N'-[3-(hydroxymethyl)phenyl]-N"-[3-methoxy-4-(5-oxazolyl)phenyl]guanidine;

N-Cyano-N'-[3-methoxy-4-(5-oxazolyl)phenyl]-N"-(2-phenylcyclopropyl)guanidine;

N-Cyano-N'-[3-methoxy-4-(5-oxazolyl)phenyl]-N"-3-pyridinylguanidine;

[[3-[[(Cyanoamino)[[3-methoxy4-(5-oxazolyl)phenyl] amino]methylene]amino]phenyl]methyl]carbamic acid tetrahydro-3-furanyl ester;

[[3-[[(Cyanoamino)[[3-methoxy-4-(5-oxazolyl)phenyl] amino]methylene]amino]phenyl]methyl]carbamic acid tetrahydro-3-furanylmethyl ester;

and (ii) a pharmaceutically-acceptable salt thereof.

3. A pharmaceutical composition comprising a pharmaceutically acceptable carrier, adjuvant or vehicle and at least one compound of claim 1, or a pharmaceutically acceptable salt thereof.

4. A compound having the formula:

or a pharmaceutically-acceptable salt thereof, in which $Y^1$ at each occurrence is selected independently from hydrogen, $C_{1-3}$alkyl, and halogen;

W is selected from hydrogen, halogen, $C_1$–$C_4$alkyl, $C_2$–$C_4$alkenyl, CN, $NO_2$, $CF_3$, $(C_0$–$C_4$alkyl)O($C_1$–$C_4$) alkyl, $(C_0$–$C_4$alkyl)OH, and $OCF_3$;

$R^1$ is oxazolyl having 0 to 3 substituents selected from halogen, $C_1$-$C_4$alkyl, CN, $NO_2$, $CF_3$, ($C_0$-$C_4$alkyl)O($C_1$-$C_4$)alkyl, ($C_0$-$C_4$alkyl)OH, and $OCF_3$;

M is selected from
(i) ($C_1$-$C_6$)alkyl and cycloalkyl($C_1$-$C_4$)alkyl optionally having up to 3 substituents selected from $R^1$, $R^2$, and $R^4$;
(ii) monocyclic or bicyclic cycloalkyl optionally substituted with $C_1$-$C_4$alkyl and/or phenyl; and
(iii)

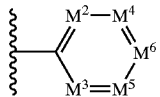

wherein
$M^2$ is N or $CP^2$;
$M^3$ is N or $CP^3$;
$M^4$ is N or $CP^4$;
$M^5$ is N or $CP^5$;
$M^6$ is N or $CP^6$;
$P^2$, $P^3$, $P^5$ and $P^6$ are selected from hydrogen, $C_1$-$C_3$alkyl, and halogen;

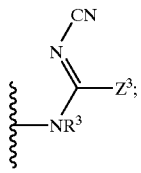

$P^4$ is selected from hydrogen, $R^2$, $R^5$, and —($C_0$-$C_6$)alkyl substituted with $Z^3$;
$Z^3$ is $OR^3$ or $NR^3R^4$;
$R^2$ is selected from halogen, CN, $NO_2$, $CF_3$, ($C_0$-$C_4$alkyl)$OR^3$, $OCF_3$, $OC(O)R^3$, $OC(O)OR^3$, $O(C)NR^3R^4$, ($C_0$-$C_4$alkyl)$C(O)R^3$, ($C_0$-$C_4$alkyl)$C(O)OR^3$, ($C_0$-$C_4$alkyl)$C(O)NR^3R^4$, ($C_0$-$C_4$alkyl)$CONR^3S(O)_2R^5$, ($C_0$-$C_4$alkyl)$C(O)N(OR^3)R^3$, ($C_0$-$C_4$alkyl)$SR^3$, $C_0$-$C_4$alkyl)$S(O)R^5$, ($C_0$-$C_4$alkyl)$S(O)_2R^5$, ($C_0$-$C_4$alkyl)$S(O)_2NR^3R^4$, ($C_0$-$C_4$alkyl)$S(O)_2NR^3C(O)OR^4$, ($C_0$-$C_4$alkyl)$NR^3R^4$, ($C_0$-$C_4$alkyl)$NR^3C(O)NR^3R^4$, ($C_0$-$C_4$alkyl)$NR^3C(O)R^4$, ($C_0$-$C_4$alkyl)$NR^3C(O)OR^5$, ($C_1$-$C_4$alkyl)$NR^3C(O)OR^5$, ($C_0$-$C_4$alkyl)$NR^3S(O)_2R^5$, ($C_0$-$C_4$alkyl)$S(O)_2OR^3$, ($C_0$-$C_4$alkyl)$P(O)(OH)OR^3$, —J—($C_0$-$C_4$alkyl)$OR^3$, —J—($C_1$-$C_4$alkyl)$C(O)OR^3$, —J—($C_1$-$C_4$alkyl)$CONR^3S(O)_2R^5$, —J—($C_1$-$C_4$alkyl)$S(O)_2NR^3R^4$, —J—($C_1$-$C_4$alkyl)$S(O)_2NR^3C(O)R^4$, ($C_0$-$C_4$alkyl)tetrazol-5-yl, and —J—($C_1$-$C_4$alkyl)tetrazol-5-yl, wherein J is chosen from O, S, and $NR^3$;

$R^3$ at each occurrence is selected independently from hydrogen, ($C_1$-$C_4$)alkyl, ($C_2$-$C_4$)alkenyl, ($C_2$-$C_4$)alkynyl, aryl($C_0$-$C_4$)alkyl-, heterocyclic($C_0$-$C_4$)alkyl-, and cycloalkyl($C_0$-$C_4$)alkyl-, wherein each $R^3$ group has 0–2 substituents independently selected from $R^6$;

$R^4$ at each occurrence is selected independently from hydrogen, ($C_1$-$C_4$)alkyl, ($C_2$-$C_4$)alkenyl, ($C_2$-$C_4$) alkynyl, aryl($C_0$-$C_4$)alkyl-, heterocyclic($C_0$-$C_4$) alkyl-, cycloalkyl, ($C_0$-$C_4$)alkylcarbonyl, aryl ($C_0$-$C_4$)alkylcarbonyl, heterocyclic($C_0$-$C_4$)alkylcarbonyl, ($C_1$-$C_4$)alkyloxycarbonyl, aryl ($C_1$-$C_4$)alkyloxycarbonyl, and heterocyclic ($C_1$-$C_4$)alkyloxycarbonyl, wherein each $R^4$ group has 0–2 substituents independently selected from $R^6$;

alternatively, $R^3$ and $R^4$, when both substituents are on the same nitrogen atom, can be taken together with the nitrogen atom to which they are attached to form a heterocycle selected from the group consisting of 1-aziridinyl, 1-azetidinyl, 1-piperidinyl, 1-morpholinyl, 1-pyrrolidinyl, thiamorpholinyl, thiazolidinyl, and 1-piperazinyl, said heterocycle being optionally substituted with 0–3 groups selected from oxo and $R^6$;

$R^5$ is selected from ($C_1$-$C_4$)alkyl, ($C_2$-$C_4$)alkenyl, ($C_2$-$C_4$)alkynyl, aryl($C_0$-$C_4$)alkyl-, heterocyclic ($C_0$-$C_4$)alkyl-, or cycloalkyl($C_0$-$C_4$)alkyl-, and each $R^5$ optionally comprises up to 2 different or identical substituents selected from $R^6$; and $R^6$ at each occurrence is independently selected from halogen, $NO_2$, CN, $C_1$-$C_4$alkyl, $C_3$-$C_{10}$cycloalkyl, $C_2$-$C_6$alkenyl, $C_2$-$C_6$alkynyl, haloalkyl, haloalkoxy, OH, hydroxy($C_1$-$C_4$alkyl), $C_1$-$C_4$alkoxy, phenoxy, $C_1$-$C_4$alkylcarbonyl, $NH_2$, ($C_0$-$C_4$alkyl)$_{0-2}$alkylamino, $C_0$-$C_4$alkylthio, $C_1$-$C_4$alkylsulfonyl, aryl $C_0$-$C_4$alkylsulfonyl, ($C_0$-$C_4$alkyl)$_{0-2}$ alkylaminosulfonyl-, ($C_0$-$C_4$alkylcarbonylaminosulfonyl-, aryl$C_0$-$C_4$alkylsulfonylaminocarbonyl, $C_1$-$C_4$alkylsulfonylaminocarbonyl carboxylate, $C_1$-$C_4$alkyloxycarbonyl, ($C_0$-$C_4$alkyl)$_{0-2}$aminocarbonyl-, and ($C_0$-$C_4$alkyl)tetrazol-5-yl.

5. A pharmaceutical composition comprising a pharmaceutically acceptable carrier, adjuvant or vehicle and at least one compound of claim 4, or a pharmaceutically acceptable salt thereof.

6. A method for the treatment of rheumatoid arthritis, comprising the step of administering to a subject in need thereof an amount effective therefor of at least one compound of claim 1 or a pharmaceutically acceptable salt thereof.

7. A method for the treatment of rheumatoid arthritis, comprising the step of administering to a subject in need thereof an amount effective therefor of at least one compound of claim 4 or a pharmaceutically acceptable salt thereof.

8. The compound of claim 4, or a pharmaceutically-acceptable salt thereof, in which W is hydroxy, methoxy, or ethoxy.

9. The compound of claim 4, or a pharmaceutically-acceptable salt thereof, in which $R^1$

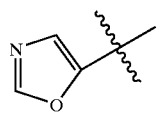

10. The compound of claim 4, or a pharmaceutically-acceptable salt thereof, in which two of $Y^1$ are hydrogen and the other of $Y^1$ is selected from hydrogen, $C_{1-3}$alkyl, and halogen.

11. The compound of claim 4, or a pharmaceutically-acceptable salt thereof, in which

[structure: phenyl ring with M⁴ substituent]

M is
M⁴ is N or CP⁴; and
P⁴ is independently selected from hydrogen, halogen, (C₁–C₄)alkyl, CN, NO₂, CF₃, (C₀–C₄alkyl)OR³, OCF₃, (C₀–C₄alkyl)NR³R⁴, (C₀–C₄alkyl)NHC(O)NR³R⁴, (C₀–C₄alkyl)NHC(O)R⁴, C₀–C₄alkyl)NHC(O)OR⁵, (C₁–C₄alkyl)NHC(O)NR³R⁵, —O—(C₀₋₄alkyl)OR³, and —(C₁–C₃)alkyl substituted

[structure: N=C(Z³)(NH–)(N–CN)]

12. The compound of claim 4, or a pharmaceutically-acceptable salt thereof, in which M is selected from:
   (i) (C₁–C₆)alkyl optionally having one to two substituents selected from cycloalkyl, five to six membered heterocycle, or phenyl, wherein said cycloalkyl, heterocycle or phenyl is optionally substituted with one to two of halogen, C₁₋₃alkyl and NH₂; and
   (ii) C₃–C₇monocyclic or C₇bicyclic cycloalkyl optionally substituted with C₁–C₄alkyl and/or phenyl.

13. The compound of claim 4, having the formula:

[structure]

or a pharmaceutically-acceptable salt thereof.

14. The compound of claim 4, having the formula:

[structure]

or a pharmaceutically-acceptable salt thereof.

15. A compound having the formula:

[structure]

or a pharmaceutically-acceptable salt thereof, in which
   W is selected from hydrogen, halogen, C₁–C₄alkyl, CN, NO₂, CF₃, (C₀–C₄alkyl)O(C₁–C₄)alkyl, (C₀–C₄alkyl)OH, and OCF₃;
   R¹ is oxazolyl optionally substituted with 0 to 3 substituents selected from halogen, C₁–C₄alkyl, CN, NO₂, CF₃, (C₀–C₄alkyl)O(C₁–C₄)alkyl, (C₀–C₄alkyl)OH, and OCF₃;
   M is selected from
   (i) (C₁–C₆)alkyl optionally having one to two substituents selected from cycloalkyl, five to six membered heterocycle, or phenyl, wherein said cycloalkyl, heterocycle or phenyl is optionally substituted with one to two of halogen, C₁₋₃alkyl and NH₂;
   (ii) monocyclic or bicyclic cycloalkyl optionally substituted with C₁–C₄alkyl and/or phenyl; and
   (iii)

[structure: 6-membered ring with M²–M⁴, M³=M⁵, M⁶]

wherein
   M² is N or CP²; M³ is N or CP³; M⁴ is N or CP⁴; M⁵ is N or CP⁵; and M⁶ is N or CP⁶;
   P², P³, P⁵, and P⁶ are independently selected from hydrogen, C₁–C₃alkyl, and halogen;
   P⁴ is selected from
   (i) hydrogen, halogen, CN, NO₂, CF₃, (C₀–C₄alkyl)OR³, OCF₃, OC(O)R³, OC(O)OR³, O(C)NR³R⁴, (C₀–C₄alkyl)C(O)R³, (C₀–C₄alkyl)C(O)OR³, (C₀–C₄alkyl)C(O)NR³R⁴, (C₀–C₄alkyl)C(O)N(OR³)R³, (C₀–C₄alkyl)SR³, —(C₀–C₄alkyl)S(O)₂NR³R⁴, (C₀–C₄alkyl)S(O)₂NR³C(O)R⁴, (C₀–C₄alkyl)NR³R⁴, (C₀–C₄alkyl)NR³C(O)NR³R⁴, (C₀–C₄alkyl)NR³C(O)R⁴, —J—(C₀–C₄alkyl)OR³, —J—(C₁–C₄alkyl)C(O)OR³, wherein J is O or NH;
   (ii) (C₁–C₄)alkyl, (C₂–C₄)alkenyl, aryl(C₀–C₄)alkyl-, heterocyclic(C₀–C₄)alkyl-, or cycloalkyl(C₀–C₄)alkyl-, and each R⁵ optionally has up to 2 substituents selected from R⁶; and

[structure: N=C(Z³)(NR³–)(N–CN)]

(iii) —(C₀–C₄)alkyl substituted with
   Z³ is OR³ or NR³R⁴;
   R³ is hydrogen or C₁₋₄alkyl and is optionally substituted with 1–2 R⁶;
   R⁴ is hydrogen, C₁₋₄alkyl, aryl(C₀₋₄alkyl), (C₁–C₄)alkyloxycarbonyl, aryl(C₁–C₄)alkyloxycarbonyl, or heterocyclic(C₁–C₄)alkyloxycarbonyl, wherein each R⁴ group has 0–2 substituents independently selected from R⁶; or
   alternatively, R³ and R⁴, when both substituents are on the same nitrogen atom, can be taken together with the nitrogen atom to which they are attached to form a heterocycle selected from the group consisting of 1-aziridinyl, 1-azetidinyl, 1-piperidinyl, 1-morpholinyl, 1-pyrrolidinyl, thiamorpholinyl, thiazolidinyl, and 1-piperazinyl; and $R^6$ is hydrogen, $C_{1-4}$alkyl, phenyl, hydroxy, hydroxy($C_1$–$C_4$)alkyl, alkoxy or phenyloxy.

16. The compound of claim 15, or a pharmaceutically-acceptable salt thereof, having the formula:

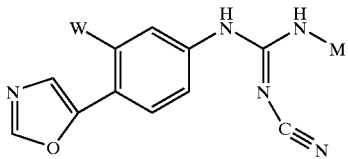

17. The compound of claim 15, or a pharmaceutically-acceptable salt thereof, in which M is selected from —$C_{1-6}$alkyl, —$C_{0-4}$alkyl(cyclopropyl), —$C_{0-4}$alkyl(cyclobutyl), —$C_{0-4}$alkyl(cyclopentyl), —$C_{0-4}$alkyl(cyclohexyl), —$C_{0-4}$alkyl(heptanyl), —$C_{0-4}$alkyl(bicycloheptanyl), —$C_{1-4}$alkyl(pyridinyl), —$C_{1-4}$alkyl(furanyl), —$C_{1-4}$alkyl(thienyl), and —$C_{0-4}$alkyl(phenyl), where M has 0–2 substituents selected from $C_{1-4}$alkyl, halogen, $NH_2$, hydroxy$C_{1-4}$alkyl, O—$(CH_2)_2$—O—phenyl, $C_{0-4}$alkylNHCO$_2$(tetrahydrofuranyl), —$C_{0-4}$alkylNHCO$_2$CH$_2$(tetrahydrofuranyl); or where M is phenyl, M is optionally substituted with —($C_1$–$C_3$)alkyl substituted with

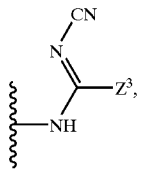

and $Z^3$ is O($C_{1-3}$alkyl), OCH$_2$(heterocycle), OPh, NH$_2$, 1-morpholinyl, —NH—(CH$_2$)$_2$-imidazole, piperidine, NH-cyclohexyl, —NH—(CH$_2$)pyridine, —NH—(CH$_2$)tetrahydrofuran, piperazine, NH($C_{1-3}$alkyl, or pyridine, wherein $Z^3$ is optionally substituted with hydroxy or hydroxy$C_{1-3}$alkyl.

18. A method for the treatment of inflammatory bowel disease, comprising the step of administering to a subject in need thereof an amount effective therefor of at least one compound of claim 1 or a pharmaceutically acceptable salt thereof.

19. A method for the treatment of asthma, comprising the step of administering to a subject in need thereof an amount effective therefor of at least one compound of claim 1 or a pharmaceutically acceptable salt thereof.

20. A method for the treatment of transplant rejection, comprising the step of administering to a subject in need thereof an amount effective therefor of at least one compound of claim 1 or a pharmaceutically acceptable salt thereof.

21. A method for the treatment of multiple sclerosis, comprising the step of administering to a subject in need thereof an amount effective therefor of at least one compound of claim 1 or a pharmaceutically acceptable salt thereof.

22. A method for the treatment of juvenile diabetes, comprising the step of administering to a subject in need thereof an amount effective therefor of at least one compound of claim 1 or a pharmaceutically acceptable salt thereof.

23. A method for the treatment of hepatitis B, hepatitis C, herpes simplex I, and/or herpes simplex II, comprising the step of administering to a subject in need thereof an amount effective therefor of at least one compound of claim 1 or a pharmaceutically acceptable salt thereof.

* * * * *